United States Patent
Linders et al.

(10) Patent No.: US 8,993,855 B2
(45) Date of Patent: Mar. 31, 2015

(54) INSECT RESISTANT PLANT

(75) Inventors: Enrico Gerardus Albertus Linders, Enkhuizen (NL); Jean Louis Marie Edouard Nicolet, Sarrians (FR); Henricus Johannes Van Wijk, Saint-Sauveur (FR)

(73) Assignee: Syngenta Participations AG, Basel (CH)

( * ) Notice: Subject to any disclaimer, the term of this patent is extended or adjusted under 35 U.S.C. 154(b) by 1459 days.

(21) Appl. No.: 12/451,236

(22) PCT Filed: Apr. 30, 2008

(86) PCT No.: PCT/EP2008/055374
§ 371 (c)(1),
(2), (4) Date: Jan. 27, 2010

(87) PCT Pub. No.: WO2008/135510
PCT Pub. Date: Nov. 13, 2008

(65) Prior Publication Data
US 2010/0122383 A1    May 13, 2010

(30) Foreign Application Priority Data

May 2, 2007  (EP) .................................... 07290556
Oct. 30, 2007  (EP) .................................... 07119649

(51) Int. Cl.
*A01H 5/00* (2006.01)
*C12Q 1/68* (2006.01)
*A01H 5/08* (2006.01)

(52) U.S. Cl.
CPC .................................... *A01H 5/08* (2013.01)
USPC .................... 800/317.1; 800/267; 800/265

(58) Field of Classification Search
None
See application file for complete search history.

(56) References Cited

FOREIGN PATENT DOCUMENTS

WO    WO 2005019408 A2 *  3/2005

OTHER PUBLICATIONS

Ben Chaim et al. Genome 46: 1-9, 2003.*
Fery et al. Hort Science (1991) 26: 1073-1074.*
Nombela et al (2003) Molec. Plant-Microbe Interactions 16: 645-649.*
Kaloshian et al (1998) Mol. Gen. Genet. 257: 376-385.*
Thabius et al (2004) Molec. Breeding 14: 9-20.*
Zygier et al (2005) Theor. Appl. Genet. 111:437-445.*
Fery et al (1991) Hort Science 26: 1073-1074.*
Slate (2005) Molecular Ecology 14 363-379.*
Chaim, A.B et al., fs3.1: a major fruit shape QTL conserved in Capsicum. Genome. (2002). 46, p. 1-9. NRC Canada.
Fery, R.L. et al., Resistance in pepper (*Capsicum annuum* L.) to western flower thrips [*Frankliniella occidentalis* (Pergande)]. Hort Science. (1991). 26(8), p. 1073-1074.
Kumar, N.K. et al., Initial screening of chili and sweet pepper germplasm for resistance to chili thrips, *Scirtothrips dorsalis* Hood. Euphytica. (1996). 89, p. 319-324. Kluwer Academic Publishers. Netherlands.
Laska, P. et al., Resistance to the glasshouse whitefly (*Trialeurodes vaporariorum* Westw.) in sweet pepper (*Capsicum annuum* L.). Euphytica. (1982). p. 977-980.
Maris, P.C. et al., Thrips resistance in pepper and its consequences for the acquisition and inoculation of tomato spotted wilt virus by the western flower thrips. Phytopathology. (2003). 93(1), p. 96-101. The American Phytopathological Society. Wageningen, the Netherlands.
Maruthi, M.N. et al., Resistance of tomato and sweet-pepper genotypes to tomato leaf curl Banglore virus and its vector *Bemisia tabaci*. International Journal of Pest Management. (2003). 49(4), p. 297-303. Taylor & Francis Ltd.
Nombela, G. et al., The root-knot nematode resistance gene Mi-1.2 of tomato is responsible for resistance against the whitefly *Bemisia tabaci*. (2003). 16(7), p. 645-649. The American Phytopathological Society.
Thabuis, A. et al., Marker-assisted introgression of 4 Phytophthora capsci resistance QTL alleles into a bell pepper line: validation of additive and epistatic effects. Molecular Breeding. (2004). 14, p. 9-20. Kluwer Academic Publishers. Netherlands.
Maruthi et al., International Journal of Pest Management, Oct.-Dec. 2003, 49, 4, 297-303.
Fery et al., HortScience, 1991, 26, 8, 1073-1074.
Laska et al., Euphytica, 1982, 31, 977-980.
Maris et al., Phytopathology, 2003, 93, 1, 96-101.
Thabuis et al., Molecular Breeding, 2004, 14, 9-20.
Chaim et al., Genome, 2003, 46, 1-9.
Nombela et al., MPMI, 2003, 16, 7, 645-649.

* cited by examiner

*Primary Examiner* — David T Fox
*Assistant Examiner* — Steven Bernacki
(74) *Attorney, Agent, or Firm* — Karen A. Magri

(57) ABSTRACT

The present invention relates to novel pepper plants resistant to insects, and to seeds and fruits of said plants. The present invention also relates to methods of making and using such plants and their fruits. The invention further relates to markers and the use thereof in marker assisted breeding and for identifying the insect resistance trait. In particular, the present invention provides a cultivated *Capsicum annuum* plant which is resistant, particularly intermediately resistant, to infestations by insects of the family Thripidae and/or the genus *Bemisia*, but especially to infestations by *Bemisia tabaci* and *Frankliniella occidentalis*.

7 Claims, No Drawings

SEQUENCE LISTING

```
<160> NUMBER OF SEQ ID NOS: 26

<210> SEQ ID NO 1
<211> LENGTH: 22
<212> TYPE: DNA
<213> ORGANISM: artificial sequence
<220> FEATURE:
<223> OTHER INFORMATION: Capsicum annuum

<400> SEQUENCE: 1
tgctgggaaa gatctcaaaa gg                                            22

<210> SEQ ID NO 2
<211> LENGTH: 21
<212> TYPE: DNA
<213> ORGANISM: artificial sequence
<220> FEATURE:
<223> OTHER INFORMATION: Capsicum annuum

<400> SEQUENCE: 2
atcaaggaag caaaccaatg c                                             21

<210> SEQ ID NO 3
<211> LENGTH: 20
<212> TYPE: DNA
<213> ORGANISM: artificial sequence
```

```
<220> FEATURE:
<223> OTHER INFORMATION: Capsicum annuum

<400> SEQUENCE: 3
gcagcgttac caaataaccg                                                20

<210> SEQ ID NO 4
<211> LENGTH: 26
<212> TYPE: DNA
<213> ORGANISM: artificial sequence
<220> FEATURE:
<223> OTHER INFORMATION: Capsicum annuum

<400> SEQUENCE: 4
tgtttgctat tcaatatatg ctttga                                          26

<210> SEQ ID NO 5
<211> LENGTH: 19
<212> TYPE: DNA
<213> ORGANISM: artificial sequence
<220> FEATURE:
<223> OTHER INFORMATION: Capsicum annuum

<400> SEQUENCE: 5
ggaagcttag ccacacatc                                                  19

<210> SEQ ID NO 6
<211> LENGTH: 21
<212> TYPE: DNA
<213> ORGANISM: artificial sequence
<220> FEATURE:
<223> OTHER INFORMATION: Capsicum annuum

<400> SEQUENCE: 6
accatatttc cgactttgaa c                                               21

<210> SEQ ID NO 7
<211> LENGTH: 19
<212> TYPE: DNA
<213> ORGANISM: artificial sequence
<220> FEATURE:
<223> OTHER INFORMATION: Capsicum annuum

<400> SEQUENCE: 7
tccatcatcg actggagac                                                  19

<210> SEQ ID NO 8
<211> LENGTH: 19
<212> TYPE: DNA
<213> ORGANISM: artificial sequence
<220> FEATURE:
<223> OTHER INFORMATION: Capsicum annuum

<400> SEQUENCE: 8
tgttcaattg gcttctgtg                                                  19

<210> SEQ ID NO 9
<211> LENGTH: 21
<212> TYPE: DNA
<213> ORGANISM: artificial sequence
<220> FEATURE:
<223> OTHER INFORMATION: Capsicum annuum

<400> SEQUENCE: 9
gcaagtagaa caaagggtag g                                               21
```

```
<210> SEQ ID NO 10
<211> LENGTH: 19
<212> TYPE: DNA
<213> ORGANISM: artificial sequence
<220> FEATURE:
<223> OTHER INFORMATION: Capsicum annuum

<400> SEQUENCE: 10
tatttgaagg ttgtgcgac                                                  19

<210> SEQ ID NO 11
<211> LENGTH: 22
<212> TYPE: DNA
<213> ORGANISM: artificial sequence
<220> FEATURE:
<223> OTHER INFORMATION: Capsicum annuum

<400> SEQUENCE: 11
tcatcacatt cacttcattt tc                                              22

<210> SEQ ID NO 12
<211> LENGTH: 24
<212> TYPE: DNA
<213> ORGANISM: artificial sequence
<220> FEATURE:
<223> OTHER INFORMATION: Capsicum annuum

<400> SEQUENCE: 12
ttgattcatt tcagatagtt caag                                            24

<210> SEQ ID NO 13
<211> LENGTH: 19
<212> TYPE: DNA
<213> ORGANISM: artificial sequence
<220> FEATURE:
<223> OTHER INFORMATION: Capsicum annuum

<400> SEQUENCE: 13
ctttggaggt agcggtatg                                                  19

<210> SEQ ID NO 14
<211> LENGTH: 19
<212> TYPE: DNA
<213> ORGANISM: artificial sequence
<220> FEATURE:
<223> OTHER INFORMATION: Capsicum annuum

<400> SEQUENCE: 14
caacaaacga accacaatg                                                  19

<210> SEQ ID NO 15
<211> LENGTH: 19
<212> TYPE: DNA
<213> ORGANISM: artificial sequence
<220> FEATURE:
<223> OTHER INFORMATION: Capsicum annuum

<400> SEQUENCE: 15
cccgtttaca agcaaagag                                                  19

<210> SEQ ID NO 16
<211> LENGTH: 19
<212> TYPE: DNA
<213> ORGANISM: artificial sequence
<220> FEATURE:
<223> OTHER INFORMATION: Capsicum annuum
```

```
<400> SEQUENCE: 16 gaccectgaa gaacctctc                                                    19

<210> SEQ ID NO 17
<211> LENGTH: 19
<212> TYPE: DNA
<213> ORGANISM: artificial sequence
<220> FEATURE:
<223> OTHER INFORMATION: Capsicum annuum

<400> SEQUENCE: 17
tctcttgtca gacacgtcg                                                    19

<210> SEQ ID NO 18
<211> LENGTH: 19
<212> TYPE: DNA
<213> ORGANISM: artificial sequence
<220> FEATURE:
<223> OTHER INFORMATION: Capsicum annuum

<400> SEQUENCE: 18
cttcttggag gcatttttg                                                    19

<210> SEQ ID NO 19
<211> LENGTH: 24
<212> TYPE: DNA
<213> ORGANISM: artificial sequence
<220> FEATURE:
<223> OTHER INFORMATION: Capsicum annuum

<400> SEQUENCE: 19
tgtaggatta caagaacatt atcg                                              24

<210> SEQ ID NO 20
<211> LENGTH: 19
<212> TYPE: DNA
<213> ORGANISM: artificial sequence
<220> FEATURE:
<223> OTHER INFORMATION: Capsicum annuum

<400> SEQUENCE: 20
gcgagctatt acaccgaag                                                    19

<210> SEQ ID NO 21
<211> LENGTH: 19
<212> TYPE: DNA
<213> ORGANISM: artificial sequence
<220> FEATURE:
<223> OTHER INFORMATION: Capsicum annuum

<400> SEQUENCE: 21
taggtgggaa tacactggg                                                    19

<210> SEQ ID NO 22
<211> LENGTH: 20
<212> TYPE: DNA
<213> ORGANISM: artificial sequence
<220> FEATURE:
<223> OTHER INFORMATION: Capsicum annuum

<400> SEQUENCE: 22
cccagatcta ccaaggagtc                                                   20

<210> SEQ ID NO 23
```

```
<211> LENGTH: 20
<212> TYPE: DNA
<213> ORGANISM: artificial sequence
<220> FEATURE:
<223> OTHER INFORMATION: Capsicum annuum

<400> SEQUENCE: 23
tcggcctgac tagtattgac                                              20

<210> SEQ ID NO 24
<211> LENGTH: 18
<212> TYPE: DNA
<213> ORGANISM: artificial sequence
<220> FEATURE:
<223> OTHER INFORMATION: Capsicum annuum

<400> SEQUENCE: 24
cgggtaccag atgtaggg                                                18

<210> SEQ ID NO 25
<211> LENGTH: 19
<212> TYPE: DNA
<213> ORGANISM: artificial sequence
<220> FEATURE:
<223> OTHER INFORMATION: Capsicum annuum

<400> SEQUENCE: 25
atcgtgaggt gagtacgag                                               19

<210> SEQ ID NO 26
<211> LENGTH: 19
<212> TYPE: DNA
<213> ORGANISM: artificial sequence
<220> FEATURE:
<223> OTHER INFORMATION: Capsicum annuum

<400> SEQUENCE: 26
tacctacata cccccaccc                                               19
```

INSECT RESISTANT PLANT

CROSS-REFERENCE TO RELATED APPLICATIONS

This application is a national phase application of International Application No. PCT/EP2008/055374, filed Apr. 30, 2008, which claims priority to European Application No. 07290556.5, filed May 2, 2007 and European Application No. 0711649.7, filed Oct. 30, 2007.

The present invention relates to novel pepper plants resistant to insects, and, to seeds and fruits of said plants. The present invention also relates to methods of making and using such plants and their fruits. The invention further relates to markers and the use thereof in marker assisted breeding and for identifying the insect resistance trait.

Peppers are an important crop worldwide with an estimated commercial value of about 500 million dollars a year. Peppers are Solanaceas from the genus *Capsicum*, which includes the species *Capsicum annuum, Capsicum frutescens* and *Capsicum chinense*. Commercial peppers are diploids with n=12 chromosomes. Peppers are cultivated and used around the world as sweet peppers such as the bell pepper; or as pungent chili peppers, jalapeno peppers, and TABASCO® peppers; or as a source of dried powders of various colors such as paprika. The types of cultivated peppers can be differentiated by pungency, fruit shape, color and size (see for example U.S. Pat. No. 6,498,287).

Pepper fruits, also commonly referred to as "peppers", are highly perishable. They are prone to water loss and shriveling, which renders them unappealing to customers. Pepper plants are also hosts to a number of diseases. These diseases reduce the yield of the crops, but also affect the appearance of the fruits, rendering them unmarketable. In particular, insects cause substantial crop damages, resulting in substantial commercial losses. In some cases, the insects directly affect the plants or the fruits, in other cases they act as a vector for plants viruses. Usually insect damage reduces plant growth but does not commonly kill the plant. Chemical control and crop rotation can be used to reduce the damage caused by insects, but these strategies are expensive and sometimes inconvenient.

Among insect pest affecting peppers, the white fly *Bemisia tabaci* (Hemiptera: Aleyrodidae) and various thrips species such as the Western Flower Thrips: *Frankliniella occidentalis*, the Onion Thrips: *Thrips tabaci*, the Chilli Thrips *Scirtothrips dorsalis*, and the Melon Thrips *Thrips palmi* are particularly devastating.

There are about 5000 described species of thrips (insects in the Order Thysanoptera). The species that feed on higher plants occur mostly in the Family Thripidae. This family includes the important pest species including serious pests of ornamental, vegetable, and fruit crops in the field and greenhouse. Feeding and egg-laying by thrips results in distortion, discoloration, silvering and bronzing of leaves and fruits of vegetables reducing their market value. Some species of thrips are vectors of bunyaviruses (family Bunyaviridae, genus Tospovirus, type species tomato spotted wilt). Severe epidemics occur annually on food, fiber, and ornamental crops in tropical and subtropical regions of the world.

The western flower thrips (*Frankliniella occidentalis*) is an opportunistic insect pest in greenhouses which severely affects a multitude of crops. *Frankliniella occidentalis* was spread nearly worldwide over the past two decades. This thrips species is very damaging and difficult to control. It multiplies easily on pepper and creates physical damages on plant, flowers and fruits from the early stage of the nursery up to the end of the crop. The larvae and adults feed on the epidermal cells of leaves, buds, flowers and fruits. They affect the skin of the fruit and depreciate the marketable value. High-value greenhouse crops such as vegetables are particularly vulnerable to economic losses associated with thrips damage. Thrips is also an efficient vector of a devastating virus, the Tomato Spotted Wilt virus (TSWv) which creates big losses for, the growers. The infected plants present strong mosaic and necrosis on plants and fruits.

Thrips is difficult to control via chemical products as the insect has developed resistance to several insecticides used over the last 15 years. Under greenhouse conditions, the use of biological predators, either with *Orius* in hot conditions or *Amblyseius* in cooler conditions that maintain a low level of thrips in the crop, is a wide spread but not always a sufficient practice.

For the white fly, *Bemisia tabaci*, at least two biotypes have been described: the B-type, identical to *Bemisia argentifolii* and the Q-type.

Control of *Bemisia* and thrips is particularly difficult, also because of the wide range of host plants. *Bemisia* and thrips species attack a wide variety of vegetable crops including tomato, beans, cucumbers, melons, bitter melon, capsicum, eggplant, pumpkin, squash and zucchini. *Capsicum* belongs to the most seriously affected crops.

Because of the damages on plant and fruit and the transmission of a devastating virus, there is an unmet need for convenient and economically sustainable strategies to protect pepper crops against these pests. Host plant resistance is a good control strategy for *Bemisia* and thrips. It is an environmentally friendly alternative for the use of pesticides and may increase the efficiency of biological control options and contribute to successful integrated pest management programs.

The present invention addresses this need by providing resistant pepper plants that are less attractive to insects and/or capable of resisting insect infestation and/or development such as, for example, oviposition and/or pupae development and would thus be to a considerable degree protected from insect infestations, particularly from infestations of the white fly *Bemisia tabaci* and/or thrips.

The present invention provides a cultivated *Capsicum annuum* plant which is resistant, particularly intermediately resistant, to infestations by insects of the family Thripidae and/or the genus *Bemisia*, but especially to infestations by *Bemisia tabaci* and *Frankliniella occidentalis*.

Resistance to *Bemisia* infestations" or "*Bemisia* resistant plant" refers to the plants capability to resist attack, infestation, or colonization by the insect. The level of resistance exhibited by a certain plant can be scored, for example, by means of a standardized Insect Resistance Assay as described in Example 2A herein below using a scale from 1-9 for assessing the severity of the infestation.

In one embodiment, the invention provides a cultivated *Capsicum annuum* plant which is resistant, particularly intermediately resistant, to *Bemisia* infestations, wherein said resistance can be assessed in a standard resistance assay, particularly an assay as described in Example 2A below, and wherein a resistance score is obtained deviating by not more than 3 scales, particularly by not more than 2 scales, but especially by not more than 1 scale from a score obtainable with a *Capsicum annuum* plant of line 061M4387, representative seed of which is deposited under Accession No. NCIMB 41428, when assessed in the same assay to a statistically significant extent and under identical environmental conditions, particularly under the same insect pressure.

In one embodiment, a *Bemisia* resistant. *Capsicum annuum* plant is provided that is capable of resisting insect development, particularly oviposition and/or pupae development on the plant such that the number of pupae on the leaves of the plant determined in a standard resistance assay, particularly an assay as described in Example 2A below, deviates by not more than a factor of 20, particularly by not more than a factor of 15, more particularly by not more than a factor of 10, even more particularly by not more than a factor of 5, but especially by not more than a factor of 2, from the number of pupae obtainable with a *Capsicum annuum* plant of line 061M4387, representative seed of which is deposited under Accession No. NCIMB 41428, when assessed in the same assay to a statistically significant extent and under identical environmental conditions, particularly under the same insect pressure.

In one embodiment a *Bemisia* resistant *Capsicum annuum* plant is provided that is capable of resisting insect development, particularly oviposition and/or pupae development on the plant to essentially the same extent as a *Capsicum annuum* plant of line 061M4387, representative seed of which is deposited under Accession No. NCIMB 41428, when assessed in the same assay to a statistically significant extent and under identical environmental conditions, particularly under the same insect pressure.

In one embodiment, a *Bemisia* resistant *Capsicum annuum* plant is provided that is capable of resisting insect development, particularly oviposition and/or pupae development on the plant, wherein said resistance can be assessed in a standard resistance assay, particularly an assay as described in Example 2A below, and wherein a resistance score is obtained that is at least 2 scales, particularly at least 3 scales, more particularly at least, 4 scales, but especially at least 5 scales higher than the resistance score obtained with a standard susceptible commercial variety, such as, for example, Vergasa or Bikingo, when assessed in the same assay to a statistically significant extent and under identical environmental conditions, particularly under the same insect pressure.

In one embodiment, a cultivated *Capsicum annuum* plant is provided, which is resistant, particularly intermediately resistant, to thrips infestations, especially to infestations with *F. occidentalis*, particularly by preventing plant damage caused by the feeding of thrips on the epidermal cells of leaves, buds, flowers and fruits of the *Capsicum annuum* plant, which results in silvering, loss of leaf colour and deformations of the developing fruit. The *Capsicum* plant's capability of preventing feeding damage caused by thrips can be assessed in a standard resistance assay, particularly an assay as described in Example 2B below, by determining the extent of silvering damage according to a scale ranging from 1-9.

In one embodiment of the invention, a cultivated *Capsicum annuum* plant is provided, which is resistant, particularly intermediately resistant, to thrips infestations, particularly to infestations with *F. occidentalis*, particularly by preventing plant damage caused, by the feeding of thrips on the epidermal cells of leaves, buds, flowers and fruits of the *Capsicum annuum* plant, wherein said resistance can be assessed in a standard resistance assay, particularly an assay as described in Example 2B below, and wherein a resistance score is obtained deviating by not more than 2 scales, particularly by not more than 1 scale, but especially by not more than 0.5 scales from a score obtainable with a *Capsicum annuum* plant of line 061M4387, representative seed of which is deposited under Accession No. NCIMB 41428, when assessed in the same assay to a statistically significant extent, and under identical environmental conditions, particularly under the same insect pressure.

In one embodiment of the invention, the invention provides a cultivated *Capsicum annuum* plant which is resistant, particularly intermediately resistant, to thrips infestations, particularly to infestations with *F. occidentalis*, particularly by preventing plant damage caused by the feeding of thrips on the epidermal cells of leaves, buds, flowers and fruits of the *Capsicum annuum* plant, wherein said resistance can be assessed in a standard resistance assay, particularly an assay as described in Example 2B below, and wherein the silvering damage observed does not deviate by more than 8%, particularly by more than 5%, more particularly by more than 2%, even more particularly by more than 1%, but especially by more than 0.5%, from the damage exhibited on a *Capsicum annuum* plant of line 061M4387, representative seed of which is deposited under Accession No. NCIMB 41428, when assessed in the same assay to a statistically significant extent and under identical environmental conditions, particularly under the same insect pressure.

In one embodiment of the invention, the invention provides a cultivated *Capsicum annuum* plant which is resistant, particularly intermediately resistant, to thrips infestations, particularly to infestations with *F. occidentalis*, particularly by preventing plant damage caused by the feeding of thrips on the epidermal cells of leaves, buds, flowers and fruits of the *Capsicum annuum* plant, to essentially the same extent as a *Capsicum annuum* plant of line 061M4387, representative seed of which is deposited under Accession No. NCIMB 41428, when assessed in the same assay to a statistically significant extent and under identical environmental conditions, particularly under the same insect pressure.

In one embodiment, a cultivated *Capsicum annuum* plant is provided, which is resistant, particularly intermediately resistant, to *Bemisia* and thrips infestations, especially to infestations with *Bemisia tabaci* and *F. occidentalis*, particularly by preventing oviposition and/or pupae development of *Bemisia* and by preventing plant damage caused by the feeding of thrips on the epidermal cells of leaves, buds, flowers and fruits of the *Capsicum annuum* plant, respectively, wherein said resistance can be assessed in a standard resistance assay, particularly an assay as described in Examples 2A and 2B below, and wherein, for *Bemisia*, a resistance score is obtained deviating by not more 3 scales, particularly by not more than 2 scales, but especially by not more than 1 scale from a score obtainable with a *Capsicum annuum* plant of line 061M4387, representative seed of which is deposited under Accession No. NCIMB 41428, and, for thrips, a resistance score is obtained deviating by not more than 2 scales, particularly by not more than 1 scale, but especially by not more than 0.5 scales from a score obtainable with a *Capsicum annuum* plant of line 061M4387, representative seed of which is deposited under Accession No. NCIMB 41428, when assessed in the same assay to a statistically significant extent and under identical environmental conditions, particularly under the same insect pressure.

In one embodiment, a cultivated *Capsicum annuum* plant is provided, which is resistant, particularly intermediately resistant, to *Bemisia* and thrips infestations, especially to infestations with *Bemisia tabaci* and *F. occidentalis*, particularly by preventing oviposition and/or pupae development of *Bemisia* and by preventing plant damage caused by the feeding of thrips on the epidermal cells of leaves, buds, flowers and fruits of the *Capsicum annuum* plant, respectively, to essentially the same extent as a *Capsicum annuum* plant of line 061M4387, representative seed of which is deposited under Accession No. NCIMB 41428, when assessed in the same assay to a statistically significant extent and under identical environmental conditions, particularly under the same insect pressure.

In one embodiment, the present invention provides a cultivated *Capsicum annuum* plant which is resistant, particularly intermediately resistant, to *Bemisia* infestations, wherein said plant contains a genome comprising at least one quantitative trait locus ("QTL") which contributes to *Bemisia* resistance, in particular a cultivated *Capsicum annuum* plant which is resistant, particularly intermediately resistant, to *Bemisia* infestations, wherein said plant contains a genome comprising a quantitative trait locus ("QTL") which contributes to *Bemisia* resistance, wherein said QTL is located on chromosome 0.3 and/or chromosome 5.

In one embodiment, the present invention provides a cultivated *Capsicum annuum* plant which is resistant, particularly intermediately resistant, to *Bemisia* infestations, wherein said plant contains a genome comprising at least two quantitative trait loci ("QTL") which contribute to *Bemisia* resistance, wherein a first QTL is located on chromosome 3 and an second QTL is located on chromosome 5.

In one embodiment, the present invention provides a cultivated *Capsicum annuum* plant which is resistant, particularly intermediately resistant, to thrips infestations, wherein said plant contains a genome comprising at least one quantitative trait locus ("QTL") which contributes to thrips resistance, in particular a cultivated *Capsicum annuum* plant which is resistant, particularly intermediately resistant, to thrips infestations, wherein said plant contains a genome comprising a quantitative trait locus ("QTL") which contributes to thrips resistance, wherein said. QTL is located on chromosome 5.

In one embodiment, the present invention provides a cultivated *Capsicum annuum* plant which is resistant, particularly intermediately resistant, to *Bemisia* and thrips infestations, wherein said plant contains a genome comprising at least one quantitative trait locus ("QTL") which contributes to *Bemisia* resistance and at least one quantitative trait locus ("QTL") which contributes to thrips resistance, respectively. In particular, the invention relates to a cultivated *Capsicum annuum* plant which is resistant, particularly intermediately resistant, to *Bemisia* and thrips infestations as described herein before, wherein said QTL contributing to *Bemisia* resistance is located on chromosome 3 and/or chromosome 5 and said QTL contributing to thrips resistance is located on chromosome 5.

In one embodiment, a cultivated *Capsicum annuum* plant is provided which is resistant, particularly intermediately resistant, to *Bemisia* and thrips infestations, wherein said plant contains a genome comprising quantitative trait loci ("QTL") which contribute to *Bemisia* and thrips resistance, wherein a first QTL contributing to *Bemisia* resistance is located on chromosome 3 and an second QTL contributing to *Bemisia* resistance is located on chromosome 5, and said QTL contributing to thrips resistance is located on chromosome 5.

In one embodiment, the QTL on chromosome 5 is a single QTL contributing to both *Bemisia* and thrips resistance.

In one embodiment, said QTL are obtainable from a plant which has the genetic background of line 061M4387, particularly from a plant which has the genetic background or architecture at the QTL of line 061M4387, but especially from a plant of line 061M4387, representative seed of which is deposited at NCIMB under Accession No. NCIMB 41428, or from a progeny or an ancestor thereof comprising said QTL.

In a further embodiment, the invention relates to a cultivated *Capsicum annuum* plant according to the invention and as described herein before, which plant contains a genome comprising at least one quantitative trait locus ("QTL") which contributes to *Bemisia* resistance, wherein said QTL is characterized by being genetically linked to at least one marker locus, particularly to at least two marker loci, more particularly to at least three marker loci and even more particularly to at least four marker loci, but especially to at least five and up to six marker loci, which marker loci are on chromosome 3 and co-segregate with the *Bemisia* resistance trait and can be identified by a pair of PCR oligonucleotide primers selected from the group of primer pair 1 represented by a forward primer of SEQ ID NO: 1 and a reverse primer of SEQ ID NO: 2, identifying marker locus 1; primer pair 2 represented by a forward primer of SEQ ID NO: 3 and a reverse primer of SEQ ID NO: 4, identifying marker locus 2; primer pair 3 represented by a forward primer of SEQ ID NO: 5 and a reverse primer of SEQ ID NO: 6, identifying marker locus 3; primer pair 4 represented by a forward primer of SEQ ID NO: 7 and a reverse primer of SEQ ID NO: 8, identifying marker locus 4; primer pair 5 represented by a forward primer of SEQ ID NO: 9 and a reverse primer of SEQ ID NO: 10, identifying marker locus 5; and primer pair 6 represented by a forward primer of SEQ ID NO: 11 and a reverse primer of SEQ ID NO: 12, identifying marker locus 6; or by any other marker locus that is statistically correlated to the *Bemisia* resistance trait.

In one embodiment, the invention relates to a cultivated *Capsicum annuum* plant containing, a genome comprising at least one quantitative trait locus ("QTL") which contributes to *Bemisia* resistance, wherein said QTL is obtainable from a donor plant which has the genetic background of line 061M4387, particularly from a plant which has the genetic background or architecture at the QTL of line 061M4387, but especially from a plant of line 061M4387, representative seed of which is deposited at NCIMB under Accession No. NCIMB 41428, or from a progeny or an ancestor thereof comprising said QTL, which QTL in the donor plant is genetically linked to at least one marker locus, particularly to at least two marker loci, particularly to at least three marker loci and particularly to at least four marker loci, particularly to at least five marker loci, particularly to at least six marker loci, and up to seven marker loci, which marker loci are on chromosome 3 and co-segregate with the *Bemisia* resistance trait and can be identified by a pair of PCR oligonucleotide primers selected from the group of primer pairs 1 to 6 as given in SEQ ID NOs: 1 to 12.

In one embodiment, the invention relates to a cultivated *Capsicum annuum* plant according to the invention and as described herein before, which plant contains a genome comprising a quantitative trait locus ("QTL") which contributes to thrips resistance, wherein said QTL is characterized by being genetically linked to at least one marker locus, particularly to at least two marker loci, particularly to at least three marker loci and particularly to at least four marker loci, particularly to at least five marker loci, particularly to at least six marker loci, and up to seven marker loci, which marker loci are on chromosome 5 and co-segregate with the *Bemisia* resistance trait and can be identified by a pair of PCR oligonucleotide primers selected from the group of primer pair 7 represented by a forward primer of SEQ ID NO: 13 and a reverse primer of SEQ ID NO: 14, identifying marker locus 7; primer pair 8 represented by a forward primer of SEQ ID NO: 15 and a reverse primer of SEQ ID NO: 16, identifying marker locus 8; primer pair 9 represented by a forward primer of SEQ ID NO: 17 and a reverse primer of SEQ ID NO: 18, identifying marker locus 9; primer pair 10 represented by a forward primer of SEQ ID NO: 19 and a reverse primer of SEQ ID NO: 20, identifying marker locus 10; primer pair 11 represented by a forward primer of SEQ ID NO: 21 and a reverse primer of SEQ ID NO: 22, identifying marker locus 11; primer pair 12 represented by a forward primer of SEQ ID NO: 23 and a reverse primer of SEQ ID NO: 24, identifying marker locus 12, and primer pair 13 represented by a forward primer of SEQ ID NO: 25 and a reverse primer of SEQ ID NO: 26, identifying marker locus 13; or by any other marker locus that is statistically correlated to the *Bemisia* resistance trait.

In one embodiment, the invention relates to a cultivated *Capsicum annuum* plant containing a genome comprising at least one quantitative trait locus ("QTL") which contributes to *Bemisia* resistance, wherein said QTL is obtainable from a donor plant which has the genetic background of line 061M4387, particularly from a plant which has the genetic background or architecture at the QTL of line 061M4387, but especially from a plant of line 061M4387, representative seed of which is deposited at NCIMB under Accession No. NCIMB 41428, or from a progeny or an ancestor thereof comprising said QTL, which QTL in the donor plant is genetically linked to at least one marker locus, particularly to at least two marker loci, particularly to at least three marker loci and particularly to at least four marker loci, particularly to at least five marker loci, particularly to at least six marker loci, and up to seven marker loci, which marker loci are on chromosome 5 and co-segregate with the *Bemisia* resistance trait and can be identified by a pair of PCR oligonucleotide primers selected from the group of primer pairs 7 to 13 as given in SEQ ID NOs: 13 to 26.

In a further embodiment, the invention relates to a cultivated *Capsicum annuum* plant according to the invention and as described herein before, which plant contains a genome comprising at least two quantitative trait loci ("QTL") which contribute to *Bemisia* resistance, wherein a) a first QTL is characterized by being genetically linked to at least one marker locus, particularly to at least two marker loci, more particularly to at least three marker loci and even more particularly to at least four marker loci, but especially to at least five and up to six marker loci, which marker loci are on chromosome 3 and co-segregate with the *Bemisia* resistance trait and can be identified by a pair of PCR oligonucleotide primers selected from the group of primer pair 1 represented by a forward primer of SEQ ID NO: 1 and a reverse primer of SEQ ID NO: 2, identifying marker locus 1; primer pair 2 represented by a forward primer of SEQ ID NO: 3 and a reverse primer of SEQ ID NO: 4, identifying marker locus 2; primer pair 3 represented by a forward primer of SEQ ID NO: 5 and a reverse primer of SEQ ID NO: 6, identifying marker locus 3; primer pair 4 represented by a forward primer of SEQ ID NO: 7 and a reverse primer of SEQ ID NO: 8, identifying marker locus 4; primer pair 5 represented by a forward primer of SEQ ID NO: 9 and a reverse primer of SEQ ID NO: 10, identifying marker locus 5; and primer pair 6 represented by a forward primer of SEQ ID NO: 11 and a reverse primer of SEQ ID NO: 12, identifying marker locus 6; or by any other marker locus on chromosome 3 that is statistically correlated to the *Bemisia* resistance trait; and b) a second QTL is characterized by being genetically linked to at least one marker locus, particularly to at least two marker loci, particularly to at least three marker loci and particularly to at least four marker loci, particularly to at least five marker loci, particularly to at least six marker loci, and up to seven marker loci, which marker loci are on chromosome 5 and co-segregate with the *Bemisia* resistance trait and can be identified by a pair of PCR oligonucleotide primers selected from the group of primer pair 7 represented by a forward primer of SEQ ID NO: 13 and a reverse primer of SEQ ID NO: 14, identifying marker locus 7; primer pair 8 represented by a forward primer of SEQ ID NO: 15 and a reverse primer of SEQ ID NO: 16, identifying marker locus 8; primer pair 9 represented by a forward primer of SEQ ID NO: 17 and a reverse primer of SEQ ID NO: 18, identifying marker locus 9; primer pair 10 represented by a forward primer of SEQ ID NO: 19 and a reverse primer of SEQ ID NO: 20, identifying marker locus 10; primer pair 11 represented by a forward primer of SEQ ID NO: 21 and a reverse primer of SEQ ID NO: 22, identifying marker locus 11; primer pair 12 represented by a forward primer of SEQ ID NO: 23 and a reverse primer of SEQ ID NO: 24, identifying marker locus 12, and primer pair 13 represented by a forward primer of SEQ ID NO: 25 and a reverse primer of SEQ ID NO: 26, identifying marker locus 13, or by any other marker locus on chromosome 5 that is statistically correlated to the *Bemisia* resistance trait.

In one embodiment, the invention relates to a cultivated *Capsicum annuum* plant containing a genome comprising at, least two quantitative trait loci ("QTL") which contribute to *Bemisia* resistance, wherein said QTL are obtainable from a donor plant which has the genetic background of line 061M4387, particularly from a plant which has the genetic background or architecture at the QTL of line 061M4387, but especially from a plant of line 061M4387, representative seed of which is deposited at NCIMB under Accession. No. NCIMB 41428, or from a progeny or an ancestor thereof comprising said QTL, which first. QTL is located on chromosome 3 in the donor plant and genetically linked to at least one marker locus, particularly to at least two marker loci, particularly to at least three marker loci and particularly to at least four marker loci, particularly to at least five marker loci, particularly to at, least six marker loci, which marker loci are on chromosome 3 and co-segregate with the *Bemisia* resistance trait and can be identified by a pair of PCR oligonucleotide primers 1 to 6 as given in SEQ ID NOs: 1 to 12 and which second QTL is located on chromosome 5 in the donor plant and genetically linked to at least one marker locus, particularly to at least two marker loci, particularly to at least three marker loci and particularly to at least four marker loci, particularly to at least five marker loci, particularly to at least six marker loci, and up to seven marker loci, which marker loci are on chromosome 5 and co-segregate with the *Bemisia* resistance trait and can be identified by a pair of PCR oligonucleotide primers selected from the group of primer pairs 7 to 13 as given in SEQ ID NOs: 13 to 26.

In one embodiment, the invention relates to a cultivated *Capsicum annuum* plant according to the invention and as described herein before, which plant contains a genome comprising a quantitative trait locus ("QTL") which contributes to thrips resistance, wherein said QTL is characterized by being genetically linked to at least one market locus, particularly to at least two marker loci, particularly to at least three marker loci, and particularly to at least four marker loci, particularly to at least five marker loci, particularly to at least six marker loci, and up to seven marker loci, which marker loci are on chromosome 5 and co-segregate with the thrips resistance trait and can be identified by a pair of PCR oligonucleotide primers selected from the group of primer pair 7 represented by a forward primer of SEQ ID NO: 13 and a reverse primer of SEQ ID NO: 14, identifying marker locus 7; primer pair 8 represented by a forward primer of SEQ ID NO: 15 and a reverse primer of SEQ ID NO: 16, identifying marker locus 8; primer pair 9 represented by a forward primer of SEQ ID NO: 17 and a reverse primer of SEQ ID NO: 18, identifying marker locus 9; primer pair 10 represented by a forward primer of SEQ ID NO: 19 and a reverse primer of SEQ ID NO: 20, identifying marker locus 10; primer pair 11 represented by a forward primer of SEQ ID NO: 21 and a reverse primer of SEQ ID NO: 22, identifying marker locus 11; primer pair 12 represented by a forward primer of SEQ ID NO: 23 and a reverse primer of SEQ ID NO: 24, identifying marker locus 12, and primer pair 13 represented by a forward primer of SEQ ID NO: 25 and a reverse primer of SEQ ID NO: 26, identifying marker locus 13, or by any other marker locus on chromosome 5 that is statistically correlated to the thrips resistance trait.

In one embodiment, the invention relates to a cultivated *Capsicum annuum* plant containing a genome comprising at least one quantitative trait locus ("QTL") which contributes to thrips resistance, wherein said QTL is obtainable from a donor plant which has the genetic background of line 061M4387, particularly from a plant which has the genetic background or architecture at the QTL of line 061M4387, but especially from a plant of line 061M4387, representative seed of which is deposited at NUMB under Accession No. NCIMB 41428, or from a progeny or an ancestor thereof comprising said QTL, which QTL in the donor plant is genetically linked to at least one marker locus, particularly to at least two marker loci, particularly to at least three marker loci and particularly to at least four marker loci, particularly to at least five marker loci, particularly to at least six marker loci, and up to seven marker loci, which marker loci are on chromosome 5 and co-segregate with the thrips resistance trait and can be identified, by a pair of PCR oligonucleotide primers selected from the group of primer pairs 7 to 13 as given in SEQ ID NOs: 13 to 26.

In one embodiment, the present invention provides a cultivated *Capsicum annuum* plant which is resistant, particularly intermediately resistant, to *Bemisia* and thrips infestations, wherein said plant contains a genome comprising at least one quantitative trait locus ("QTL") which contributes to *Bemisia* resistance and at least one quantitative trait locus ("QTL") which contributes to thrips resistance, respectively, wherein said QTL contributing to a) *Bemisia* resistance is characterized by being genetically linked to at least one marker locus, particularly to at least two marker loci, more particularly to at least three marker loci and even more particularly to at least four marker loci, but especially to at least five and up to six marker loci, which marker loci are on chromosome 3 and co-segregate with the *Bemisia* resistance trait and can be identified by a pair of PCR oligonucleotide primers selected from the group of primer pair 1 represented by a forward primer of SEQ ID NO: 1 and a reverse primer of SEQ ID NO: 2, identifying marker locus 1; primer pair 2 represented by a forward primer of SEQ ID NO: 3 and a reverse primer of SEQ ID NO: 4, identifying marker locus 2; primer pair 3 represented by a forward primer of SEQ ID NO: 5 and a reverse primer of SEQ ID NO: 6, identifying marker locus 3; primer pair 4 represented by a forward primer of SEQ ID NO: 7 and a reverse primer of SEQ ID NO: 8, identifying marker locus 4; primer pair 5 represented by a forward primer of SEQ ID NO: 9 and a reverse primer of SEQ ID NO: 10, identifying marker locus 5; and primer pair 6 represented by a forward primer of SEQ ID NO: 11 and a reverse primer of SEQ ID NO: 12, identifying marker locus 6, or by any other marker locus on chromosome 3 that is statistically correlated to the *Bemisia* resistance trait; and b) thrips resistance is characterized by being genetically linked to at least one marker locus, particularly to at least two marker loci, particularly to at least three marker loci and particularly to at least four marker loci, particularly to at least five marker loci, particularly to at least six marker loci, and up to seven marker loci, which marker loci are on chromosome 5 and co-segregate with the thrips resistance trait and can be identified by a pair of PCR oligonucleotide primers selected from the group of primer pair 7 represented by a forward primer of SEQ ID NO: 13 and a reverse primer of SEQ ID NO: 14, identifying marker locus 7; primer pair 8 represented by a forward primer of SEQ ID NO: 15 and a reverse primer of SEQ ID NO: 16, identifying marker locus 8; primer pair 9 represented by a forward primer of SEQ ID NO: 17 and a reverse primer of SEQ ID NO: 18, identifying marker locus 9; primer pair 10 represented by a forward primer of SEQ ID NO: 19 and a reverse primer of SEQ ID NO: 20, identifying marker locus 10; primer pair 11 represented by a forward primer of SEQ ID NO: 21 and a reverse primer of SEQ ID NO: 22, identifying marker focus 11; primer pair 12 represented by a forward primer of SEQ ID NO: 23 and a reverse primer of SEQ ID NO: 24, identifying marker locus 12, and primer pair 13 represented by a forward primer of SEQ ID NO: 25 and a reverse primer of SEQ ID NO: 26, identifying marker locus 13, or by any other marker locus on chromosome 5 that is statistically correlated to the thrips resistance trait.

In one embodiment, the present invention provides a cultivated *Capsicum annuum* plant according to any of the preceding claims, which is resistant, particularly intermediately resistant, to *Bemisia* and thrips infestations, wherein said plant contains a genome comprising at least one quantitative trait locus ("QTL") which contributes to *Bemisia* resistance and at least one quantitative trait locus ("QTL") which contributes to thrips resistance, respectively, wherein said QTL contributing to a) *Bemisia* resistance is characterized, by being genetically linked to
   i. at least one marker locus, particularly to at least two marker loci, more particularly to at least three marker loci and even more particularly to at least four marker loci, but especially to at least five and up to six marker loci, which marker loci are on chromosome 3 and co-segregate with the *Bemisia* resistance trait and can be identified by a pair of PCR oligonucleotide primers selected from the group of primer pair 1 represented by a forward primer of SEQ ID NO: 1 and a reverse primer of SEQ ID NO: 2, identifying marker locus 1; primer pair 2 represented by a forward primer of SEQ ID NO: 3 and a reverse primer of SEQ ID NO: 4, identifying marker locus 2; primer pair 3 represented by a forward primer of SEQ ID NO: 5 and a reverse primer of SEQ ID NO: 6, identifying marker locus 3; primer pair 4 represented by a forward primer of SEQ ID NO: 7 and a reverse primer of SEQ ID NO: 8, identifying marker locus 4; primer pair 5 represented by a forward primer of SEQ ID NO: 9 and a reverse primer of SEQ ID NO: 10, identifying marker locus 5; and primer pair 6 represented by a forward primer of SEQ ID NO: 11 and a reverse primer of SEQ ID NO: 12, identifying marker locus 6, or by any other marker locus on chromosome 3 that is statistically correlated to the *Bemisia* resistance trait; and/or
   ii. at least one marker locus, particularly to at least two marker loci, particularly to at least three marker loci and particularly to at least four marker loci, particularly to at least five marker loci, particularly to at least six marker loci, and up to seven marker loci, which marker loci are on chromosome 5 and co-segregate with the thrips resistance trait and can be identified by a pair of PCR oligonucleotide primers selected from the group of primer pair 7 represented by a forward primer of SEQ ID NO: 13 and a reverse primer of SEQ ID NO: 14, identifying marker locus 7; primer pair 8 represented by a forward primer of SEQ ID NO: 15 and a reverse primer of SEQ ID NO: 16, identifying marker locus 8; primer pair 9 represented by a forward primer of SEQ ID NO: 17 and a reverse primer of SEQ ID NO: 18, identifying marker locus 9; primer pair 10 represented by a forward primer of SEQ ID NO: 19 and a reverse primer of SEQ ID NO: 20, identifying marker locus 10; primer pair 11 represented by a forward primer of SEQ ID NO: 21 and a reverse primer of SEQ ID NO: 22, identifying marker locus 11; primer pair 12 represented by a forward primer of SEQ ID NO: 23 and a reverse primer of SEQ ID NO: 24, identifying marker locus 12, and primer pair 13 represented by a forward primer of SEQ ID NO: 25 and a reverse primer of SEQ ID NO: 26, identifying marker locus 13, or by any other marker locus on chromosome 5 that is statistically correlated to the *Bemisia* resistance trait; and b) thrips resistance is characterized by being genetically linked to at least one marker locus, particularly to at least two marker loci, particularly to at least three marker loci and particularly to at least four marker loci, particularly to at least five marker loci, particularly to at least six marker loci, and up to seven marker loci, which marker loci are on chromosome 5 and co-segregate with the thrips resistance trait and can be identified by a pair of PCR oligonucleotide primers selected from the group of primer pair 7 represented by a forward primer of SEQ ID NO: 13 and a reverse primer of SEQ ID NO: 14, identifying marker locus 7; primer pair 8 represented by a forward primer of SEQ ID NO: 15 and a reverse primer of SEQ ID NO: 16, identifying marker locus 8; primer pair 9 represented by a forward primer of SEQ ID NO: 17 and a reverse primer of SEQ ID NO: 18, identifying marker locus 9; primer pair 10 represented by a forward primer of SEQ ID NO: 19 and a reverse primer of SEQ ID NO: 20, identifying marker locus 10; primer pair 11 represented by a forward primer of SEQ ID NO: 21 and a reverse primer of SEQ ID NO: 22, identifying marker locus 11; primer pair 12 represented by a forward primer of SEQ ID NO: 23 and a reverse primer of SEQ ID NO: 24, identifying marker locus 12, and primer pair 13 represented by a forward primer of SEQ ID NO: 25 and a reverse primer of SEQ ID NO: 26, identifying marker locus 13, or by any other marker locus on chromosome 5 that is statistically correlated to the thrips resistance trait.

In one embodiment, the present invention provides a cultivated *Capsicum annuum* plant which is resistant, particularly intermediately resistant, to *Bemisia* and thrips infestations, wherein said plant contains a genome comprising at least one quantitative trait locus ("QTL") which contributes to *Bemisia* resistance and at least one quantitative trait locus ("QTL") which contributes to thrips resistance, respectively, wherein said QTL are obtainable from a donor plant which has the genetic background of line 061M4387, particularly from a plant which has the genetic background or architecture at the QTL of line 061M4387, but especially from a plant of line 061M4387, representative seed of which is deposited at NCIMB under Accession No. NCIMB 41428, or from a progeny or an ancestor thereof comprising said QTL, and wherein a) a first QTL contributing to *Bemisia* resistance is genetically linked in the donor plant to at least one marker locus, particularly to at least two marker loci, more particularly to at least three marker loci and even more particularly to at least four marker loci, but especially to at least five and up to six marker loci, which marker loci are on chromosome 3 and co-segregate with the *Bemisia* resistance trait and can be identified by a pair of PCR oligonucleotide primers selected from the group of primer pairs 1 to 6 represented by a forward and a reverse primer as given in SEQ ID NOs: 1 to 12; and/or b) a second QTL contributing to *Bemisia* resistance is genetically linked in the donor plant to at least one marker locus, particularly to at least two marker loci, particularly to at least three marker loci and particularly to at least four marker loci, particularly to at least five marker loci, particularly to at least six marker loci, and up to seven marker loci, which marker loci are on chromosome 5 and co-segregate with the *Bemisia* resistance trait and can be identified by a pair of PCR oligonucleotide primers selected from the group of primer pairs 7 to 13 represented by a forward and a reverse primer as given in SEQ ID NOs: 13 to 26; and, c) a QTL contributing to thrips resistance is genetically linked in the donor plant to at least one marker locus, particularly to at least two marker loci, particularly to at least three marker loci and particularly to at least four marker loci, particularly to at least five marker loci, particularly to at least six marker loci, and up to seven marker loci, which marker loci are on chromosome 5 and co-segregate with the thrips resistance trait and can be identified by a pair of PCR oligonucleotide primers selected from the group of primer pairs 7 to 13 represented by a forward and a reverse primer as given in SEQ ID NOs: 13 to 26.

In one embodiment, the present invention provides a cultivated *Capsicum annuum* plant which is resistant, particularly intermediately resistant, to *Bemisia* and thrips infestations, wherein said plant contains a genome comprising at least one quantitative trait locus ("QTL") which contributes to *Bemisia* resistance and at least one quantitative trait locus ("QTL") which contributes to thrips resistance, respectively, wherein said QTL are obtainable from a donor plant which has the genetic background of line 061M4387, particularly from a plant which has the genetic background or architecture at the QTL of line 061M4387, but especially from a plant of line 061M4387, representative seed of which is deposited at NCIMB under Accession No. NCIMB 41428, or from a progeny or an ancestor thereof comprising said QTL, and wherein said QTL contributing to a) *Bemisia* resistance in the donor plant is genetically linked to at least one marker locus, particularly to at least two marker loci, more particularly to at least three marker loci and even more particularly to at least four marker loci, but especially to at least five and up to six marker loci, which marker loci are on chromosome 3 and co-segregate with the *Bemisia* resistance trait and can be identified by a pair of PCR oligonucleotide primers selected from the group of primer pairs 1 to 6 represented by a forward and a reverse primer as given in SEQ ID NOs: 1 to 12; and b) thrips resistance in the donor plant is genetically linked to at least one marker locus, particularly to at least two marker loci, particularly to at least three marker loci and particularly to at least four marker loci, particularly to at least five marker loci, particularly to at least six marker loci, and up to seven marker loci, which marker loci are on chromosome 5 and co-segregate with the thrips resistance trait and can be identified by a pair of PCR oligonucleotide primers selected from the group of primer pairs 7 to 13 represented by a forward and a reverse primer as given in SEQ ID NOs: 13 to 26.

In one embodiment of the invention, one or more primers or probes, particularly one or more primer pairs, but especially one or more primer pairs consisting of a forward primer and a reverse primer, may be established for identifying the marker loci according to the invention by using said one or more primers or probes or said one or more primer pairs, particularly by combining the forward and reverse primers of SEQ ID NOs: 1-12 to result in a primer pair allowing to identify one or more of the marker loci on chromosome 3, which co-segregate with the *Bemisia* resistance trait.

In one embodiment of the invention, one or more primers or probes, particularly one or more primer pairs, but especially one or more primer pairs consisting of a forward primer and a reverse primer, may be established for identifying the marker loci according to the invention by using said one or more primers or probes or said one or more primer pairs, particularly by combining the forward and reverse primers of SEQ ID NOs: 13-26 to result in a primer pair allowing to identify one or more of the marker loci on chromosome 5, which co-segregate with the thrips and/or *Bemisia* resistance trait.

Also comprised by the present invention are primers and/or probes, particularly primer pairs, but especially primer pairs consisting of forward and reverse primers exhibiting a nucleotide sequence which is at least 90%, at least 95%, at least 96%, at least 97%, at least 98%, or at least 99% identical to that given in SEQ ID NOs: 1-12 and in SEQ ID NOs: 13-26, respectively, and also the primer pairs resulting from a combination of said forward and reverse primers.

In particular, the *Bemisia* resistance trait according to the invention residing on chromosome 3 can be identified by a pair of PCR oligonucleotide primers selected from the group of primer pair 1 represented by a forward primer which has at least 90%, particularly at least 95%, particularly at least 96%, particularly at least 97%, particularly at least 98%, particularly at least 99% sequence identity with the sequence depicted in SEQ ID NO: 1 and a reverse primer which has at least 90%, particularly at least 95%, particularly at least 96%, particularly at least 97%, particularly at least 98%, particularly at least 99% sequence identity with the sequence depicted in SEQ ID NO: 2 identifying marker locus 1; primer pair 2 represented by a forward primer which has at least 90%, particularly at least 95%, particularly at least 96%, particularly at least 97%, particularly at least 98%, particularly at least 99% sequence identity with the sequence depicted in SEQ ID NO: 3 and a reverse primer which has at least 90%, particularly at least 95%, particularly at least 96%, particularly at least 97%, particularly at least 98%, particularly at least 99% sequence identity with the sequence depicted in SEQ ID NO: 4 identifying marker locus 2; primer pair 3 represented by a forward primer which has at least 90%, particularly at least 95%, particularly at least 96%, particularly at least 97%, particularly at least 98%, particularly at least 99% sequence identity with the sequence depicted in SEQ ID NO: 5 and a reverse primer which has at least 90%, particularly at least 95%, particularly at least 96%, particularly at least 97%, particularly at least 98%, particularly at least 99% sequence identity with the sequence depicted in SEQ ID NO: 6 identifying marker locus 3; primer pair 4 represented by a forward primer which has at least 90%, particularly at least 95%, particularly at least 96%, particularly at least 97%, particularly at least 98%, particularly at least 99% sequence identity with the sequence depicted in SEQ ID NO: 7 and a reverse primer which has at least 90%, particularly at least 95%, particularly at least 96%, particularly at least 97%, particularly at least 98%, particularly at least 99% sequence identity with the sequence depicted in SEQ ID NO: 8 identifying marker locus 4; primer pair 5 represented by a forward primer which has at least 90%, particularly at least 95%, particularly at least 96%, particularly at least 97%, particularly at least 98%, particularly at, least 99% sequence identity with the sequence depicted in SEQ ID NO: 9 and a reverse primer which has at least 90%, particularly at least 95%, particularly at least 96%, particularly at least 97%, particularly at least 98%, particularly at least 99% sequence identity with the sequence depicted in SEQ ID NO: 10 identifying marker locus 5; and primer pair 6 represented by a forward primer which has at least 90%, particularly at least 95%, particularly at least 96%, particularly at least 97%, particularly at least 98%, particularly at least 99% sequence identity with the sequence depicted in SEQ ID NO: 11 and a reverse primer which has at least 90%, particularly at least 95%, particularly at least 96%, particularly at least 97%, particularly at least 98%, particularly at least 99% sequence identity with the sequence depicted in SEQ ID NO: 12 identifying marker locus 6, or by any other primer or primer pair that identifies a marker locus on chromosome 3 that is statistically correlated to the *Bemisia* resistance trait.

In one embodiment, the thrips resistance trait and/or the *Bemisia* resistance trait according to the invention residing on chromosome 5, can, be identified by a pair of PCR oligonucleotide primers selected from the group of primer pair 7 represented by a forward primer which has at least 90%, particularly at least 95%, particularly at least 96%, particularly at least 97%, particularly at least 98%, particularly at least 99% sequence identity with the sequence depicted in SEQ ID NO: 13 and a reverse primer which has at least 90%, particularly at least 95%, particularly at least 96%, particularly at least 97%, particularly at least 98%, particularly at least 99% sequence identity with the sequence depicted in SEQ ID NO: 14, identifying marker locus 7; primer pair 8 represented by a forward primer which has at least 90%, particularly at least 95%, particularly at least 96%, particularly at least 97%, particularly at least 98%, particularly at least 99% sequence identity with the sequence depicted in SEQ ID NO: 15 and a reverse primer which has at least 90%, particularly at least 95%, particularly at least 96%, particularly at least 97%, particularly at least 98%, particularly at least 99% sequence identity with the sequence depicted in SEQ ID NO: 16, identifying marker locus 8; primer pair 9 represented by a forward primer which has at least 95%, particularly at least 96%, particularly at least 97%, particularly at least 98%, particularly at least 99% sequence identity with the sequence depicted in SEQ ID NO: 17 and a reverse primer which has at least 95%, particularly at least 96%, particularly at least 97%, particularly at least 98%, particularly at least 99% sequence identity with the sequence depicted in SEQ ID NO: 18, identifying, marker locus 9; primer pair 10 represented by a forward primer which has at least 90%, particularly at least 95%, particularly at least 96%, particularly at least 97%, particularly at least 98%, particularly at least 99% sequence identity with the sequence depicted in SEQ ID NO: 19 and a reverse primer which has at least 90%, particularly at least 95%, particularly at least 96%, particularly at least 97%, particularly at least 98%, particularly at least 99% sequence identity with the sequence depicted in SEQ ID NO: 20, identifying marker locus 10; primer pair 11 represented by a forward primer which has at least 90%, particularly at least 95%, particularly at least 96%, particularly at least 97%, particularly at least 98%, particularly at least 99% sequence identity with the sequence depicted in SEQ ID NO: 21 and a reverse primer which has at least 90%, particularly at least 95%, particularly at least 96%, particularly at least 97%, particularly at least 98%, particularly at least 99% sequence identity with the sequence depicted in SEQ ID NO: 22, identifying marker locus 11; primer pair 12 represented by a forward primer which has at least 90%, particularly at least 95%, particularly at least 96%, particularly at least 97%, particularly at least 98%, particularly at least 99% sequence identity with the sequence depicted in SEQ ID NO: 23 and a reverse primer which has at least 90%, particularly at least 95%, particularly at least 96%, particularly at least 97%, particularly at least 98%, particularly at, least 99% sequence identity with the sequence depicted in SEQ ID NO: 24, identifying marker locus 12, and primer pair 13 represented by a forward primer which has at least 90%, particularly at least 95%, particularly at least 96%, particularly at least 97%, particularly at least 98%, particularly 99% sequence identity with the sequence depicted in SEQ ID NO: 25 and a reverse primer which has at least 90%, particularly at least 95%, particularly at least 96%, particularly at least 97%, particularly at least 98%, particularly at least 99% sequence identity with the sequence depicted in SEQ ID NO: 26, identifying marker locus 13; or by any other primer or primer pair that identifies a marker locus on chromosome 5 that is statistically correlated to the thrips and/or Bemisia resistance trait.

In one embodiment of the invention oligonucleotide primers are embraced, particularly primer pairs, but especially primer pairs consisting of a forward and a reverse primer exhibiting a nucleotide sequence that hybridizes to the nucleotide sequences of the forward and reverse primer sequences given in SEQ ID NOs: 1-12 shown in Table 10 and to the nucleotide sequences of the forward and reverse primer sequences given in SEQ ID NOs: 13-26 shown in Table 11, respectively, under medium, particularly under medium to high, particularly under high stringency conditions.

In one embodiment, the invention, relates, to oligonucleotide sequences, particularly to oligonucleotide sequences that may be used as primers and/or probes, particularly to primer pairs, but especially to primer pairs consisting of a forward and a reverse primer exhibiting a nucleotide sequence that hybridizes to nucleotide sequences obtainable by using a forward and a reverse primer exhibiting a nucleotide sequence that hybridizes to the nucleotide sequences of the forward and reverse primer sequences given in SEQ ID NOs: 1-12 shown in Table 10 and to the nucleotide sequences of the forward and reverse primer sequences given in SEQ ID NOs: 13-26 shown in Table 11, respectively, under medium, particularly under medium to high, particularly under high stringency conditions.

In another embodiment of the invention, a cultivated Capsicum annuum plant is provided as described herein before, wherein said plant comprises a quantitative trait locus ("QTL") associated with resistance to Bemisia, which QTL is characterized by being genetically linked to at least one marker locus, particularly a marker locus on chromosome 3, and wherein said QTL is further defined by at least one marker allele at said at least one marker locus, linked to the QTL, which marker allele is characterized by the PCR amplification product of an oligonucleotide primer or primer pair selected from the group of primer pairs 1-6 represented by forward and reverse primers of SEQ ID NOs: 1-12, including primer pairs resulting from a combination of the forward and reverse primers of SEQ ID NOs: 1-12, or of any other primer or primer pair that identifies a marker locus on chromosome 3 that is statistically correlated to the Bemisia resistance trait, which amplification product corresponds to an amplification product obtainable from inbred line 061M4387 (NCIMB 41428) in a PCR reaction with identical primers obtainable from said primer pairs 1-6 provided that the respective marker locus is still present in said Capsicum plant.

In particular, the cultivated Capsicum annuum plant as described herein before comprises a quantitative trait locus ("QTL") associated with resistance to Bemisia, which QTL is characterized by being genetically linked to at least one marker locus, particularly a marker locus on chromosome 3, and wherein said QTL is further defined by at least one marker allele at said at least one marker locus linked to the QTL, which marker allele is characterized by the PCR amplification product of an oligonucleotide primer pair selected from the group of primer pair 1 represented by a forward primer of SEQ ID NO: 1 and a reverse primer of SEQ ID NO: 2, identifying marker locus 1; primer pair 2 represented by a forward primer of SEQ ID NO: 3 and a reverse primer of SEQ ID NO: 4, identifying marker locus 2; primer pair 3 represented by a forward primer of SEQ ID NO: 5 and a reverse primer of SEQ ID NO: 6, identifying marker locus 3; primer pair 4 represented by a forward primer of SEQ ID NO: 7 and a reverse primer of SEQ ID NO: 8, identifying marker locus 4; primer pair 5 represented by a forward primer of SEQ ID NO: 9 and a reverse primer of SEQ ID NO: 10, identifying marker locus 5; and primer pair 6 represented by a forward primer of SEQ ID NO: 11 and a reverse primer of SEQ ID NO: 12, identifying marker locus 6, which amplification product corresponds to an amplification product obtainable from inbred line 061M4387 (NCIMB 41428) in a PCR reaction with primer pairs 1-6 identified above provided that the respective marker locus is still present in said Capsicum plant and/or can be considered an allele thereof.

In another embodiment of the invention, a cultivated Capsicum annuum plant is provided as described herein before, wherein said plant comprises a quantitative trait locus ("QTL") associated with resistance to Bemisia, which QTL is characterized by being genetically linked to at least one marker locus, particularly a marker locus on chromosome 5, and wherein said QTL is further defined by at least one marker allele at said at least one marker locus linked to the QTL, which marker allele is characterized by the PCR amplification product of an oligonucleotide primer or primer pair selected from the group of primer pairs 7-13 represented by forward and reverse primers of SEQ ID NOs: 13-26, including primer pairs resulting from a combination of the forward and reverse primers of SEQ ID NOs: 13-26, or of any other primer or primer pair that identifies a marker locus on chromosome 5 that is statistically correlated to the Bemisia resistance trait, which amplification product corresponds to an amplification product obtainable from inbred line 061M4387 (NCIMB 41428) in a PCR reaction with identical primers obtainable from primer pairs 7-13 identified above provided that the respective marker locus is still present in said Capsicum plant and/or can be considered an allele thereof.

In particular, the cultivated Capsicum annuum plant as described herein before comprises a quantitative trait locus ("QTL") associated with resistance to Bemisia, which QTL is characterized by being genetically linked to at least one marker locus, particularly a marker locus on chromosome 5, and wherein said QTL is further defined by at least one marker allele at said at least one marker locus linked to the QTL, which marker allele is characterized by the PCR amplification product of an oligonucleotide primer pair selected from the group of primer pair 7 represented by a forward primer of SEQ ID NO: 13 and a reverse primer of SEQ ID NO: 14, identifying marker locus 7; primer pair 8, represented by a forward primer of SEQ ID NO: 15 and a reverse primer of SEQ ID NO: 16, identifying marker locus 8; primer pair 9 represented by a forward primer of SEQ ID NO: 17 and a reverse primer of SEQ ID NO: 18, identifying marker locus 9; primer pair 10 represented by a forward primer of SEQ ID NO: 19 and a reverse primer of SEQ ID NO: 20, identifying marker locus 10; primer pair 11 represented by a forward primer of SEQ ID NO: 21 and a reverse primer of SEQ ID NO: 22, identifying marker locus 11; primer pair 12 represented by a forward primer of SEQ ID NO: 23 and a reverse primer of SEQ ID NO: 24, identifying marker locus 12, and primer pair 13 represented by a forward primer of SEQ ID NO: 25 and a reverse primer of SEQ ID NO: 26, identifying marker locus 13, which amplification product corresponds to an amplification product obtainable from inbred line 061M4387 (NCIMB 41428) in a PCR reaction with identical primers obtainable from primer pairs 7-13 identified above provided that the respective marker locus is still present in said *Capsicum* plant and/or can be considered an allele thereof.

In another embodiment of the invention, a cultivated *Capsicum annuum* plant is provided as described herein before, wherein said plant comprises a quantitative trait locus ("QTL") associated with resistance to thrips, which QTL is characterized by being genetically linked to at least one marker locus, particularly a marker locus on chromosome 5, and wherein said QTL is further defined by at least one marker allele at said at least one marker locus linked to the QTL, which marker allele is characterized by the PCR amplification product of an oligonucleotide primer or primer pair selected from the group of primer pairs 7-13 represented by forward and reverse primers of SEQ ID NOs: 13-26, including primer pairs resulting from a combination of the forward and reverse primers of SEQ ID NOs: 13-26, or of any other primer or primer pair that identifies a marker locus on chromosome 5 that is statistically correlated to the thrips resistance trait, which amplification product corresponds to an amplification product obtainable from inbred line 061M4387 (NCIMB 41428) in a PCR reaction with identical primers obtainable from primer pairs 7-13 identified above provided that the respective marker locus is still present in said *Capsicum* plant and/or can be considered an allele thereof.

In particular, the cultivated *Capsicum annuum* plant as described herein before comprises a quantitative trait locus ("QTL") associated with resistance to thrips, which QTL is characterized by being genetically linked to at least one marker locus, particularly a marker locus on chromosome 5, and wherein said QTL is further defined by at least one marker allele at said at least one marker locus linked to the QTL, which marker allele is characterized by the PCR amplification product of an oligonucleotide primer or primer pair selected from the group of primer pair 7 represented by a forward primer of SEQ ID NO: 13 and a reverse primer of SEQ ID NO: 14, identifying marker locus 7; primer pair 8 represented by a forward primer of SEQ ID NO: 15 and a reverse primer of SEQ ID NO: 16, identifying marker locus 8; primer pair 9 represented by a forward primer of SEQ ID NO: 17 and a reverse primer of SEQ ID NO: 18, identifying marker locus 9; primer pair 10 represented by a forward primer of SEQ ID NO: 19 and a reverse primer of SEQ ID NO: 20, identifying marker locus 10; primer pair 11 represented by a forward primer of SEQ ID NO: 21 and a reverse primer of SEQ ID NO: 22, identifying marker locus 11; primer pair 12 represented by a forward primer of SEQ ID NO: 23 and a reverse primer of SEQ ID NO: 24, identifying marker locus 12, and primer pair 13 represented by a forward primer of SEQ ID NO: 25 and a reverse primer of SEQ ID NO: 26, identifying marker locus 13, which amplification product corresponds to an amplification product obtainable from inbred line 061M4387 (NCIMB 41428) in a PCR reaction with identical primers obtainable from primer pairs 7-13 identified above provided that the respective marker locus is still present in said *Capsicum* plant and/or can be considered an allele thereof.

In one embodiment of the invention, a cultivated *Capsicum annuum* plant is provided as described herein before, wherein said plant comprises at least one quantitative trait locus ("QTL") associated with resistance to *Bemisia* and one quantitative trait locus ("QTL") associated with resistance to thrips, respectively, which QTL are characterized by being genetically linked to at least one marker locus each, particularly a marker locus on chromosome 3 and chromosome 5, respectively, and wherein said QTL are further defined by at least one marker allele at said at least one marker locus linked to a) a first QTL on chromosome 3, which marker allele is characterized by the PCR amplification product of an oligonucleotide primer or primer pair selected from the group of primer pairs 1-6 represented by forward and reverse primers of SEQ ID NOs: 1-12, or of any other primer or primer pair that identifies a marker locus on chromosome 3 that is statistically correlated to the *Bemisia* resistance trait, and b) a second QTL on chromosome 5, which marker allele is characterized by the PCR amplification product of oligonucleotide primer or primer pair selected from the group of primer pairs 7-13 represented by forward and reverse primers of SEQ ID NOs: 13-26, respectively, or of any other primer or primer pair that identifies a marker locus on chromosome 5 that is statistically correlated to the *Bemisia* and/or thrips resistance trait, including primer pairs resulting from a combination of the forward and reverse primers of SEQ ID NOs: 1-12 and from a combination of the forward and reverse primers of SEQ ID NOs: 13-26, respectively, which amplification product corresponds to an amplification product obtainable from inbred line 061M4387 (NCIMB 41428) in a PCR reaction with identical primers obtainable from said primer pairs 1-6 and 7-13, respectively, provided that the respective marker locus is still present in said *Capsicum* plant and/or can be considered an allele thereof.

In particular, the cultivated *Capsicum annuum* plant as described herein before comprises a quantitative trait locus ("QTL") associated a) with resistance to *Bemisia*, which QTL is characterized by being genetically linked to at least one marker locus, particularly a marker locus on chromosome 3, and wherein said QTL is further defined by at least one marker allele at said at least one marker locus linked to the QTL, which marker allele is characterized by the PCR amplification product of an oligonucleotide primer pair selected from the group of primer pair 1 represented by a forward primer of SEQ ID NO: 1 and a reverse primer of SEQ ID NO: 2, identifying marker locus 1; primer pair 2 represented by a forward primer of SEQ ID NO: 3 and a reverse primer of SEQ ID NO: 4, identifying marker locus 2; primer pair 3 represented by a forward primer of SEQ ID NO: 5 and a reverse primer of SEQ ID NO: 6, identifying marker locus 3; primer pair 4 represented by a forward primer of SEQ ID NO: 7 and a reverse primer of SEQ ID NO: 8, identifying marker locus 4; primer pair 5 represented by a forward primer of SEQ ID NO: 9 and a reverse primer of SEQ ID NO: 10, identifying marker locus 5; and primer pair 6 represented by a forward primer of SEQ ID NO: 11 and a reverse primer of SEQ ID NO: 12, identifying marker locus 6, or by any other marker locus on chromosome 3 that is statistically correlated to the *Bemisia* resistance trait; and b) with resistance to thrips and/or *Bemisia*, which QTL is characterized by being genetically linked to at least one marker locus, particularly a marker locus, on chromosome 5, and wherein said QTL is further defined by at least one marker allele at said at least one marker locus linked to the QTL, which marker allele is characterized by the PCR amplification product of an oligonucleotide primer pair selected from the group of primer pair 7 represented by a forward primer of SEQ ID NO: 13 and a reverse primer of SEQ ID NO: 14, identifying marker locus 7; primer pair 8 represented by a forward primer of SEQ ID NO: 15 and a reverse primer of SEQ ID NO: 16, identifying marker locus 8; primer pair 9 represented by a forward primer of SEQ ID NO: 17 and a reverse primer of SEQ ID NO: 18, identifying marker locus 9; primer pair 10 represented by a forward primer of SEQ ID NO: 19 and a reverse primer of SEQ ID NO: 20, identifying marker locus 10; primer pair 11 represented by a forward primer of SEQ ID NO: 21 and a reverse primer of SEQ ID NO: 22, identifying marker locus 11; primer pair 12 represented by a forward primer of SEQ ID NO: 23 and a reverse primer of SEQ ID NO: 24, identifying marker locus 12, and primer pair 13 represented by a forward primer of SEQ ID NO: 25 and a reverse primer of SEQ ID NO: 26, identifying marker locus 13, or by any other marker locus on chromosome 5 that is statistically correlated to the thrips and/or *Bemisia* resistance trait, wherein each amplification product corresponds to an amplification product obtainable from inbred line 061M4387 (NCIMB 41428) in a PCR reaction with identical primers obtainable from primer pairs 1-6 and 7-13, respectively, identified above provided that the respective marker locus is still present in said *Capsicum* plant and/or can be considered an allele thereof.

In one embodiment, the invention relates to the amplification product obtainable in a PCR reaction involving an oligonucleotide primer or primer pair selected from the group of primer pairs 1-6 represented by forward and reverse primers of SEQ ID NOs: 1-12 and primer pairs 7-13 represented by forward and reverse primers of SEQ ID NOs: 13-26, respectively, including primer pairs resulting from a combination of the forward and reverse primers of SEQ ID NOs: 1-12 and SEQ ID NOs: 13-26, respectively, or any other primer or primer pair that identifies a marker locus on chromosome 3 and/or chromosome 5 that is statistically correlated to the *Bemisia* and/or thrips resistance trait, which amplification product corresponds to an amplification product obtainable from inbred line 061M4387 (NCIMB 41428) in a PCR, reaction with identical primers obtainable from said primer pairs 1-6 and 7-13, respectively, or combination of primer pairs provided that the respective marker locus is still present in said *Capsicum* plant and/or can be considered an allele thereof.

Also included is a polynucleotide that has at least 90%, particularly at least 95%, particularly at least 96%, particularly at least 97%, particularly at least, 98%, particularly at least 99% sequence identity with the sequence of said amplification product.

In one embodiment of the invention a polynucleotide is embraced exhibiting a nucleotide sequence that hybridizes to the nucleotide sequences of an amplification product obtainable in a PCR reaction involving an oligonucleotide primer pair selected from the group of primer pairs 1-6 represented by forward and reverse primers of SEQ ID NOs: 1-12 and primer pairs 7-13 represented by forward and reverse primers of SEQ ID NOs: 13-26, respectively, including primer pairs resulting from a combination of the forward and reverse primers of SEQ ID NOs: 1-12 and SEQ ID NOs: 13-26, respectively.

In a specific embodiment, the invention relates to the amplification product obtainable in a PCR reaction involving an oligonucleotide primer pair selected from the group of primer pair 1 represented by a forward primer of SEQ ID NO: 1 and a reverse primer of SEQ ID NO: 2, identifying marker locus 1; primer pair 2 represented by a forward primer of SEQ ID NO: 3 and a reverse primer of SEQ ID NO: 4, identifying marker locus 2; primer pair 3 represented by a forward primer of SEQ ID NO: 5 and a reverse primer of SEQ ID NO: 6, identifying marker locus 3; primer pair 4 represented by a forward primer of SEQ ID NO: 7 and a reverse primer of SEQ ID NO: 8, identifying marker locus 4; primer pair 5 represented by a forward primer of SEQ ID NO: 9 and a reverse primer of SEQ ID NO: 10, identifying marker locus 5; and primer pair 6 represented by a forward primer of SEQ ID NO: 11 and a reverse primer of SEQ ID NO: 12, identifying marker locus 6, which amplification product corresponds to an amplification product obtainable from inbred line 061M4387 (NCIMB 41428) in a PCR reaction with identical primers obtainable from said primer pairs 1-6 identified above provided that the respective marker locus is still present in said *Capsicum* plant.

In another specific embodiment, the invention relates to the amplification product obtainable in a PCR reaction involving an oligonucleotide primer pair selected from the group of primer pair 7 represented by a forward primer of SEQ ID NO: 13 and a reverse primer of SEQ ID NO: 14, identifying marker locus 7; primer pair 8 represented by a forward primer of SEQ ID NO: 15 and a reverse primer of SEQ ID NO: 16, identifying marker locus 8; primer pair 9 represented by a forward primer of SEQ ID NO: 17 and a reverse primer of SEQ ID NO: 18, identifying marker locus 9; primer pair 10 represented by a forward primer of SEQ ID NO: 19 and a reverse primer of SEQ ID NO: 20, identifying marker locus 10; primer pair 11 represented by a forward primer of SEQ ID NO: 21 and a reverse primer of SEQ ID NO: 22, identifying marker locus 11; primer pair 12 represented by a forward primer of SEQ ID NO: 23 and a reverse primer of SEQ ID NO: 24, identifying marker locus 12, and primer pair 13 represented by a forward primer of SEQ ID NO: 25 and a reverse primer of SEQ ID NO: 26, identifying marker locus 13, which amplification product corresponds to an amplification product obtainable from inbred line 061M4387 (NCIMB 41428) in a PCR reaction with identical primers obtainable from said primer pairs 7-13 identified above provided that the respective marker locus is still present in said *Capsicum* plant.

The amplification product according to the invention and described herein above can then be used for generating new primers or probes that can be used for identifying a marker locus, particularly a marker locus on chromosome 3 and/or 5, respectively, genetically linked with a QTL associated with resistance to *Bemisia* and/or thrips.

In one embodiment the invention relates to a marker, particularly to primers or probes developed from an amplification product according to the invention and as described herein above by methods known in the art.

In one embodiment of the invention, a cultivated *Capsicum annuum* plant according to the invention and as described herein before is provided, wherein said allele or alleles associated with resistance to *Bemisia* is obtainable from line 061M4387, or any other line having the same genetic architecture at the QTL on chromosome 3 and/or chromosome 5, representative seed of which is deposited under Accession No. NCIMB 41428, or from a progeny or an ancestor thereof comprising said QTL, or QTL architecture.

This would also cover plants where the markers specifically disclosed herein are recombined off and thus no longer present in plant genome.

In one embodiment of the invention, a cultivated *Capsicum annuum* plant according to the invention and as described herein before is provided, wherein said allele associated with resistance to thrips is obtainable from line 061M4387, or any other line having the same genetic architecture at the QTL on chromosome 5, representative seed of which is deposited under Accession No. NCIMB 41428, or from a progeny or an ancestor thereof comprising said QTL, or QTL architecture.

This would also cover plants where the markers specifically disclosed herein are recombined off and thus no longer present in plant genome.

In one aspect of the invention, the cultivated *Capsicum annuum* plant according to the invention and as described herein before is heterozygous for the *Bemisia* and/or thrips resistance trait.

In one aspect of the invention, the cultivated *Capsicum annuum* plant according to the invention and as described herein before is homozygous for the *Bemisia* and/or thrips resistance trait.

In one aspect of the invention, the cultivated *Capsicum annuum* plant according to the invention and as described herein before is homozygous for a c locus (Blum et al. (2002) Genome, 45: 702-705) or a pun1 allele (Stewart et al., (2005) The Plant Journal, 42: 675-688) or for both a c locus and a pun1 allele.

In still another aspect of the invention, the plant according to the invention and as described herein before carries fruit, which, at maturity, weigh over 2 grams or are longer than 1 cm and have a diameter of over 0.5 cm and do not show feeding damage caused by thrips and/or *Bemisia*, when said plant is grown under growing conditions generally used by growers in regular cropping practice, in open field or in greenhouse.

The plant according to the invention and as described herein before may be a sweet pepper plant, a bell pepper, a big rectangular pepper, a conical pepper, a long conical pepper or a blocky-type pepper. The fruit of said plant may be an evergreen, a yellow, orange, ivory or red fruit.

The plant according to the invention may be a hot pepper plant, e.g. a mildly pungent pepper used for the fresh market and for processing including the long, heart-shaped, thin-fleshed Ancho-type and the long, blunt-ended, thin-fleshed Tuscan-type pepper, the slightly more pungent Chili pepper fruit with medium flesh thickness, and a pungent pepper used in both the fresh market and for processing including the long, cylindrical-thick fleshed Jalapeno, the small, slender, tapering Serrano and the irregularly shaped, thin-fleshed Cayenne pepper.

The plant according to the invention and as described herein before may be an inbred, a dihaploid or a hybrid and/or a male sterile.

In one embodiment, the invention relates to plant material obtainable from a plant according to the invention and as described herein before including, but without being limited thereto, leaves, stems, roots, flowers or flower parts, fruits, pollen, egg cells, zygotes, seeds, cuttings, cell or tissue cultures, or any other part or product of the plant which still exhibits the resistant phenotype according to the invention, particularly when grown into a plant.

The invention further relates to plant parts obtainable from a plant according to the invention and as described herein before including, but without being limited thereto, plant seed, plant organs such as, for example, a root, stem, leaf, flower bud, or embryo, etc, ovules, pollen microspores, plant cells, plant tissue, plant cells cultures such as, for example, protoplasts, cell culture cells, cells in plant tissues, pollen, pollen tubes, ovules, embryo sacs, zygotes and embryos at various stages of development, etc; which still exhibits the resistant phenotype according to the invention, particularly when grown into a plant.

In one aspect, the invention relates to a method for introducing an allele at a quantitative trait locus ("QTL") contributing to resistance to *Bemisia* into a *Capsicum annuum* plant lacking said allele comprising:

a) obtaining a first plant of the genus *Capsicum* according to the invention and as described herein before, particularly a *Capsicum annuum* plant, comprising i) at least one marker allele characterized by the PCR amplification product, particularly a PCR amplification product obtainable by using PCR oligonucleotide primers or a pair of PCR oligonucleotide primers, particularly primer pairs selected from the group of primer pair 1 represented by a forward primer of SEQ ID NO: 1 and a reverse primer of SEQ ID NO: 2, identifying marker locus 1; primer pair 2 represented by a forward primer of SEQ ID NO: 3 and a reverse primer of SEQ ID NO: 4, identifying marker locus 2; primer pair 3 represented by a forward primer of SEQ ID NO: 5 and a reverse primer of SEQ ID NO: 6, identifying marker locus 3; primer pair 4 represented by a forward primer of SEQ ID NO: 7 and a reverse primer of SEQ ID NO: 8, identifying marker locus 4; primer pair 5 represented by forward primer of SEQ ID NO: 9 and a reverse primer of SEQ ID NO: 10, identifying marker locus 5; and primer pair 6 represented by a forward primer of SEQ ID NO: 11 and a reverse primer of SEQ ID NO: 12, identifying marker locus 6; or any other primer or primer pair that identifies a marker locus on chromosome 3 that is statistically correlated to the *Bemisia* resistance trait; or ii) at least one marker allele characterized by the PCR amplification product, particularly a PCR amplification product obtainable by using PCR oligonucleotide primers or a pair of PCR oligonucleotide primers, particularly primer pairs selected from the group of primer pair 7 represented by a forward primer of SEQ ID NO: 13 and a reverse primer of SEQ ID NO: 14, identifying marker locus 7; primer pair 8 represented by a forward primer of SEQ ID NO: 15 and a reverse primer of SEQ ID NO: 16, identifying marker locus 8; primer pair 9 represented by a forward primer of SEQ ID NO: 17 and a reverse primer of SEQ ID NO: 18, identifying marker locus 9; primer pair 10 represented by a forward primer of SEQ ID NO: 19 and a reverse primer of SEQ ID NO: 20, identifying marker locus 10; primer pair 11 represented by a forward primer of SEQ ID NO: 21 and a reverse primer of SEQ ID NO: 22, identifying marker locus 11; primer pair 12 represented by a forward primer of SEQ ID NO: 23 and a reverse primer of SEQ ID NO: 24, identifying marker locus 12, and primer pair 13 represented by a forward primer of SEQ ID NO: 25 and a reverse primer of SEQ ID NO: 26, identifying marker locus 13; or any other, primer or primer pair that identifies a marker locus on chromosome 5 that is statistically correlated to the *Bemisia* resistance trait or iii) a combination of i) and ii);

b) crossing said first plant of the genus *Capsicum*, particularly a *Capsicum annuum* plant, with a second *Capsicum annuum* plant, wherein said second *Capsicum annuum* plant lacks said nucleic acid; and c) identifying a plant resulting from the cross exhibiting increased resistance to *Bemisia* and comprising said at least one marker allele; or, optionally, d) identifying a plant resulting from the cross exhibiting increased resistance to *Bemisia* and missing said marker alleles identified in step a).

In one aspect, the invention relates to a method for introducing an allele at a quantitative trait locus ("QTL") contributing to resistance to thrips into a *Capsicum annuum* plant lacking said allele comprising:

a) obtaining a first plant, of the genus *Capsicum*, particularly a *Capsicum annuum* plant, comprising at least one marker allele characterized by the PCR amplification product; particularly a PCR amplification product obtainable by using PCR oligonucleotide primers or a pair of PCR oligonucleotide primers, particularly primer pairs selected from the group of primer pair 7 represented by a forward primer of SEQ ID NO: 13 and a reverse primer of SEQ ID NO: 14, identifying marker locus 7; primer pair 8 represented by a forward primer of SEQ ID NO: 15 and a reverse primer of SEQ ID NO: 16, identifying marker locus 8; primer pair 9 represented by a forward primer of SEQ ID NO: 17 and a reverse primer of SEQ ID NO: 18, identifying marker locus 9; primer pair 10 represented by a forward primer of SEQ ID NO: 19 and a reverse primer of SEQ ID NO: 20, identifying marker locus 10; primer pair 11 represented by a forward primer of SEQ ID NO: 21 and a reverse primer of SEQ ID NO: 22, identifying marker locus 11; primer pair 12 represented by a forward primer of SEQ ID NO: 23 and a reverse primer of SEQ ID NO: 24, identifying marker locus 12, and primer pair 13 represented by a forward primer of SEQ ID NO: 25 and a reverse primer of SEQ ID NO: 26, identifying marker locus 13; or any other primer or primer pair that identifies a marker locus on chromosome 5 that is statistically correlated to the thrips resistance trait;

b) crossing said first plant of the genus *Capsicum*, particularly a *Capsicum annuum* plant, with a second *Capsicum annuum* plant, wherein said second *Capsicum annuum* plant lacks said nucleic acid; and c) identifying a plant resulting from the cross exhibiting increased resistance to thrips and comprising said at least one marker allele; or, optionally, d) identifying a plant resulting from the cross exhibiting increased resistance to *Bemisia* and missing said marker alleles identified in step a).

In one aspect, the invention relates to a method for introducing at least a first allele at a quantitative trait locus ("QTL") contributing to resistance to *Bemisia* and at least a second, allele at a quantitative trait locus ("QTL") contributing to resistance to thrips and/or *Bemisia*, into a *Capsicum annuum* plant lacking said alleles comprising:

a) obtaining a first plant of the genus *Capsicum*, particularly a *Capsicum annuum* plant, comprising i) at least one marker allele characterized by the PCR amplification product, particularly a PCR amplification product obtainable by using. PCR oligonucleotide primers or a pair of PCR oligonucleotide primers, particularly primer pairs selected from the group of primer pair 1 represented by a forward primer of SEQ ID NO: 1 and a reverse primer of SEQ ID NO: 2, identifying marker locus 1; primer pair 2 represented by a forward primer of SEQ ID NO: 3 and a reverse primer of SEQ ID NO: 4, identifying marker locus 2; primer pair 3 represented by a forward primer of SEQ ID NO: 5 and a reverse primer of SEQ ID NO: 6, identifying marker locus 3; primer pair 4 represented by a forward primer of SEQ ID NO: 7 and a reverse primer of SEQ ID NO: 8, identifying marker locus 4; primer pair 5 represented by a forward primer of SEQ ID NO: 9 and a reverse primer of SEQ ID NO: 10, identifying marker locus 5; and primer pair 6 represented by a forward primer of SEQ ID NO: 11 and a reverse primer of SEQ ID NO: 12, identifying marker locus 6; or any other primer or primer pair that identifies a marker locus on chromosome 3 that is statistically correlated to the *Bemisia* resistance trait; and ii) at least one marker allele characterized by the PCR amplification product, particularly a PCR amplification product obtainable by using PCR oligonucleotide primers or a pair of PCR oligonucleotide primers, particularly primer pairs selected from the group of primer pair 7, represented by a forward primer of SEQ ID NO: 13 and a reverse primer of SEQ ID NO: 14, identifying marker lotus 7; primer pair 8 represented by a forward primer of SEQ ID NO: 15 and a reverse primer of SEQ ID NO: 16, identifying marker locus 8; primer pair 9 represented by a forward primer of SEQ ID NO: 17 and a reverse primer of SEQ ID NO: 18, identifying marker locus 9; primer pair 10 represented by a forward primer of SEQ ID NO: 19 and a reverse primer of SEQ ID NO: 20, identifying marker locus 10; primer pair 11 represented by a forward primer of SEQ ID NO: 21 and a reverse primer of SEQ ID NO: 22, identifying marker locus 11; primer pair 12 represented by a forward primer of SEQ ID NO: 23 and a reverse primer of SEQ ID NO: 24, identifying marker locus 12, and primer pair 13 represented by a forward primer of SEQ ID NO: 25 and a reverse primer of SEQ ID NO: 26, identifying marker locus 13; or by any other primer or primer pair that identifies a marker locus on chromosome 5 that is statistically correlated to the thrips and/or *Bemisia* resistance trait;

b) crossing said first plant of the genus *Capsicum*, particularly a *Capsicum annuum* plant, with a second *Capsicum annuum* plant, wherein said second *Capsicum annuum* plant lacks said nucleic acids; and c) identifying a plant resulting from the cross exhibiting increased resistance to *Bemisia* and/or thrips, and comprising at least two marker alleles co-segregating with said resistance or, optionally, d) identifying a plant resulting from the cross exhibiting increased resistance to *Bemisia* and/or thrips and missing said marker alleles identified in step a).

In one aspect, the relates to a method for introducing a QTL contributing, to resistance to *Bemisia* into a *Capsicum annuum* plant lacking said allele comprising:

a) obtaining a first plant of the genus *Capsicum*, particularly a *Capsicum annuum* plant, which plant contains a genome comprising a quantitative trait locus ("QTL") which contributes to *Bemisia* resistance, wherein said QTL is characterized by being genetically linked to at least one marker locus, particularly to at least two marker loci, more particularly to at least three marker loci and even more particularly to at least four marker loci, but especially to at least five and up to six marker loci, which marker loci are on chromosome 3 and co-segregate with the *Bemisia* resistance trait and can be identified by using PCR oligonucleotide primers or a pair of PCR oligonucleotide primers, particularly primer pairs selected from the group of primer pair 1 represented by a forward primer of SEQ ID NO: 1 and a reverse primer of SEQ ID NO: 2, identifying marker locus 1; primer pair 2 represented by a forward primer of SEQ ID NO: 3 and a reverse primer of SEQ ID NO: 4, identifying marker locus 2; primer pair 3 represented by a forward primer of SEQ ID NO: 5 and a reverse primer of SEQ ID NO: 6, identifying marker locus 3; primer pair 4 represented by a forward primer of SEQ ID NO: 7 and a reverse primer of SEQ ID NO: 8, identifying marker locus 4; primer pair 5 represented by a forward primer of SEQ ID NO: 9 and a reverse primer of SEQ ID NO: 10, identifying marker locus 5; and primer pair 6 represented by a forward primer of SEQ ID NO: 11 and a reverse primer of SEQ ID NO: 12, identifying marker locus 6; or by any other marker locus on chromosome 3 that is statistically correlated to the *Bemisia* resistance trait;

b) crossing said first plant of the genus *Capsicum*, particularly a *Capsicum annuum* plant, with a second. *Capsicum annuum* plant, wherein said second *Capsicum annuum* plant lacks said nucleic acid; and c) identifying a plant resulting from the cross exhibiting increased resistance to *Bemisia* and comprising said QTL.

In another aspect, the invention relates to a method for introducing a QTL contributing to thrips resistance into a *Capsicum annuum* plant lacking said allele comprising:

a) obtaining a first plant of the genus *Capsicum*, particularly a *Capsicum annuum* plant, which plant contains a genome comprising a quantitative trait locus ("QTL") which contributes to thrips resistance, wherein said QTL is characterized by being genetically linked to at least one marker locus, particularly to at least two marker loci, particularly to at least three marker loci and particularly to at least four marker loci, particularly to at least five marker loci, particularly to at least six marker loci, and up to seven marker loci, which marker loci are on chromosome 5 and co-segregate with the thrips resistance trait and can be identified by a pair of PCR oligonucleotide primers selected from the group of primer pair 7 represented by a forward primer of SEQ ID NO: 13 and a reverse primer of SEQ ID NO: 14, identifying marker locus 7; primer pair 8 represented by a forward primer of SEQ ID NO: 15 and a reverse primer of SEQ ID NO: 16, identifying marker locus 8; primer pair 9 represented by a forward primer of SEQ ID NO: 17 and a reverse primer of SEQ ID NO: 18, identifying marker locus 9; primer pair 10 represented by a forward primer of SEQ ID NO: 19 and a reverse primer of SEQ ID NO: 20, identifying marker locus 10; primer pair 11 represented by a forward primer of SEQ ID NO: 21 and a reverse primer of SEQ ID NO: 22, identifying marker locus 11; primer pair 12 represented by a forward primer of SEQ ID NO: 23 and a reverse primer of SEQ ID NO: 24, identifying marker locus 12; and primer pair 13 represented by a forward primer of SEQ ID NO: 25 and a reverse primer of SEQ ID NO: 26, identifying marker locus 13, or by any other marker locus on chromosome 5 that is statistically correlated to the thrips resistance trait;

b) crossing said first plant of the genus *Capsicum*, particularly a *Capsicum annuum* plant, with a second *Capsicum annuum* plant, wherein said second *Capsicum annuum* plant lacks said nucleic acid; and c) identifying a plant resulting from the cross exhibiting increased resistance to thrips and comprising said QTL.

In one aspect, the invention relates to a method for introducing QTL contributing to resistance to *Bemisia* and to thrips resistance into a *Capsicum annuum* plant lacking said allele(s) comprising a) obtaining a first plant of the genus *Capsicum*, particularly a *Capsicum annuum* plant, which plant contains a genome comprising a quantitative trait locus ("QTL") which contributes to i) *Bemisia* resistance, wherein said QTL is characterized by being genetically linked to at least one marker locus, particularly to at least two marker loci, more particularly to at least three marker loci and even more particularly to at least four marker loci, but especially to at least five and up to six marker loci, which marker loci are on chromosome 3 and co-segregate with the *Bemisia* resistance trait and can be identified by using PCR oligonucleotide primers or a pair of PCR oligonucleotide primers, particularly primer pairs selected from the group of primer pair 1 represented by a forward primer of SEQ ID NO: 1 and a reverse primer of SEQ ID NO: 2, identifying marker locus 1; primer pair 2 represented by a forward primer of SEQ ID NO: 3 and a reverse primer of SEQ ID NO: 4, identifying marker locus 2; primer pair 3 represented by a forward primer of SEQ ID NO: 5 and a reverse primer of SEQ ID NO: 6, identifying marker locus 3; primer pair 4 represented by a forward primer of SEQ ID NO: 7 and a reverse primer of SEQ ID NO: 8, identifying marker locus 4; primer pair 5 represented by a forward primer of SEQ ID NO: 9 and a reverse primer of SEQ ID NO: 10, identifying marker locus 5; and primer pair 6 represented by a forward primer of SEQ ID NO: 11 and a reverse primer of SEQ ID NO: 12, identifying marker locus 6, or by any other marker locus on chromosome 3 that is statistically correlated to the *Bemisia* resistance trait; and ii) thrips resistance, wherein said QTL is characterized by being genetically linked to at least one marker locus, particularly to at least two marker loci, particularly to at least three marker loci and particularly to at least four marker loci, particularly to at least five marker loci, particularly to at least six marker loci, and up to seven marker loci, which marker loci are on chromosome 5 and co-segregate with the thrips resistance trait and can be identified by using PCR oligonucleotide primers or a pair of PCR oligonucleotide primers, particularly primer pairs selected from the group of primer pair 7 represented by a forward primer of SEQ ID NO: 13 and a reverse primer of SEQ ID NO: 14, identifying marker locus 7; primer pair 8 represented by a forward primer of SEQ ID NO: 15 and a reverse primer of SEQ ID NO: 16, identifying marker locus 8; primer pair 9 represented by a forward primer of SEQ ID NO: 17 and a reverse primer of SEQ ID NO: 18, identifying marker locus 9; primer pair 10 represented by a forward primer of SEQ ID NO: 19 and a reverse primer of SEQ ID NO: 20, identifying marker locus 10; primer pair 11 represented by a forward primer of SEQ ID NO: 21 and a reverse primer of SEQ ID NO: 22, identifying marker locus 11; primer pair 12 represented by a forward primer of SEQ ID NO: 23 and a reverse primer of SEQ ID NO: 24, identifying marker locus 12, and primer pair 13 represented by a forward primer of SEQ ID NO: 25 and a reverse primer of SEQ ID NO: 26, identifying marker locus 13, or by any other marker locus on chromosome 5 that is statistically correlated to the thrips resistance trait;

b) crossing said first plant of the genus *Capsicum*, particularly a *Capsicum annuum* plant, with a second. *Capsicum annuum* plant, wherein said second *Capsicum annuum* plant lacks said nucleic acid(s); and c) identifying a plant resulting from the cross exhibiting increased resistance to *Bemisia* and thrips, and comprising said QTL.

In a specific embodiment of the invention the first *Capsicum annuum* plant is a plant which has the genetic background, but particularly the genetic architecture at the *Bemisia* and/or the thrips resistance locus, of line 061M4387, representative seed of which is deposited under Accession No. NCIMB 41428, or a progeny or an ancestor thereof, particularly a plant which has the genetic background or architecture at the QTL of line 061M4387, or a progeny or an ancestor thereof, but especially a plant of said line 061M4387, or a progeny or an ancestor thereof.

In another specific embodiment of the invention, the identification of a *Capsicum* plant exhibiting increased resistance to *Bemisia* and/or thrips and comprising a QTL according to the invention in step c) of any of the methods described herein before is carried out by phenotypic evaluation using a ranking scale as disclosed in Examples 2A and 2B, respectively, or by using a molecular marker according to the invention and as disclosed herein before, or a combination thereof.

In one aspect, the invention relates to the use of an allele or a QTL obtainable from a plant which has the genetic background, but particularly the genetic architecture at the *Bemisia* and/or the thrips resistance locus, of line 061M4387, representative seed of which is deposited under Accession No. NCIMB 41428, or a progeny or an ancestor thereof, particularly from a plant which has the genetic architecture at the QTL contributing to the *Bemisia* and/or the thrips resistance of line 061M4387, or a progeny or an ancestor thereof, but especially from said line 061M4387, or a progeny or an ancestor thereof, to confer resistance to *Bemisia* and/or to thrips upon a *Capsicum annuum* plant lacking said allele associated with *Bemisia* resistance and thrips resistance, respectively.

The invention further comprises a cultivated *Capsicum annuum* plant resistant, particularly intermediately resistant, to *Bemisia*, which plant is obtainable by crossing a *Capsicum annuum* plant susceptible to *Bemisia* with a plant of line 061M4387, representative seed of which is deposited under Accession No. NCIMB 41428, or a progeny or an ancestor thereof; and by selecting a plant comprising a QTL, which can be identified in a PCR reaction by a pair of PCR oligonucleotide primers consisting of a forward primer and a reverse primer exhibiting a nucleotide sequence which is at least 90%, particularly at least 95%, particularly at least 96%, particularly at least 97%, particularly at least 98%, particularly at least 99% identical to that given in SEQ ID NOs: 1-12; or by any other primer or primer pair that identifies a marker locus on chromosome 3 that is statistically correlated to the *Bemisia* resistance trait.

In one embodiment, the invention provides a cultivated *Capsicum annuum* plant resistant, particularly intermediately resistant, to thrips, which plant is obtainable by crossing a *Capsicum annuum* plant susceptible to thrips with a plant of line 061M4387, representative seed of which is deposited under Accession. No. NCIMB 41428, or a progeny or an ancestor thereof; and by selecting a plant comprising a QTL, which can be identified in a PCR reaction by a pair of PCR oligonucleotide primers consisting of a forward primer and a reverse primer exhibiting, a nucleotide sequence which is at least 90%, particularly at least 95%, particularly at least 96%, particularly at least 97%, particularly at least 98%, particularly at least 99% identical to that given in SEQ ID NOs: 13-26, or by any other primer or primer pair that identifies a marker locus on chromosome 5 that is statistically correlated to the thrips resistance trait.

In one embodiment, the invention provides a cultivated *Capsicum annuum* plant resistant, particularly intermediately resistant, to *Bemisia* and thrips, which plant is obtainable by crossing a *Capsicum annuum* plant susceptible to *Bemisia* and/or thrips with a plant of line 061M4387, representative seed of which is deposited under Accession No. NCIMB 41428, or a progeny or an ancestor thereof; and by selecting a plant comprising a QTL, which can be identified in a PCR reaction by a pair of PCR oligonucleotide primers consisting of a forward primer and a reverse primer exhibiting a nucleotide sequence which is at least 90%, particularly at least 95%, particularly at least 96%, particularly at least 97%, particularly at least 98%, particularly at least 99% identical to that given in SEQ ID NOs: 1-12 and in SEQ ID NOs: 13-26, respectively, or by any other primer or primer pair that identifies a marker locus on chromosome 3 and on chromosome 5 that is statistically correlated to the thrips and *Bemisia* resistance trait, respectively.

In one aspect, the invention relates to a method of producing pepper fruit comprising:

a) growing a cultivated *Capsicum annuum* plant resistant, particularly intermediately resistant, to *Bemisia* according to the invention and as described herein before;

b) allowing said plant to set fruit; and c) harvesting fruit of said plant.

In one aspect, the invention relates to a method of producing pepper fruit, particularly pepper fruit which is essentially free of feeding damage caused by *Bemisia* and/or thrips comprising:

a) growing a cultivated *Capsicum annuum* plant resistant, particularly intermediately resistant, to thrips according to the invention and as described herein before;

b) allowing said plant to set fruit; and c) harvesting fruit of said plant.

In one aspect, the invention relates to a method of producing pepper fruit, particularly pepper fruit which essentially free of feeding damage caused by thrips comprising:

a) growing a cultivated *Capsicum annuum* plant resistant, particularly intermediately resistant, to *Bemisia* and to thrips according to the invention and as described herein before;

b) allowing said plant to set fruit; and c) harvesting fruit of said plant.

In another aspect, the invention relates to a method of producing pepper seed comprising:

a) growing cultivated *Capsicum annuum* plant resistant, particularly intermediately resistant, to *Bemisia* according to the invention and as described herein before;

b) harvesting fruit of said plant; and c) extracting seed from said fruit.

In another aspect, the invention relates to a method of producing pepper seed comprising:

a) growing cultivated *Capsicum annuum* plant resistant; particularly intermediately resistant, to thrips according to the invention and as described herein before;

b) harvesting fruit of said plant; and c) extracting seed from said fruit.

In another aspect, the invention relates to a method of producing pepper seed comprising:
  a) growing cultivated *Capsicum annuum* plant resistant, particularly intermediately resistant, to *Bemisia* and to thrips according to the invention and as described herein before;
  b) harvesting fruit of said plant; and
  c) extracting seed from said fruit.

In one embodiment; the invention relates to a method of producing a pepper plant that exhibits resistance to *Bemisia*, wherein said plant comprises an allele associated with resistance to *Bemisia* at a quantitative trait loci ("QTL") contributing to *Bemisia* resistance located on chromosome 3; particularly at a QTL derived from *Capsicum annuum* line 061M4387 representative seed of which is deposited under Accession No. NCIMB 41428, or from a progeny or an ancestor thereof comprising said QTL, comprising the steps of:
  a) providing a recipient pepper plant susceptible to *Bemisia* or a plant that does not contain a QTL allele conferring resistance to *Bemisia* infestations;
  b) providing a donor pepper plant exhibiting resistance to *Bemisia* infestations due to the presence of the resistance QTL allele on chromosome 3
  c) crossing the recipient and the donor plant to produce progeny plants segregating for the presence of the favourable QTL allele;
  d) screening the genome of progeny plants for recombinations in the region of the QTL on chromosome 3.

In one embodiment, the invention relates to a method of producing a pepper plant that exhibits resistance to *Bemisia*, wherein said plant comprises an allele associated with resistance to *Bemisia* at a quantitative trait loci ("QTL") contributing to thrips resistance located on chromosome 3 and/or chromosome 5; particularly at a QTL derived from *Capsicum annuum* line 061M4387 representative seed of which is deposited under Accession No. NCIMB 41428, or from a progeny or an ancestor thereof, comprising said QTL, comprising the steps of:
  a) providing a recipient pepper plant susceptible to *Bemisia* or a plant that does not contain a QTL allele conferring resistance to *Bemisia* infestations;
  b) providing a donor pepper plant exhibiting resistance to *Bemisia* infestations due to the presence of the resistance QTL allele on chromosome 3 and/or chromosome 5;
  c) crossing the recipient and the donor plant to produce progeny plants segregating for the presence of the favourable QTL allele;
  d) screening the genome of progeny plants for recombinations in the region of the QTL on chromosome 3 and/or chromosome 5.

In one embodiment, the invention relates to a method of producing a pepper plant that exhibits resistance to thrips, wherein said plant comprises an allele associated with resistance to thrips at a quantitative trait loci ("QTL") contributing to thrips resistance located on chromosome 5; particularly at a QTL derived from *Capsicum annuum* line 061M4387 representative seed of which is deposited under Accession No. NCIMB 41428, or from a progeny or an ancestor thereof comprising said QTL, comprising the steps of:
  a) providing a recipient pepper plant susceptible to thrips or a plant that does not contain a QTL allele conferring resistance to thrips infestations;
  b) providing a donor pepper plant exhibiting resistance to thrips infestations due to the presence of the resistance QTL allele on chromosome 5;
  c) crossing the recipient and the donor plant to produce progeny plants segregating for the presence of the favourable QTL allele;
  d) screening the genome of progeny plants for recombinations in the region of the QTL on chromosome 5.

In one embodiment, the invention relates to a method of producing a pepper plant that exhibits resistance to *Bemisia*, and thrips wherein said plant comprises an allele associated with resistance to *Bemisia* at a quantitative trait loci ("QTL") contributing to *Bemisia* resistance located on chromosome 3 and an allele associated with resistance to thrips and/or *Bemisia* at a quantitative trait loci ("QTL") contributing to thrips and/or *Bemisia* resistance located on chromosome 5; particularly at QTL located on chromosome 3 and 5, respectively, derived from *Capsicum annuum* line 061M4387 representative seed of which is deposited under Accession No. NCIMB 41428, or from a progeny or an ancestor thereof comprising said QTL, comprising the steps of
  a) providing a recipient pepper plant susceptible to *Bemisia* and/or thrips or a plant that does not contain a QTL allele conferring resistance to *Bemisia* and/or thrips infestations;
  b) providing a donor pepper plant exhibiting resistance to *Bemisia* and/or thrips infestations due to the presence of the resistance QTL allele on chromosome 3 and/or 5, respectively;
  c) crossing the recipient and the donor plant to produce progeny plants segregating for the presence of the favourable QTL allele;
  d) screening the genome of progeny plants for recombinations in the region of the QTL on chromosome 3 and/or 5.

In one embodiment, the invention relates to a method of producing a pepper plant that exhibits resistance to *Bemisia* and/or thrips according to the invention and as described herein before, wherein said progeny plant is a plant of a segregating population produced by self-pollination of an F1 plant obtained from said cross in step c), or by crossing an F1 plant obtained from said cross with another pepper plant.

In one embodiment the invention relates to a method of producing a pepper plant that exhibits resistance to *Bemisia* and/or thrips according to the invention and as described herein before, wherein the segregating population obtained in step c) may be subjected to a standard resistance assay such as, for example, a resistance assay as described in Example 2A and 2B, respectively.

In one embodiment, the invention relates to a method of producing a pepper plant that exhibits resistance to *Bemisia* and/or thrips according to the invention and as described herein before, wherein the screening of the progeny plants in step d) is be a marker-based screening, which may be supported by performing a resistance assay such as, for example, a resistance assay as described in Example 2A and 2B, respectively.

In one embodiment, the invention relates to a method of producing a pepper plant that exhibits, resistance to *Bemisia* and/or thrips according to the invention and as described herein before, wherein the screening of the genome is performed using molecular markers genetically linked to chromosome 3 and/or chromosome 5, respectively.

In one embodiment, the invention relates to a method of producing a pepper plant that exhibits resistance to *Bemisia* according to the invention and as described herein before, wherein the screening of the genome is performed using molecular markers genetically linked to at least one marker characterized by the PCR amplification product of a PCR oligonucleotide primer or a pair of PCR oligonucleotide primers selected from the group of primer pairs 1-6 represented by forward and reverse primers of SEQ ID NOs: 1-12.

In one embodiment, the invention relates to a method of producing a pepper plant that exhibits resistance to thrips according to the invention and as described herein before, wherein the screening of the genome is performed using molecular markers genetically linked to at least one marker characterized by the PCR amplification product of a PCR oligonucleotide primer or a pair of PCR oligonucleotide primers selected from the group of primer pairs 7-13 represented by forward and reverse primers of SEQ ID NOs: 13-26.

In one embodiment, the invention relates to a method of producing a pepper plant that exhibits resistance to Bemisia according to the invention and as described herein before, wherein progeny plants are identified and selected which comprise a reduced genome segment at the QTL still conferring resistance to Bemisia, wherein the link to at least one marker allele at least one marker locus linked to the QTL in the donor plant, which marker allele is characterized by the PCR amplification product of an PCR oligonucleotide primer or oligonucleotide primer pair selected from the group of primer pairs 1-6 represented by forward and reverse primers of SEQ ID NOs: 1-12, has been broken.

In one embodiment, the invention relates to a method of producing a pepper plant that exhibits resistance to Bemisia according to the invention and as described herein before, wherein progeny plants are identified and selected which comprise a reduced genome segment at the QTL still conferring resistance to Bemisia, wherein the link to all the marker alleles characterized by the PCR amplification product of an PCR oligonucleotide primer or oligonucleotide primer pair selected from the group of primer pairs 1-6 represented by forward and reverse primers of SEQ ID NOs: 1-12, has been broken.

In one embodiment, the invention relates to a method of producing a pepper plant that exhibits resistance to thrips according to the invention and as described herein before, wherein progeny plants are identified and selected which comprise a reduced genome segment at the QTL still conferring resistance to thrips, wherein the link to at least one marker allele at least one marker locus linked to the QTL in the donor plant, which marker allele is characterized by the PCR amplification product of an PCR oligonucleotide primer or oligonucleotide primer pair selected from the group of primer pairs 7-13 represented by forward and reverse primers of SEQ ID NOs: 13-26, has been broken.

In one embodiment, the invention relates to a method of producing a pepper plant that exhibits resistance to thrips according to the invention and as described herein before, wherein progeny plants are identified and selected which comprise a reduced genome segment at the QTL still conferring resistance to thrips, wherein the link to all the marker alleles characterized by the PCR amplification product of an PCR oligonucleotide primer or oligonucleotide primer pair selected from the group of primer pairs 7-1.3 represented by forward and reverse primers of SEQ ID NOs: 13-26, has been broken.

In one embodiment, the invention relates to a method of producing a pepper plant that exhibits resistance to Bemisia and/or thrips according to the invention and as described herein before, wherein plants comprising a genome segment, particularly a reduced genome segment at the QTL still conferring resistance to Bemisia and/or thrips are identified by a marker-based screening or by performing a resistance assay or by a combination of both, particularly by a marker-based screening, wherein markers are used that are located in the QTL region and are genetically linked to at least one marker locus, provided that said markers are segregating in the same population.

In one embodiment, the invention relates to a method of identifying a quantitative trait locus ("QTL") which contributes to Bemisia resistance comprising using in a PCR reaction a PCR oligonucleotide primer or a pair of PCR oligonucleotide primers selected from the group of primer pair 1 represented by a forward primer of SEQ ID NO: 1 and a reverse primer of SEQ ID NO: 2, identifying marker locus 1; primer pair 2 represented by a forward primer of SEQ ID NO: 3 and a reverse primer of SEQ ID NO: 4, identifying marker locus 2; primer pair 3 represented by a forward primer of SEQ ID NO: 5 and a reverse primer of SEQ ID NO: 6, identifying marker locus 3; primer pair 4 represented by forward primer of SEQ ID NO: 7 and a reverse primer of SEQ ID NO: 8, identifying marker locus 4; primer pair 5 represented by a forward primer of SEQ ID NO: 9 and a reverse primer of SEQ ID NO: 10, identifying marker locus 5; and primer pair 6 represented by a forward primer of SEQ ID NO: 11 and a reverse primer of SEQ ID NO: 12, identifying marker locus 6.

In one embodiment, the invention relates to a method of identifying a quantitative trait locus ("QTL") which contributes to Bemisia resistance comprising using in a PCR reaction a PCR oligonucleotide primer or a pair of PCR oligonucleotide primers selected from the group of primer pair 7 represented by a forward primer of SEQ ID NO: 13 and a reverse primer of SEQ ID NO: 14, identifying marker locus 7; primer pair 8 represented by a forward primer of SEQ ID NO: 15 and a reverse primer of SEQ ID NO: 16, identifying marker locus 8; primer pair 9 represented by a forward primer of SEQ ID NO: 17 and a reverse primer of SEQ ID NO: 18, identifying marker locus 9; primer pair 10 represented by a forward primer of SEQ ID NO: 19 and a reverse primer of SEQ ID NO: 20, identifying marker locus 10; primer pair 11 represented by a forward primer of SEQ ID NO: 21 and a reverse primer of SEQ ID NO: 22, identifying marker locus 11; primer pair 12 represented by a forward primer of SEQ ID NO: 23 and a reverse primer of SEQ ID NO: 24, identifying marker locus 12, and primer pair 13 represented by a forward primer of SEQ ID NO: 25 and a reverse primer of SEQ ID NO: 26, identifying marker locus 13.

In one embodiment, the invention relates to a method of identifying a quantitative trait locus ("QTL") which contributes to Bemisia resistance comprising using in a PCR reaction
a) a PCR oligonucleotide primer or a pair of PCR oligonucleotide primers selected from the group of primer pair 1 represented by a forward primer of SEQ ID NO: 1 and a reverse primer of SEQ ID NO: 2, identifying marker locus 1; primer pair 2 represented by a forward primer of SEQ ID NO: 3 and a reverse primer of SEQ ID NO: 4, identifying marker locus 2; primer pair 3 represented by a forward primer of SEQ ID NO: 5 and a reverse primer of SEQ ID NO: 6, identifying marker locus 3; primer pair 4 represented by a forward primer of SEQ ID NO: 7 and a reverse primer of SEQ ID NO: 8, identifying marker locus 4; primer pair 5 represented by a forward primer of SEQ ID NO: 9 and a reverse primer of SEQ ID NO: 10, identifying marker locus 5; and primer pair 6 represented by a forward primer of SEQ ID NO: 11 and a reverse primer of SEQ ID NO: 12, identifying marker locus 6; and
b) a PCR oligonucleotide primer or a pair of PCR oligonucleotide primers selected from the group of primer pair 7 represented by a forward primer of SEQ ID NO: 13 and a reverse primer of SEQ ID NO: 14, identifying marker locus 7; primer pair 8 represented by a forward primer of SEQ ID NO: 15 and a reverse primer of SEQ ID NO: 16, identifying marker locus 8; primer pair 9 represented by a forward primer of SEQ ID NO: 17 and a reverse primer of SEQ ID NO: 18, identifying marker locus 9; primer pair 10, represented by a forward primer of SEQ ID NO: 19 and, a reverse primer of SEQ ID NO: 20, identifying marker locus 10; primer pair 11 represented by a forward primer of SEQ ID NO: 21 and a reverse primer of SEQ ID NO: 22, identifying marker locus 11; primer pair 12 represented by a forward primer of SEQ ID NO: 23 and a reverse primer of SEQ ID NO: 24, identifying marker locus 12, and primer pair 13 represented by a forward primer of SEQ ID NO: 25 and a reverse primer of SEQ ID NO: 26, identifying marker locus 13.

In one embodiment, the invention relates to a method of identifying a quantitative trait locus ("QTL") which contributes to thrips resistance comprising using in a PCR reaction a PCR oligonucleotide primer or a pair of PCR oligonucleotide primers selected from the group of primer pair 7 represented by a forward primer of SEQ ID NO: 13 and a reverse primer of SEQ ID NO: 14, identifying marker locus 7; primer pair 8 represented by a forward primer of SEQ ID NO: 15 and a reverse primer of SEQ ID NO: 16, identifying marker locus 8; primer pair 9 represented by a forward primer of SEQ ID NO: 17 and a reverse primer of SEQ ID NO: 18, identifying marker locus 9; primer pair 10 represented by a forward primer of SEQ ID NO: 19 and a reverse primer of SEQ ID NO: 20, identifying marker locus 10; primer pair 11 represented by a forward primer of SEQ ID NO: 21 and a reverse primer of SEQ ID NO: 22, identifying marker locus 11; primer pair 12 represented by a forward primer of SEQ ID NO: 23 and a reverse primer of SEQ ID NO: 24, identifying marker locus 12, and primer pair 13 represented by a forward primer of SEQ ID NO: 25 and a reverse primer of SEQ ID NO: 26, identifying marker locus 13.

In one embodiment, the invention relates to a QTL identified by a method, according to the invention and as described herein before, which QTL contributes to *Bemisia* resistance and is located on chromosome 3.

In one embodiment, the invention relates to a QTL identified by a method according to the invention and as described herein before, which QTL contributes to *Bemisia* resistance and is located on chromosome 5.

In one embodiment, the invention relates to a QTL identified by a method according to the invention and as described herein before, which QTL contributes to thrips resistance and is located on chromosome 5.

In one embodiment, the invention provides a cultivated *Capsicum annuum* plant comprising a genome comprising at least one QTL which contributes to *Bemisia* resistance, which QTL is located on chromosome 3, wherein said at least one QTL can be identified by a molecular marker that is in linkage disequilibrium and/or linked to and/or located in the QTL region, as well as a marker that represent the actual causal mutations underlying the QTL, and thus exhibits statistical correlation to the phenotypic trait, which marker can be developed using the oligonucleotide primers as disclosed in SEQ ID NO: 1-12.

In one embodiment, the invention provides a cultivated *Capsicum annuum* plant comprising a genome comprising at least two QTL which contribute to *Bemisia* resistance, which QTL are located on chromosome 3 and 5, wherein said at least two QTL can be identified by molecular markers that are in linkage disequilibrium and/or linked to and/or located in the QTL region, as well as a markers that represent the actual causal mutations underlying the QTL, and thus exhibits statistical correlation to the phenotypic trait, which markers can be developed using the oligonucleotide primers as disclosed in SEQ ID NO: 1-12 and SEQ ID NOs: 13 to 26, respectively.

In one embodiment, the invention provides a cultivated *Capsicum annuum* plant comprising a genome comprising at least one QTL which contributes to thrips resistance, which QTL is located on chromosome 5, wherein said at least one QTL can be identified by a molecular marker that is in linkage disequilibrium and/or linked to and/or located in the QTL region, as well as a marker that represent the actual causal mutations underlying the QTL, and thus exhibits statistical correlation to the phenotypic trait, which marker can be developed using the oligonucleotide primers as disclosed in SEQ ID NOs: 13 to 26.

In one embodiment, the invention provides a cultivated *Capsicum annuum* plant comprising a genome comprising at least two QTL which contribute to *Bemisia* and thrips resistance, which QTL are located on chromosomes 3 and 5 and wherein said at least two QTL can be identified by a molecular markers that are in linkage disequilibrium and/or linked to and/or located in the QTL region, as well as a markers that represent the actual causal mutations underlying the QTL, and thus exhibits statistical correlation to the phenotypic trait, which markers can be developed using the oligonucleotide primers as disclosed in SEQ ID NO: 1-12 and SEQ ID NOs: 13 to 26, respectively.

DEFINITIONS

The technical terms and expressions used within the scope of this application are generally to be given the meaning, commonly applied to them in the pertinent art of plant breeding and cultivation if not otherwise indicated herein below.

A "cultivated *Capsicum annuum*" plant is understood within the scope of the invention to refer to a plant that is no longer in the natural state but has been developed by human care and for human use and/or consumption.

As used in this specification and the appended claims, the singular forms "a", "an", and "the" include plural referents unless the context clearly dictates otherwise. Thus, for example, reference to "a plant" includes one or more plants, and reference to "a cell" includes mixtures of cells, tissues, and the like.

An "allele" is understood within the scope of the invention to refer to alternative or variant forms of various genetic units identical or associated with different forms of a gene or of any kind of identifiable genetic element, which are alternative in inheritance because they are situated at the same locus in homologous chromosomes. Such alternative or variant forms may be the result of single nucleotide polymorphisms; insertions, inversions, translocations or deletions, or the consequence of gene regulation caused by, for example, by chemical or structural modification, transcription regulation or post-translational modification/regulation. In a diploid cell or organism, the two alleles of a given gene or genetic element typically occupy corresponding loci on a pair of homologous chromosomes.

An allele associated with a quantitative trait may comprise alternative or variant forms of various genetic units including those that are identical or associated with a single gene or multiple genes or their products or even a gene disrupting or controlled by a genetic factor contributing to the phenotype represented by said QTL.

As used herein, the term "marker allele" refers to an alternative or variant form of a genetic unit as defined herein above, when used as a marker to locate genetic loci containing alleles on a chromosome that contribute to variability of phenotypic traits.

As used herein, the term "breeding", and grammatical variants thereof, refer to any process that generates a progeny individual. Breedings can be sexual or asexual, or any combination thereof. Exemplary non-limiting types of breedings include crossings, selfings, doubled haploid derivative generation, and combinations thereof.

As used herein, the phrase "established breeding population" refers to a collection of potential breeding partners produced by and/or used as parents in a breeding program; e.g., a commercial breeding program. The members of the established breeding population are typically well-characterized genetically and/or phenotypically. For example, several phenotypic traits of interest might hove been evaluated, e.g., under different environmental conditions, at multiple locations, and/or at different times. Alternatively or in addition, one or more genetic loci associated with expression of the phenotypic traits might have been identified and one or more of the members of the breeding population might have been genotyped with respect to the one or more genetic loci as well as with respect to one or more genetic markers that are associated with the one or more genetic loci.

As used herein, the phrase "diploid individual" refers to an individual that has two sets of chromosomes, typically one from each of its two parents. However, it is understood that in some embodiments a diploid individual can receive its "maternal" and "paternal" sets of chromosomes from the same single organism, such as when a plant is selfed to produce a subsequent generation of plants.

"Homozygous" is understood within the scope of the invention to refer to like alleles at, one or more corresponding loci on homologous chromosomes.

"Heterozygous" is understood within, the scope of the invention to refer to unlike alleles at one or more corresponding loci on homologous chromosomes.

"Backcrossing" is understood within the scope of the invention to refer to a process in which a hybrid progeny is repeatedly crossed back to one of the parents. Different recurrent parents may be used in subsequent backcrosses.

"Locus" is understood within the scope of the invention to refer to a region on a chromosome, which comprises a gene or any other genetic element or factor contributing to a trait.

As used herein, "marker locus" refers to a region on a chromosome, which comprises a nucleotide or a polynucleotide sequence that is present in an individual's genome and that is associated with one or more loci of interest, which may which comprise a gene or any other genetic element or factor contributing to a trait. "Marker locus" also refers to a region on a chromosome, which comprises a polynucleotide sequence complementary to a genomic sequence, such as a sequence of a nucleic acid used as probes.

"Genetic linkage" is understood within the scope of the invention to refer to an association of characters in inheritance due to location of genes in proximity on the same chromosome, measured by percent recombination between loci (centi-Morgan, cM).

As used herein, the phrase "quantitative trait" refers to a phenotypic trait that can be described numerically (i.e., quantitated or quantified). A quantitative trait typically exhibits continuous variation between individuals of a population; that is, differences in the numerical value of the phenotypic trait are slight and grade into each other. Frequently, the frequency distribution in a population of a quantitative phenotypic trait exhibits a bell-shaped curve (i.e., exhibits a normal distribution between two extremes). In the present case the quantitative trait exhibits continuous variation between individuals of a population in terms of resistance to insects of the genus *Bemisia* and/or the order Thysanoptera, which resistance is scored by means of a standardized Insect Resistance Assay using a scale from 1-9 for assessing the severity of the infestation. A quantitative trait, is typically the result of a genetic locus interacting with the environment or of multiple genetic loci (QTL) interacting with each other and/or with the environment. Examples of quantitative traits include plant height and yield.

For the purpose of the present invention, the term "co-segregation" refers to the fact that the allele for the trait and the allele(s) for the marker(s) tend to be transmitted together because they are physically close together on the same chromosome (reduced recombination between them because of their physical proximity) resulting in a non-random association of their alleles as a result of their proximity on the same chromosome. "Co-segregation" also refers to the presence of two or more traits within a single plant of which at least one is known to be genetic and which cannot be readily explained by chance.

As used herein, the terms "quantitative trait locus" (QTL) and "marker trait association" refer to an association between a genetic marker and a chromosomal region and/or gene that affects the phenotype of a trait of interest. Typically, this is determined statistically; e.g., based on one or more methods published in the literature. A QTL can be a chromosomal region and/or a genetic locus with at least two alleles that differentially affect a phenotypic trait (either a quantitative trait or a qualitative trait).

As used herein, the term "genetic architecture at the QTL" refers to a genomic region which is statistically correlated to the phenotypic trait of interest and represents the underlying genetic basis of the phenotypic trait of interest.

As used herein, the phrases "sexually crossed" and "sexual reproduction" in the context of the presently disclosed subject matter refers to the fusion of gametes to produce progeny (e.g., by fertilization, such as to produce seed by pollination in plants). A "sexual cross" or "cross-fertilization" is in some embodiments fertilization of one individual by another (e.g., cross-pollination in plants). The term "selfing" refers in some embodiments to the production of seed by self-fertilization or self-pollination; i.e., pollen and ovule are from the same plant.

As used herein, the phrase "genetic marker" refers to a feature of an individual's genome (e.g., a nucleotide or a polynucleotide sequence that is present in an individual's genome) that is associated with one or more loci of interest. In some embodiments, a genetic marker is polymorphic in a population of interest, or the locus occupied by the polymorphism, depending on context. Genetic markers include, for example, single nucleotide polymorphisms (SNPs), indels (i.e., insertions/deletions), simple sequence repeats (SSRs), restriction fragment length polymorphisms (RFLPs), random amplified polymorphic DNAs (RAPDs), cleaved amplified polymorphic sequence (CAPS) markers, Diversity Arrays Technology (DArT) markers, and amplified fragment length polymorphisms (AFLPs), among many other examples. Genetic markers can, for example, be used to locate genetic loci containing alleles on a chromosome that contribute to variability of phenotypic traits. The phrase "genetic marker" can also refer to a polynucleotide sequence complementary to a genomic sequence, such as a sequence of a nucleic acid used as probes.

A genetic marker can be physically located in a position on a chromosome that is within or outside of to the genetic locus with which it is, associated (i.e., is intragenic or extragenic, respectively). Stated another way, whereas genetic markers are typically employed when the location on a chromosome of the gene or of a functional mutation, e.g. within a control element outside of a gene, that corresponds to the locus of interest has not been identified and there is a non-zero rate of recombination between the genetic marker and the locus of interest, the presently disclosed subject matter can also employ genetic markers that are physically within, the boundaries of a genetic locus (e.g., inside a genomic sequence that corresponds to a gene such as, but not limited to a polymorphism within an intron or an exon of a gene). In some embodiments of the presently disclosed subject matter, the one or more genetic markers comprise between one and ten markers, and in some embodiments the one or more genetic markers comprise more than ten genetic markers.

As used herein, the term "genotype" refers to the genetic constitution of a cell or organism. An individual's "genotype for a set of genetic markers" includes the specific alleles, for one or more genetic marker loci, present in the individual's haplotype. As is known in the art, a genotype can relate to a single locus or to multiple loci, whether the loci are related or unrelated and/or are linked or unlinked. In some embodiments, an individual's genotype relates to one or more genes that are related in that the one or more of the genes are involved in the expression of a phenotype of interest (e.g., a quantitative trait as defined herein). Thus, in some embodiments a genotype comprises a summary of one or more alleles present within an individual at one or more genetic loci of a quantitative trait. In some embodiments, a genotype is expressed in terms of a haplotype (defined herein, below).

As used herein, the term "germplasm" refers to the totality of the genotypes of a population or other group of individuals (e.g., a species). The term "germplasm" can also refer to plant material; e.g., a group of plants that act as a repository for various alleles. The phrase "adapted germplasm" refers to plant materials of proven genetic superiority; e.g., for a given environment or geographical area, while the phrases "non-adapted germplasm," "raw germplasm," and "exotic germplasm" refer to plant materials of unknown or unproven genetic value; e.g., for a given environment or geographical area; as such, the phrase "non-adapted germplasm" refers in some embodiments to plant materials that are not part of an established breeding population and that do not have a known relationship to a member of the established breeding population.

As used herein, the terms "hybrid", "hybrid plant," and "hybrid progeny" refers to an individual produced from genetically different parents (e.g., a genetically heterozygous or mostly heterozygous individual).

As used herein, the phrase "single cross $F_1$ hybrid" refers to an $F_1$ hybrid produced from a cross between two inbred lines.

As used herein, the phrase "inbred line" refers to a genetically homozygous or nearly homozygous population. An inbred line, for example, can be derived through several cycles of brother/sister breedings or of selfing or in dihaploid production. In some embodiments, inbred lines breed true for one or more phenotypic traits of interest. An "inbred", "inbred individual", or "inbred progeny" is an individual sampled from an inbred line.

As used herein, the term "dihaploid line", refers to stable inbred lines issued from anther culture. Some pollen grains (haploid) cultivated on specific medium and circumstances can develop plantlets containing n chromosomes. These plantlets are then "doubled" and contain 2n chromosomes. The progeny of these plantlets are named "dihaploid" and are essentially not segregating any more (stable).

As used herein, the term "linkage", and grammatical variants thereof, refers to the tendency of alleles at different loci on the same chromosome to segregate together more often than would be expected by chance if their transmission were independent, in some embodiments as a consequence of their physical proximity.

As used herein, the term "locus" refers to a position on a chromosome (e.g., of a gene, a genetic marker, or the like).

As used herein, the phrase "nucleic acid" refers to any physical string of monomer units that can be corresponded to a string of nucleotides, including a polymer of nucleotides (e.g., a typical DNA, cDNA or RNA polymer), modified oligonucleotides (e.g., oligonucleotides comprising bases that are not typical to biological RNA or DNA, such as 2'-O-methylated oligonucleotides), and the like. In some embodiments, a nucleic acid can be single-stranded, double-stranded, multi-stranded, or combinations thereof. Unless otherwise indicated, a particular nucleic acid sequence of the presently disclosed subject matter optionally comprises or encodes complementary sequences, in addition to any sequence explicitly indicated.

As used herein, the phrase "phenotypic trait" refers to the appearance or other detectable characteristic of an, individual, resulting from the interaction of its genome, proteome and/or metabolome with the environment.

As used herein, the phrase "resistance" refers to the ability of a plant to restrict the growth and development of a specified pest or pathogen and/or the damage they cause when compared to susceptible plants under similar environmental conditions and pest or pathogen pressure. Resistant plants may exhibit some disease symptoms or damage under heavy pest or pathogen pressure.

Essentially two levels of resistance are to be distinguished. "High or standard resistance" refers to plants that highly restrict the growth and development of the specified pest or pathogen under normal pest or pathogen pressure when compared to susceptible counterparts. These plants may, however, exhibit some symptoms or damage under heavy pest or pathogen pressure.

"Moderate/intermediate resistance" refers to plants that distract insects and/or restrict the growth and development of the specified pest or pathogen, or show reduced damage compared to susceptible counterparts but may exhibit a greater range of symptoms or damage compared to high/standard resistant plants. Moderately/intermediately resistant plants will still show significantly less severe symptoms or damage than susceptible plants when grown under similar environmental conditions and/or pest or pathogen pressure.

As used herein, the phrase "susceptibility" refers to the inability of a plant to adequately restrict the growth and development of a specified pest or, pathogen.

As used herein, the phrase "*Bemisia* resistance" or "resistance to *Bemisia* infestations" or "*Bemisia* resistant plant" refers to the plants capability to resist attack, infestation, or colonization by the insect. The level of resistance exhibited by a certain plant can be scored, for example, by means of a standardized Insect Resistance Assay as described in Example 2A herein below using a scale from 1-9 for assessing the severity of the infestation.

Plants scoring 1 in said Insect Resistance Assay are completely covered with pupae and heavily moulded often stunted in growth, whereas plants scoring 9 are completely free of pupae and thus fully resistant. A standard "susceptible variety" (e.g. Vergasa F1 or Bikingo F1) is understood for the purpose of the present invention to refer to a plant that scores in an Insect Resistance Assay as described in Example 2A between 3 and 4 where the plants show many pupae (100-

400/leaf) which are densely crowded on the leaf, usually accompanied by black mould.

A "*Bemisia* resistant plant" is understood for the purpose of the present invention to refer to a plant that scores in a standardized Insect Resistance Assay as described in Example 2A herein below in a range of between 6 and 9, including 6 and 9.

A moderate or intermediate resistance to *Bemisia* infestations starts at a score of 6 where the plants show a moderate-relatively low number of pupae (20-50/leaf) which are more regular distributed over the leaves. At a score of 7 only some pupae (5-20/leaf) are present, which are irregularly scattered over the leaf. Plants scoring 8 show only very few (1-5/leaf) pupae and are not noticeably affected in growth or fruit development.

Accordingly, for the purpose of the present invention, by a plant being "moderately or intermediately resistant" to *Bemisia* infestation, a plant is to be understood that scores in the range of between 6 and 8 on a scale ranging from 1-9 determined in a standardized Insect Resistance Assay as described in Example 2A herein below. A plant is understood to be "highly resistant" to *Bemisia*, if it scores in the range of between 8 and 9, including 9.

As used herein, the phrase "thrips resistance" or "resistance to thrips infestations" or "thrips resistant plant" refers to the plants capability to resist attack, infestation, or colonization by the insect. The level of resistance exhibited by a certain plant can be scored, for example, by means of a standardized Insect Resistance. Assay as described in Example 2B herein below using a scale from 1-9 for assessing the severity of the infestation judged on the basis of the observed feeding damage (silvering).

Plants scoring 1 in said Insect Resistance Assay show very heavy silvering with a large part of the leaf damaged (>40% silvering), whereas plants scoring 9 show no silvering damage (0% silvering) and are thus fully resistant. A standard "susceptible variety" (e.g. Roxy F1 and/or Snooker F1) is understood for the purpose of the present invention to refer to a plant that scores in an Insect Resistance Assay as described in Example 2B between 3 (11%-20% silvering) and 4 (6%-10% silvering) where the plants show many large silvering spots distributed over the entire leaf.

A "thrips resistant plant" is understood for the purpose of the present invention to refer to a plant that scores in a standardized Insect Resistance Assay as described in Example 2B herein below in a range of between 5 and 9, including 5 and 9.

A moderate or intermediate resistance to thrips infestations starts at a score of 5 where the plants show a moderate number of spots more regular distributed over the leaves (3%-5% silvering). At a score of 7 the plants show only some small spots especially near the mid vein or leaf edge (0.1%-1% silvering). Plants scoring 8 show only tiny spots and are not noticeably affected in growth or fruit development (<0.1% silvering).

Accordingly, for the purpose of the present invention, by a plant being "moderately or intermediately resistant" to thrips infestation, a plant is to be understood that scores in the range of between 5 and 8, particularly between 6 and 8, on a scale ranging from 1-9 determined in a standardized Insect Resistance Assay as described in Example 2B herein below. A plant is understood to be "highly resistant" to thrips, if it scores in the range of between 8 and 9, including 9.

The terms "chromosome 3" and "chromosome 5" are meant to include, and thus used herein synonymously with, the terms "linkage group 3 and 5" and/or "chromosome equivalent of linkage group 3 and 5", respectively.

As used herein, the term "plurality" refers to more than one. Thus, a "plurality of individuals" refers to at least two individuals. In some embodiments, the term plurality refers to more than half of the whole. For example, in some embodiments a "plurality of a population" refers to more than half the members of that population.

As used herein, the term "progeny" refers to the descendants) of a particular cross. Typically, progeny result from breeding of two individuals, although some species (particularly some plants and hermaphroditic animals) can be selfed (i.e., the same plant acts as the donor of both male and female gametes). The descendant(s) can be, for example, of the $F_1$, the $F_2$, or any subsequent generation.

As used herein, the phrase "qualitative trait" refers to a phenotypic trait that is controlled by one or a few genes that exhibit major phenotypic effects. Because of this, qualitative traits are typically simply inherited. Examples in plants include, but are not limited to, flower color, fruit color, and several known disease resistances such as, for example, Bacterial spot resistance.

"Marker-based selection" is understood within the scope of the invention to refer to e.g. the use of genetic markers to detect one or more nucleic acids from the plant, where the nucleic acid is associated with a desired trait to identify plants that carry genes for desirable (or undesirable) traits, so that those plants can be used (or avoided) in a selective breeding program.

"Microsatellite or SSRs (Simple sequence repeats) Marker" is understood within the scope of the invention to refer to a type of genetic marker that consists of numerous repeats of short sequences of DNA bases, which are found at loci throughout the plant's genome and have a likelihood of being highly polymorphic.

"PCR (Polymerase chain reaction)" is understood within the scope of the invention to refer to a method of producing relatively large amounts of specific regions of DNA or subset(s) of the genome, thereby making possible various analyses that are based on those regions.

"PCR primer" is understood within the scope of the invention to refer to relatively short fragments of single-stranded DNA used in the PCR amplification of specific regions of DNA.

"Phenotype" is understood within the scope of the invention to refer to a distinguishable characteristic(s) of a genetically controlled trait.

"Polymorphism" is understood within the scope of the invention to refer to the presence in a population of two or more different forms of a gene, genetic marker, or inherited trait or a gene product obtainable, for example, through alternative splicing, DNA methylation, etc.

"Selective breeding" is understood within the scope of the invention to refer to a program of breeding that uses plants that possess or display desirable traits as parents.

"Tester" plant is understood within the scope of the invention to refer to a plant of the genus *Capsicum* used to characterize genetically a trait, in a plant to be tested. Typically, the plant to be tested is crossed with a "tester" plant and the segregation ratio of the trait in the progeny of the cross is scored.

"Probe" as used herein refers to a group of atoms or molecules which is capable of recognising and binding to a specific target molecule or cellular structure and thus allowing detection of the target molecule or structure. Particularly, "probe" refers to a labeled DNA or RNA sequence which can be used to detect the presence of and to quantitate a complementary sequence by molecular hybridization.

The term "hybridize" as used herein refers to conventional hybridization conditions, preferably to hybridization conditions at which 5×SSPE, 1% SDS, 1×Denhardts solution is used as a solution and/or hybridization temperatures are between 35° C. and 70° C., preferably 65° C. After hybridization, washing is preferably carried out first with 2×SSC, 1% SDS and subsequently with 0.2×SSC at temperatures between 35° C. and 75° C., particularly between 45° C. and 65° C., but especially at 59° C. (regarding the definition of SSPE, SSC and Denhardts solution see Sambrook et al. loc. cit.). High stringency hybridization conditions as for instance described in Sambrook et al, supra, are particularly preferred. Particularly preferred stringent hybridization conditions are for instance present if hybridization and washing occur at 65° C. as indicated above. Non-stringent hybridization conditions for instance with hybridization and washing carried out at 45° C. are less preferred and at 35° C. even less.

"Sequence Homology or Sequence Identity" is used herein interchangeably. The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. If two sequences which are to be compared with each other differ in length, sequence identity preferably relates to the percentage of the nucleotide residues of the shorter, sequence which are identical with the nucleotide residues of the longer sequence. Sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W. R. Pearson (1990), Methods in Enzymology 183, 63-98, appended examples and http://workbench.sdsc.edu/). For this purpose, the "default" parameter settings may be used.

Another indication that two nucleic acid sequences are substantially identical is that the two molecules hybridize to each other under stringent conditions. The phrase: "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, N.Y. Generally, highly stringent hybridization and wash conditions are selected to be about 5° C. lower than the thermal melting point ($T_m$) for the specific sequence at a defined ionic strength and pH. Typically, under "stringent conditions" a probe will hybridize, to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C. with the hybridization being carried out overnight. An example of highly stringent wash conditions is 0.1 5M NaCl at 72° C. for about 15 minutes. An example of stringent wash conditions is a 0.2 times SSC wash at 65° C. for 15 minutes (see, Sambrook, infra, for a description of SSC buffer). Often, a high stringency wash is preceded by a low stringency wash to remove, background probe signal. An example medium stringency wash for a duplex of, e.g., more than 100 nucleotides, is 1 times SSC at 45° C. for 15 minutes. An example low stringency wash for a duplex of, e.g., more than 100 nucleotides, is 4-6 times SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2 times (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g. when a copy of a nucleic acid is created using the maximum codon degeneracy permitted by the genetic code.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

The present invention relates to novel pepper plants, particular to *Capsicum annuum* plants, resistant, particularly intermediately resistant, to insects, particularly to insects of the genus *Bemisia* and/or the order Thysanoptera, more particularly to *Bemisia tabaci* (white fly) and/or thrips more particularly *Frankliniella occidentalis*, further to seeds and fruits of said plants. The present invention also relates to methods of making and using such plants and their fruits.

Plants according to the invention may be obtained by crossing two or more parental genotypes, at least one of which may have one or more alleles, particularly one or more alleles at corresponding QTL contributing to *Bemisia* and/or thrips resistance, which allele(s) is/are lacking in the other parental genotype or which complements the other genotype to obtain a plant according to the invention and as described herein before. If more than one. QTL contributes to the expression of the resistance trait and the two original parental genotypes do not provide the entire set of alleles, other sources can be included in the breeding population. The other parental genotype may contribute a desirable trait including fruit quality demanded by the market such as, for example, a weight in the range of 180 grams, blocky shape, smooth skin, bright red colour. Beside fruit quality, agronomically important characteristics such as, for example, a good plant architecture, high productivity and basic resistances to disease such as, but not limited to, TMV (Tobacco Mosaic virus) and TSWV (Tomato Spotted Wilt virus) are further desired traits.

These parental genotypes may be crossed with one another to produce progeny seed. The parental genotypes may be inbred lines developed by selfing selected heterozygous plants from fields with uncontrolled or open pollination and employing recurrent selection procedures. Superior plants are selfed and selected in successive generations. In the succeeding generations the heterozygous condition gives way to homogeneous lines as a result of self-pollination and selection. With successive generations of inbreeding, the plant becomes more and more homozygous and uniform within the progeny plants. Typically, five to seven or more generations (F1 to F2; F3 to F4; F4 to F5) of selfing and pedigree selection may be practiced to obtain inbred lines that are uniform in plant and seed characteristics and that will remain uniform under continued self-fertilization.

During inbreeding, many undesirable alleles at heterozygous loci will be replaced by more favourable alleles and the unfavourable or undesired alleles eliminated from the progeny. Moreover, through marker-based selection the number of favorable alleles can be maximized in that the more unfavourable alleles are identified and successively replaced by the more favorable alleles.

In one aspect, the plant according to the invention may be obtained by introgressing the insect resistance trait from an ancestor plant, particularly a wild ancestor plant into a cultivated pepper plant; particularly a cultivated *Capsicum annuum* plant; more particularly a *Capsicum annuum* plant which is homozygous for a c locus (Blum et al. (20.02) Genome, 45: 702-705) or a pun1 allele (Stewart et al. (2005) The Plant Journal, 42: 675-688), or for both loci.

In one specific embodiment of the invention, the wild ancestor, from which the *Bemisia* and/or thrips resistance trait may be obtained, is wild *Capsicum annuum* accession no. CGN16975 obtainable from the Instituut voor de Veredeling van Tuinbouwgewassen (now: Centre for Genetic Resources), Wageningen, Netherlands. The insect resistance trait according to the present invention, which confers to a plant expressing this trait, an intermediate level of resistance to infestations with insects of the genus *Bemisia* and/or of the order Thysanoptera, more particularly to *Bemisia tabaci* (white fly) and/or thrips more particularly *Frankliniella occidentalis*, may, in the alternative, be obtained from *Capsicum annuum* line 061M4387, a sample of which has been deposited with NCIMB Ltd under accession number NCIMB 41428, or from a progeny or ancestor of line 061M4387 comprising the *Bemisia* and/or the thrips resistance trait.

Accordingly, in a specific embodiment of the invention, the parental genotype contributing the resistance trait(s) is an inbred line having the invention relevant properties of deposited *Capsicum annuum* line 061M4387, i.e. substantially the same genome architecture at the QTL associated with *Bemisia* and/or thrips resistance, seed samples of which have been deposited on Aug. 10, 2006 with NCIMB under accession number NCIMB 41428.

In another specific embodiment of the invention, the parental genotype contributing to the resistance trait is a hybrid having the invention relevant properties of deposited *Capsicum annuum* line 061M4387, i.e. substantially the same genome architecture at the QTL associated with *Bemisia* and/or thrips resistance, seed samples of which have been deposited on Aug. 10, 2006 with NCIMB under accession number NCIMB 41428.

*Capsicum annuum* line 061M4387 resulted from a cross of wild accession no CGN16975 obtainable from the Centre for Genetic Resources, Wageningen, Netherlands as the donor of the resistance trait with a *Capsicum annuum* inbred line. *Bemisia* and thrips resistant progeny of this cross was crossed, with further inbred lines of different genetic backgrounds to finally obtain line 061M4387.

Accordingly, *Capsicum annuum* line 061M4387 or any other plant line containing the *Bemisia* and/or thrips resistance trait of *Capsicum annuum* line 061M4387, may be used as a source material for introgressing said resistance trait into any desired genetic background to obtain a pepper plant being highly or intermediately resistant, particularly intermediately resistant, to infestations with insects of the genus *Bemisia* and/or of the order Thysanoptera, more particularly to *Bemisia tabaci* (white fly) and/or thrips more particularly *Frankliniella occidentalis*, may further contain one or more desirable traits such as fruit quality traits demanded by the market such as, for example, a weight in the range of 180 grams, blocky shape, smooth skin, bright red colour. Beside fruit quality, agronomically important characteristics such as, for example, a good plant architecture, high productivity and basic resistances to disease such as, but not limited to, TMV (Tobacco Mosaic virus) and TSWV (Tomato Spotted Wilt virus) are further desired traits.

Based on the description of the present invention, the skilled person who is in possession of *Capsicum annuum* line 061M4387, a sample of which has been deposited with NCIMB Ltd under accession number NCIMB 41428, or of a progeny or ancestor thereof containing the QTL on chromosome 3 associated, with resistance to *Bemisia* and/or the QTL on chromosome 5 associated with resistance to thrips and

*Bemisia*, respectively, as described herein above, has no difficulty to transfer the *Bemisia* resistance trait and/or the thrips resistance trait of the present invention to other pepper plants of various types using breeding techniques well-known in the art. The trait of the present invention may for example, be transferred to pepper plants producing fruit of various types or shapes, such as bell peppers, sweet peppers, hot peppers, big rectangular peppers, conical peppers, including long conical peppers, or blocky-type peppers and of various mature colors, such as evergreen, red, yellow, orange or ivory. Accordingly, in one embodiment, a plant of the present invention is a *C. annuum* plant capable of resisting infestations with *Bemisia* and/or thrips, which plant is a bell pepper or sweet pepper, a hot pepper, a big rectangular pepper, a conical pepper or a long conical pepper according to the instant invention. In one embodiment, a plant of the present invention is capable of producing an evergreen, a red, yellow, orange or ivory pepper fruit. In another embodiment of the invention, the pepper plants are grown for (hybrid) seed or commercial pepper production.

Accordingly, in another embodiment, the present invention discloses a method of transferring the *Bemisia* resistance trait and/or the thrips resistance trait according to the present invention to a pepper plant lacking said trait comprising a) obtaining a plant comprising said trait; b) crossing it to a plant lacking said trait; c) obtaining plants of the cross of step b); d) selecting a plant of step c) which is capable of resisting infestations with *Bemisia* and/or thrips according to the present invention. In one embodiment, the method further comprises e) back-crossing a plant resulting from step d) with a pepper plant, and f) selecting for a pepper plant, which is capable of resisting infestations with *Bemisia* and/or thrips according to the present invention. In one embodiment, the method further comprises obtaining an inbred pepper plant, which is capable of resisting infestations with *Bemisia* and/or thrips according to the present invention, and, in one embodiment, the method further comprises crossing said inbred pepper plant to another pepper plant to produce a hybrid pepper plant, which is capable of resisting infestations with *Bemisia* and/or thrips according to the present invention. In one embodiment, a pepper plant is selected by determining the resistance score to *Bemisia* and/or thrips infestations, as described herein. In one embodiment, the plant of step a) comprising said trait is *Capsicum annuum* line 061M4387, a sample of which has been deposited with NCIMB Ltd under accession number NCIMB 41428, or a progeny or ancestor of said plant.

In certain embodiments of the invention, a standardized Insect Resistance Assay is used, such as that described in Example 2 herein below, to determine the resistance level of the progeny plants resulting from one of the above crosses and to select those progeny plants for further breeding which are intermediately resistant, to *Bemisia* and/or thrips infestations.

In one embodiment, the present invention discloses a *C. annuum* plant obtainable by any one of the methods above, wherein the plant is capable of resisting infestations with *Bemisia* and/or thrips as described herein.

In yet another embodiment, the present invention discloses a method of producing a plant comprising the *Bemisia* and/or the thrips resistance trait according to the present invention to a pepper plant lacking said trait comprising a) obtaining a plant comprising said trait; b) crossing it to a plant lacking said trait; c) obtaining plants of the cross of step b); d) selecting a plant of step c) which is capable of resisting infestations with *Bemisia* and/or thrips according to the present invention. In one embodiment, the method further comprises e) back-crossing a plant resulting from step d) with a pepper plant, and f) selecting for a pepper plant, which is capable of resisting infestations with *Bemisia* and/or thrips according to the present invention. In one embodiment, the method further comprises obtaining an inbred pepper plant, which is capable of infestations with *Bemisia* and/or thrips according to the present invention, and, in one embodiment, the method further comprises crossing said inbred pepper plant to another pepper plant to produce a hybrid pepper plant, which is capable of resisting infestations with *Bemisia* and/or thrips according to the present invention. In one embodiment, a pepper plant is selected by determining the resistance score to *Bemisia* and/or thrips infestations, as described herein. In one embodiment, the plant of step a) comprising said trait is *Capsicum annuum* line 061M4387, a sample of which has been deposited with NCIMB Ltd under accession number NCIMB 41428, or a progeny or ancestor of said plant.

In one embodiment, the present invention discloses a *C. annuum* plant obtainable by any one of the methods above, wherein the plant is capable of resisting infestations with *Bemisia* and/or thrips as described herein.

Based on the teachings of the present invention, a skilled person can design a program to look for new sources for a trait, particularly a resistance trait, but especially a resistance to insects of the genus *Bemisia* and/or of the order Thysanoptera.

In one aspect of the invention, plants expressing the insect resistant trait and exhibiting resistance, particularly an intermediate level of resistance, to infections with insects of the genus *Bemisia*, may be identified and selected by using a standardized *Bemisia* resistant test resulting in a resistance rating which is commonly used and recognized in the art of pepper breeding.

In particular, plants are raised and cultivated according to standard procedures and transplanted according to a special design.

Plants are transplanted in several rows with a fixed number of plants per row. In each row one side is used as spreader row and planted with a susceptible entry or, susceptible parental line. The other part of the row is planted with the entries to be tested for insect resistance. The test entries are fully randomized in each of several blocks, with 1 or more plants/entry per block.

*Bemisia* development is monitored in the spreader row weekly or biweekly by assessing a fixed number of spreader row plants on equidistant positions (for example, plant 1, 38, 75, 112, 150) in each row. The final assessments are made when the average infestation of the monitored spreader plants has reached a resistance rating of approx. 4, that is when the pupae are densely crowded on the leaf in numbers of more than 100/leaf. Usually; this stage is reached at the time when the first fruits are ripening (3-4 months after transplantation).

Data are analyzed by calculating the means per test entry and comparison with a susceptible entry (e.g. susceptible spreader row or else). A multiple comparison of the means (e.g. LSD) indicates if test entries differ mutually and from a susceptible control.

For assessing the severity, a scale from 1-9 is used (Table 1). The abaxial side of the leaves of the plant is inspected and the average of the ca. 5 worst affected leaves is assessed according the 1-9 scale. All test plants are scored in this way.

In one aspect of the invention, plants expressing the insect resistant trait and exhibiting resistance, particularly an intermediate level of resistance, to infections with, insects of the order Thysanoptera may be identified and selected by using a standardized thrips resistant test resulting in a resistance rating which is commonly used and recognized in the art of pepper breeding.

In particular, plants are raised, and cultivated according to standard procedures and transplanted according to a special design.

In the alternative, marker-assisted breeding may be employed to identify those individuals where invention relevant loci, particularly invention relevant QTL loci, and/or flanking marker lad or marker loci genetically linked thereto, as described herein before have favorable genotypes, particularly homozygous favorable genotypes.

In one embodiment of the invention, resistance to *Bemisia* and/or thrips infestation is recorded in phenotypic evaluation.

In another embodiment, selection is based on molecular markers, which, are linked to traits of interest.

In one embodiment, selection is based on a combination of molecular markers and phenotypic evaluation.

Marker-based selection may already be used in the early phases of inbred development, often in combination with screening methods which are based largely on phenotypic characteristics that can be determined visually and are related to key performance indices such as, for example, plant vigor, length of internodes, ramifications, insect resistance such as resistance to *Bemisia* and/or thrips infestations, virus resistances such as TMV (Tobacco Mosaic virus) and TSWV (Tomato Spotted wilt virus), etc., which are relevant for the suitability of the plant to be utilized in commercial hybrid production. Selection may also be based on molecular markers, which may or may not be linked to traits of interest.

In particular, marker-based selection may be applied in combination with or followed by a phenotypic selection to identify those individuals where all of the invention relevant loci described herein before have homozygous favorable genotypes.

There are several types of molecular markers that may be used in marker-based selection including, but not limited to, restriction fragment length polymorphism (RFLP), random amplification of polymorphic. DNA (RAPD), amplified restriction fragment length polymorphism (AFLP), single sequence repeats (SSR) and single nucleotide polymorphisms SNPs.

RFLP involves the use of restriction enzymes to cut chromosomal DNA at specific short restriction sites, polymorphisms result from duplications or deletions between the sites or mutations at the restriction sites.

RAPD utilizes low stringency polymerase chain reaction (PCR) amplification with single primers of arbitrary sequence to generate strain-specific arrays of anonymous DNA fragments. The method requires only tiny DNA samples and analyses a large number of polymorphic loci.

AFLP requires digestion of cellular DNA with a restriction enzyme(s) before using PCR and selective nucleotides in the primers to amplify specific fragments. With this method, using electrophoresis techniques to visualize the obtained fragments, up to 100 polymorphic loci can be measured per primer combination and only small DNA sample are required for each test.

SSR analysis is based on DNA micro-satellites (short-repeat) sequences that are widely dispersed throughout the genome of eukaryotes, which are selectively amplified to detect variations in simple sequence repeats. Only tiny DNA samples are required for an SSR analysis. SNPs use PCR extension assays that efficiently pick up point mutations. The procedure requires little DNA per sample. One or two of the above methods may be used in a typical marker-based selection breeding program.

The most preferred method of achieving amplification of nucleotide fragments that span a polymorphic region of the plant genome employs the polymerase chain reaction ("PCR") (Mullis et al., Cold Spring Harbor Symp. Quant. Biol. 51:263 273 (1986)), using primer pairs involving a forward primer and a backward primer that are capable of hybridizing to the proximal sequences that define a polymorphism in its double-stranded form.

Alternative methods may be employed to amplify fragments, such as the "Ligase Chain Reaction" ("LCR") (Barany, Proc. Natl. Acad. Sci. (U.S.A.) 88:189 193 (1991)), which uses two pairs of oligonucleotide probes to exponentially amplify a specific target. The sequences of each pair of oligonucleotides are selected to permit the pair to hybridize to abutting sequences of the same strand of the target. Such hybridization forms a substrate for a template-dependent ligase. As with PCR, the resulting products thus serve as a template in subsequent cycles and an exponential amplification of the desired sequence is obtained.

LCR can be performed with oligonucleotides having the proximal and distal sequences of the same strand of a polymorphic site. In one embodiment, either oligonucleotide will be designed to include the actual polymorphic site of the polymorphism. In such an embodiment, the reaction conditions are selected such that the oligonucleotides can be ligated together only if the target molecule either contains or lacks the specific nucleotide that is complementary to the polymorphic site present on the oligonucleotide. Alternatively, the oligonucleotides may be selected such that they do not include the polymorphic site (see, Segev, PCT Application WO 90/01069).

A further method that may alternatively be employed is the "Oligonucleotide Ligation Assay" ("OLA") (Landegren et al., Science 241:1077 1080 (1988)). The OLA protocol uses two oligonucleotides that are designed to be capable of hybridizing to abutting sequences of a single strand of a target. OLA, like LCR, is particularly suited for the detection of point mutations. Unlike LCR, however, OLA results in "linear" rather than exponential amplification of the target sequence.

Still another method that may alternatively be employed is the "Invader Assay" that uses a structure-specific flap endonuclease (FEN) to cleave a three-dimensional complex formed by hybridization of allele-specific overlapping oligonucleotides to target DNA containing a single nucleotide polymorphism (SNP) site. Annealing of the oligonucleotide complementary to the SNP allele in the target molecule triggers the cleavage of the oligonucleotide by cleavase, a thermostable FEN. Cleavage can be detected by several different approaches. Most commonly, the cleavage product triggers a secondary cleavage reaction on a fluorescence resonance energy transfer (FRET) cassette to release a fluorescent signal. Alternatively, the cleavage can be detected directly by use of fluorescence polarization (FP) probes, or by mass spectrometry. The invasive cleavage reaction is highly specific, has a low failure rate, and can detect zeptomol quantities of target DNA. While the assay traditionally has been used to interrogate one SNP in one sample per reaction, novel chip- or bead-based approaches have been tested to make this efficient and accurate assay adaptable to multiplexing and high-throughput SNP genotyping.

Nickerson et al. have described a nucleic acid detection assay that combines attributes of PCR and OLA (Nickerson et al., Proc. Natl. Acad. Sci. (U.S.A.) 87:8923 8927 (1990)). In this method, PCR is used to achieve the exponential amplification of target. DNA, which is then detected using OLA.

Schemes based on ligation of two (or more) oligonucleotides in the presence of a nucleic acid having the sequence of the resulting "di-oligonucleotide", thereby amplifying the di-oligonucleotide, are also known (Wu et al., Genomics 4:560 569 (1989)), and may be readily adapted to the purposes of the present invention.

In one embodiment, a molecular marker is a DNA fragment amplified by PCR, e.g. a SSR marker or a RAPD marker. In one embodiment, the presence or absence of an amplified DNA fragment is indicative of the presence or absence of the trait itself or of a particular allele of the trait. In one embodiment, a difference in the length of an amplified DNA fragment is indicative of the presence of a particular allele of a trait, and thus enables to distinguish between different alleles of a trait.

In a specific embodiment of the invention simple sequence repeat (SSR) markers are used to identify invention-relevant alleles in the parent plants and/or the ancestors thereof, as well as in the progeny plants resulting from a cross of said parent plants. Simple sequence repeats are short, repeated DNA sequences and present in the genomes of all eukaryotes and consists of several to over a hundred repeats of a given nucleotide motif. Since the number of repeats present at a particular location in the genome often differs among plants, SSRs can be analyzed to determine the absence or presence of specific alleles.

In another embodiment of the invention SNP markers are used to identify invention-relevant alleles in the parent plants and/or the ancestors thereof, as well as in the progeny plants resulting from a cross of said parent plants.

In one aspect, the invention relates to a marker or a set of two or more markers and up to 6 markers comprising a pair of PCR oligonucleotide primers consisting of a forward primer and a reverse primer selected from the group of primer pair 1 represented by a forward primer of SEQ ID NO: 1 and a reverse primer of SEQ ID NO: 2, primer pair 2 represented by a forward primer of SEQ ID NO: 3 and a reverse primer of SEQ ID NO: 4, primer pair 3 represented by a forward primer of SEQ ID NO: 5 and a reverse primer of SEQ ID NO: 6, primer pair 4 represented by a forward primer of SEQ ID NO: 7 and a reverse primer of SEQ ID NO: 8, primer pair 5 represented by a forward primer of SEQ ID NO: 9 and a reverse primer of SEQ ID NO: 10, and primer pair 6 represented by a forward primer of SEQ ID NO: 11 and a reverse primer of SEQ ID NO: 12, which primers lead to an amplification product in a PCR reaction exhibiting a molecular weight or a nucleotide sequence, which is essentially identical or can be considered as an allele to that of a corresponding PCR amplification product obtainable from *Capsicum annuum* line 061M4387 in a PCR reaction with the identical primer pair(s).

Any other combination of forward and reverse primers selected from the group of primer sequences depicted in SEQ ID NOs: 1-12 may also be used in a PCR reaction.

In one aspect, the invention relates to a marker or a set of two or more markers and up to 7 markers comprising a pair of PCR oligonucleotide primers consisting of a forward primer and a reverse primer selected from the group of primer pair 7 represented by a forward primer of SEQ ID NO: 13 and a reverse primer of SEQ ID NO: 14, identifying marker locus 7; primer pair 8 represented by a forward primer of SEQ ID NO: 15 and a reverse primer of SEQ ID NO: 16, identifying marker locus 8; primer pair 9 represented by a forward primer of SEQ ID NO: 17 and a reverse primer of SEQ ID NO: 18, identifying marker locus 9; primer pair 10 represented by a forward primer of SEQ ID NO: 19 and a reverse primer of SEQ ID NO: 20, identifying marker locus 10; primer pair 11 represented by a forward primer of SEQ ID NO: 21 and a reverse primer of SEQ ID NO: 22, identifying marker locus 11; primer pair 12 represented by a forward primer of SEQ ID NO: 23 and a reverse primer of SEQ ID NO: 24, identifying marker locus 12, and primer pair 13 represented by a forward primer of SEQ ID NO: 25 and a reverse primer of SEQ ID NO: 26, identifying marker locus 13, which primers lead to an amplification product in a PCR reaction exhibiting a molecular weight or a nucleotide sequence, which is essentially identical or can be considered as an allele to that of a corresponding PCR amplification product obtainable from *Capsicum annuum* line 061M4387 in a PCR reaction with the identical primer pair(s).

Any other combination of forward and reverse primers selected from the group of primer sequences depicted in SEQ ID NOs: 13-26 may also be used in a PCR reaction.

In one aspect, the invention relates to a Marker or as set of two or more markers and up to 13 markers comprising a pair of PCR oligonucleotide primers consisting of a forward and a reverse primer selected from the group of primer pair 1 represented by a forward primer of SEQ ID NO: 1 and a reverse primer of SEQ ID NO: 2, primer pair 2 represented by a forward primer of SEQ ID NO: 3 and a reverse primer of SEQ ID NO: 4, primer pair 3 represented by a forward primer of SEQ ID NO: 5 and a reverse primer of SEQ ID NO: 6, primer pair 4 represented by a forward primer of SEQ ID NO: 7 and a reverse primer of SEQ ID NO: 8, primer pair 5 represented by a forward primer of SEQ ID NO: 9 and a reverse primer of SEQ ID NO: 10, and primer pair 6 represented by a forward primer of SEQ ID NO: 11 and a reverse primer of SEQ ID NO: 12, primer pair 7 represented by a forward primer of SEQ ID NO: 13 and a reverse primer of SEQ ID NO: 14, identifying marker locus 7; primer pair 8 represented by a forward primer of SEQ ID NO: 15 and a reverse primer of SEQ ID NO: 16, identifying marker locus 8; primer pair 9 represented by a forward primer of SEQ ID NO: 17 and a reverse primer of SEQ ID NO: 18, identifying marker locus 9; primer pair 10 represented by a forward primer of SEQ ID NO: 19 and a reverse primer of SEQ ID NO: 20, identifying marker locus 10; primer pair 11 represented by a forward primer of SEQ ID NO: 21 and a reverse primer of SEQ ID NO: 22, identifying, marker locus 11; primer pair 12 represented by a forward primer of SEQ ID NO: 23 and a reverse primer of SEQ ID NO: 24, identifying marker locus 12, and primer pair 13 represented by a forward primer of SEQ ID NO: 25 and a reverse primer of SEQ ID NO: 26, identifying marker locus 13, which primers lead to an amplification product in a PCR reaction exhibiting a molecular weight or a nucleotide sequence, which is essentially identical or can be considered as an allele to that of a corresponding PCR amplification product obtainable from *Capsicum annuum* line 061M4387 in a PCR reaction with the identical primer pair(s).

Any other combination of forward and reverse primers selected, from the group of primer sequences depicted in SEQ ID NOs: 1-26 may also be used in a PCR reaction.

In another embodiment of, the invention, molecular markers may be used that are in linkage disequilibrium and/or linked to and/or located in the QTL region on chromosome 3 and chromosome 5, respectively comprising a QTL contributing to *Bemisia* and thrips resistance according to the invention, as well as a markers that represent the actual causal mutations underlying the QTL, and thus exhibits statistical correlation to the phenotypic trait, which markers can be developed using the oligonucleotide primers as disclosed in SEQ ID NO: 1-12 and SEQ ID NOs: 13 to 26, respectively.

In a first step, DNA or cDNA samples are obtained from suitable plant material such as leaf tissue by extracting DNA, or RNA using known techniques. Primers that flank a region containing SSRs within the invention-relevant QTL disclosed herein before or within a region, linked thereto, are then used to amplify the DNA sample using the polymerase chain reaction (PCR) method well-known to those skilled in the art.

Basically, the method, of PCR amplification involves use of a primer or a pair of primers comprising two short oligonucleotide primer sequences flanking the DNA segment to be amplified or adapter sequences ligated to said DNA segment. Repeated cycles of heating and denaturation of the DNA are followed by annealing of the primers to their complementary sequences at low temperatures, and extension of the annealed primers with DNA polymerase. The primers hybridize to opposite strands of the DNA target sequences. Hybridization refers to annealing of complementary DNA strands, where complementary refers to the sequence of the nucleotides such that the nucleotides of one strand can bond with the nucleotides on the opposite strand to form double stranded structures. The primers are oriented so that DNA synthesis by the polymerase proceeds bidirectionally across the nucleotide sequence between the primers. This procedure effectively doubles the amount of that DNA segment in one cycle. Because the PCR products are complementary to, and capable of binding to, the primers, each successive cycle doubles the amount of DNA synthesized in the previous cycle. The result of this procedure is exponential accumulation of a specific target fragment, that is approximately $2^{<n>}$, where n is the number of cycles.

Through PCR amplification millions of copies of the DNA segment flanked by the primers are made. Differences in the number of repeated sequences or insertions or deletions in the region flanking said repeats, which are located between the flanking primers in different alleles are reflected in length variations of the amplified DNA fragments. These variations can be detected, for example, by electrophoretically separating the amplified DNA fragments on gels or by using capillary sequencer. By analyzing the gel or profile, it can be determined whether the plant contains the desired allele in a homozygous or heterozygous state or whether the desired or undesired allele is absent from the plant genome.

Marker analysis can be done early in plant development using DNA samples extracted from leaf tissue of very young plants or from seed. This allows to identify plants with a desirable genetic make-up early in the breeding cycle and to discard plants that do not contain the desired, invention-relevant alleles prior to pollination thus reducing the size of the breeding population and reducing the requirements of phenotyping.

Further, by using, molecular markers, a distinction can be made between homozygous plants that carry two copies of the desired, invention-relevant allele at invention-relevant. QTL loci and heterozygous plants that carry only one copy and plants that do not contain any copy of the favourable allele(s).

In one embodiment, of the invention, the marker loci can be identified by a pair of PCR oligonucleotide primers consisting of a forward primer and, a reverse primer selected from the group of primer pair 1 represented by a forward primer of SEQ ID NO: 1 and a reverse primer of SEQ ID NO: 2, primer pair 2 represented by a forward primer of SEQ ID NO: 3 and a reverse primer of SEQ ID NO: 4, primer pair 3 represented by a forward primer of SEQ ID NO: 5 and a reverse primer of SEQ ID NO: 6, primer pair 4 represented by a forward primer of SEQ ID NO: 7 and a reverse primer of SEQ ID NO: 8, primer pair 5 represented by a forward primer of SEQ ID NO: 9 and a reverse primer of SEQ ID NO: 10, and primer pair 6 represented by a forward primer of SEQ ID NO: 11 and a reverse primer of SEQ ID NO: 12, including oligonucleotide primers consisting of a forward primer and a reverse primer exhibiting a nucleotide sequences that share between 90% and 99%, particularly between 95% and 98% sequence identity with the nucleotide sequences given in SEQ ID NO: 1-12.

In one embodiment of the invention, the marker loci can be identified by a pair of PCR oligonucleotide primers consisting of a forward primer and a reverse primer selected from the group of primer pair 7 represented by a forward primer of SEQ ID NO: 13 and a reverse primer of SEQ ID NO: 14, identifying marker locus 7; primer pair 8 represented by a forward primer of SEQ ID NO: 15 and a reverse primer of SEQ ID NO: 16, identifying marker locus 8; primer pair 9 represented by a forward primer of SEQ ID NO: 17 and a reverse primer of SEQ ID NO: 18, identifying marker locus 9; primer pair 10 represented by a forward primer of SEQ ID NO: 19 and a reverse primer of SEQ ID NO: 20, identifying marker locus 10; primer pair 11 represented by a forward primer of SEQ ID NO: 21 and a reverse primer of SEQ ID NO: 22, identifying marker locus 11; primer pair 12 represented by a forward primer of SEQ ID NO: 23 and a reverse primer of SEQ ID NO: 24, identifying marker locus 12, and primer pair 13 represented by a forward primer of SEQ ID NO: 25 and a reverse primer of SEQ ID NO: 26, identifying marker locus 13, including oligonucleotide primers consisting of a forward primer and a reverse primer exhibiting a nucleotide sequences that share between 90% and 99%, particularly between 95% and 98% sequence identity with the nucleotide sequences given in SEQ ID NO: 13-26.

Further can be used within the scope of the invention oligonucleotide molecules such as primers or probes, particularly primers consisting of a forward primer and a reverse primer exhibiting a nucleotide sequences that hybridize to the nucleotide sequences of the forward and reverse primer sequences given in SEQ ID NO: 1-12 shown in Table 10 and in SEQ ID NO: 13-26 shown in Table 11, or to nucleotide sequences that hybridize to a sequence which can be obtained by using forward and reverse primer sequences as given in SEQ ID NO: 1-12 and SEQ ID NO: 13-26, respectively, under medium, particularly under medium to high, particularly under high stringency conditions.

In particular, the hybridization reaction is carried out under high stringency conditions at which 5×SSPE, 1% SDS, 1×Denhardts solution is used as a solution and/or hybridization temperatures are between 35° C. and 70° C., and up to 72° C., preferably 65° C. After hybridization, washing is particularly carried out first with 2×SSC, 1% SDS and subsequently with 0.2×SSC at temperatures between 35° C. and 70° C., and up to 72° C., particularly at 65° C. (regarding the definition of SSPE, SSC and Denhardts solution see Sambrook et al. loc. cit.).

In one aspect of the invention, markers maybe developed and used which are not explicitly disclosed herein or markers even yet to be identified. Based on the information provided in this application it will be possible, for a skilled person, to identify or develop markers not explicitly disclosed but linked to the QTL or linked to the markers disclosed. The skilled person knows that other markers may provide at least equal utility in marker assisted selection.

The invention thus also relates to molecular markers that are in linkage disequilibrium and/or linked to and/or located in the QTL region on chromosome 3 and chromosome 5, respectively comprising a QTL contributing to *Bemisia* and thrips resistance according to the invention, as well as a markers that represent the actual causal mutations underlying the QTL, and thus exhibits statistical correlation to the phenotypic trait, which markers can be developed using the oligonucleotide primers as disclosed in in SEQ ID NO: 1-12 and SEQ ID NOs: 13 to 26, respectively.

The contiguous genomic markers that indicate the location of the QTL on the genome are in principal arbitrary or non-limiting. In general, the location of a QTL is indicated by a contiguous string of markers that exhibit statistical correlation to the phenotypic trait. Thus it is possible to indicate the location of the QTL and the presence or absence of the QTL (and with that the phenotype) by other markers located within the QTL region.

The number of potentially useful markers is limited, but may be very large, and a skilled person may easily identify additional markers to those disclosed in the application. Any marker that is linked to the resistance as disclosed in the application can be used in marker assisted selection.

Thus, alternative markers can therefore be developed by methods known to the skilled person and used to identify and select plants with an allele or a set, of alleles of a quantitative trait locus or loci according to the present invention and as disclosed herein before.

For example, the nucleotide sequence of the amplification product obtained in PCR amplification using the primer pairs as indicated in Table 10 and Table 11, respectively, exhibiting a nucleotide sequence as given in SEQ ID NO: 1-12 and SEQ ID NOs: 13-26, can be obtained by those skilled in the art and new primers or primer pairs designed based on the newly determined nucleotide sequence of the PCR amplification product. Furthermore, the markers according to the invention and disclosed herein before could be positioned on a genetic map of pepper or other species, in particular Solanaceae species and known markers mapping in the same or homolog or ortholog region(s) could be used as starting point for developing new markers.

The nucleotide sequences of the amplification products obtained in PCR amplification using the primer pairs as indicated in Table 10 and Table 11, respectively, exhibiting a nucleotide sequence as given in SEQ ID NO: 1-12 and SEQ ID NOs: 13-26, or part thereof can also be used as hybridization probes, for example to screen a BAC library, to identify additional linked nucleotide sequences.

Accordingly, the markers specifically disclosed in the present invention may also be used in, the identification and/or development of new or additional markers associated, with the QTL of interest, which in turn can then be used in marker assisted breeding and/or the search of recombinants flanking the QTL, and/or fine-mapping, and/or cloning of the QTL.

There are several methods or approaches available, known to those skilled in the art, which can be used to identify and/or develop markers in linkage disequilibrium and/or linked to and/or located in the QTL region, as well as markers that represent the actual causal mutations underlying the QTL. Without being fully exhaustive some approaches, known by those skilled in the art, include:

use of disclosed sequences/markers in hybridization approaches to identify other sequence in the region of interest: primer sequences as disclosed herein and/or marker/gene sequences (or part thereof) that can be determined using the primer sequences as disclosed herein may be used as (hybridization) probes in isolating nucleic acid sequences/genes flanking the markers and/or linked and/or associated and/or specific for the QTL region from a genomic nucleic acid sample and/or RNA or cDNA sample or pool of samples (for example screening of genomic resources like BAC libraries or gDNA or cDNA library screening).

use of disclosed sequences/markers in PCR approaches to identify other sequence in the region of interest: primer sequences as disclosed herein and/or marker/(candidate)gene sequences (or part thereof) that can be determined using the primer sequences as disclosed may be used as (PCR) amplification primers to amplify a nucleic acid sequence/gene flanking and/or linked to and/or associated with and/or specific for the QTL region from a genomic nucleic acid sample and/or RNA or cDNA sample or pool of samples either or not isolated from a specific plant tissue and/or after specific treatment of the plant and from capsicum or in principal any other organism with sufficient homology.

use of disclosed sequences/markers in PCR approaches to identify other sequence in the region of interest: the nucleotide sequences/genes of one or more markers can be determined after internal primers for said marker sequences may be designed and used to further determine additional flanking sequence/genes within the QTL region and/or genetically linked and/or associated with the trait.

use of disclosed sequences/markers in mapping and/or comparative mapping approaches to identify markers in the same region(s) (positioning of QTL on other maps): based on positional information and/or marker information as disclosed herein, markers, of any type, may be identified by genetic mapping approaches, eventually (if already needed) by positioning of the disclosed markers (by genetic mapping or extrapolation based on common markers across maps) on a (high density) genetic map(s), and/or integrated genetic or consensus map(s). Markers already known and/or new markers genetically linked and/or positioned in the vicinity of the disclosed markers and/or QTL region may be identified and/or obtained and eventually used in QTL (fine-)mapping and/or QTL cloning and/or MAS breeding applications.

use of disclosed Sequences/markers in 'in-siloco' approaches to identify additional sequences/markers/(candidate)genes in region(s): primer sequences as disclosed herein and/or marker/(candidate)gene sequences (or part thereof) that can be determined using the primer sequences as disclosed herein or based on linked markers may be used in 'in-silico' methods to search sequence or protein databases (e.g. BLAST) for (additional) flanking and/or homolog sequences/genes and/or allelic diversity (both genomic and/or cDNA sequences or even proteins and both originating from capsicum and/or any other organism) genetically linked and/or associated with the traits as described herein and/or located in the QTL region.

use of disclosed sequences/markers in physical mapping approaches (positioning of QTL on physical map or genome sequence): primer sequences as disclosed herein and/or marker/gene sequences (or part thereof) that can be determined using the primer sequences as disclosed herein or using other markers genetically linked to the markers disclosed herein and/or located in the QTL region may be positioned on a physical map and/or (whole) genome sequence in principal of any organism with sufficient homology to identify (candidate) sequences/markers/genes applicable in QTL(fine-mapping) and/or QTL cloning and/or MAS breeding applications.

use of disclosed sequences/markers to position QTL on other (physical) maps or genomes (across species . . . for pepper other Solanaceae as tomato and potato are of first interest of course but model species like *Arabidopsis* may be used): primer sequences as disclosed herein and/or marker/gene sequences (or part thereof) that can be determined using the primer sequences as disclosed herein may be used in comparative genome or syntheny mapping approaches to identify homolog region and homolog and/or ortholog sequences/(candidate)genes genetically linked and/or positioned in the QTL region and applicable in QTL(fine-mapping) and/or QTL cloning and/or MAS breeding applications.

use of disclosed sequences/markers to select the appropriate individuals allowing the identification of markers in region of interest by genetic approaches: primer sequences and/or markers as disclosed herein may be used to select individuals with different/contrasting QTL alleles which in for example in genetic association approaches and/or bulk segregant analysis (BSA, Michelmore et al., 1991) can be used to identify markers/genes in the specific region (QTL region) of interest and/or associated or genetically linked to the described traits.

use of disclosed information to search for (positional) candidate genes: the disclosed information may be used to identify positional and/or functional candidate genes which may be associated with the described traits and/or genetically linked.

In one embodiment, the invention therefore relates to a cultivated *Capsicum annuum* plant comprising a genome comprising at least one QTL which contributes to *Bemisia* resistance, which QTL is located on chromosome 3, wherein said at least one. QTL can be identified by a molecular marker that exhibit statistical correlation to the phenotypic trait, which marker can be developed from a DNA segment containing said QTL by methods known in the art, which segment is obtainable from a plant which has the genetic background of line 061M4387, particularly from a plant which has the genetic background or architecture at the QTL of line 061M4387, but especially from a plant of line 061M4387, representative seed of which is deposited at NCIMB under Accession. No. NCIMB 41428, or from a progeny or an ancestor thereof comprising said QTL, and defined by at least one marker locus, particularly to at least two marker loci, more particularly to at least three marker loci and even more particularly to at least four marker loci, but especially to at least five and up to six marker loci, which marker loci are on chromosome 3 and co-segregate with the *Bemisia* resistance trait and can be identified by a PCR oligonucleotide primer or a pair of PCR oligonucleotide primers selected from the group of primer pair 1 represented by a forward primer of SEQ ID NO: 1 and a reverse primer of SEQ ID NO: 2, identifying marker locus 1; primer pair 2 represented by a forward primer of SEQ ID NO: 3 and a reverse primer of SEQ ID NO: 4, identifying marker locus 2; primer pair 3 represented by a forward primer of SEQ ID NO: 5 and a reverse primer of SEQ ID NO: 6, identifying marker locus 3; primer pair 4 represented by a forward primer of SEQ ID NO: 7 and a reverse primer of SEQ ID NO: 8, identifying marker locus 4; primer pair 5 represented by a forward primer of SEQ ID NO: 9 and a reverse primer of SEQ ID NO: 10, identifying marker locus 5; and primer pair 6 represented by a forward primer of SEQ ID NO: 11 and a reverse primer of SEQ ID NO: 12, identifying marker locus 6.

In one embodiment, the invention therefore relates to a cultivated *Capsicum annuum* plant comprising a genome comprising at least two QTL which contribute to *Bemisia* resistance, which QTL are located on chromosome 3 and 5, wherein said at least two QTL can be identified by a molecular marker that exhibit statistical correlation to the phenotypic trait, which marker can be developed from a DNA segment containing said QTL by methods known in the art, which segment is obtainable from a plant which has the genetic, background of line 061M4387, particularly from a plant which has the genetic background or architecture at the QTL of line 061M4387, but especially from a plant of line 061M4387, representative seed of which is deposited at NUMB under Accession No. NCIMB 41428, or from a progeny or an ancestor thereof comprising said QTL, wherein a first QTL is located on chromosome 3 in the donor plant and genetically linked to at least one marker locus, particularly to at least two marker loci, particularly to at least three marker loci and particularly to at least four marker loci, particularly to at least five marker loci, particularly to at least six marker loci, which marker loci are on chromosome 3 and co-segregate with the *Bemisia* resistance trait and can be identified by a pair of PCR oligonucleotide primers 1 to 6 as given in SEQ ID NOs: 1 to 12 and wherein a second QTL is located on chromosome 5 in the donor plant and genetically linked to at least one marker locus, particularly to at least two marker loci, particularly to at least three marker loci and particularly to at least four marker loci, particularly to at least five marker loci, particularly to at least six marker loci, and up to seven marker loci, which marker loci are on chromosome 5 and co-segregate with the *Bemisia* resistance trait and can be identified by a pair of PCR oligonucleotide primers selected from the group of primer pairs 7 to 13 as given in SEQ ID NOs: 13 to 26.

In one embodiment, the invention relates to a cultivated *Capsicum annuum* plant comprising a genome comprising at least one QTL which contributes to thrips resistance, which QTL is located on chromosome 5, wherein said at least one QTL can be identified by a molecular marker that exhibit statistical correlation to the phenotypic trait, which marker can be developed from a DNA segment containing said QTL by methods known in the art, which segment is obtainable from a plant which has the genetic background of line 061M4387, particularly from a plant which has the genetic background or architecture at the QTL of line 061M4387, but especially from a plant of line 061M4387, representative seed of which is deposited at NCIMB under Accession. No. NCIMB 41428, or from a progeny or an ancestor thereof comprising said QTL, and defined by at least one marker locus, particularly to at least two marker loci, more particularly to at least three marker loci and even more particularly to at least four marker loci, but especially to at least five and up to six marker loci, which marker loci are on chromosome 3 and co-segregate with the *Bemisia* resistance trait and can be identified by a PCR oligonucleotide primer or a pair of PCR oligonucleotide primers selected from the group of primer pair 7 represented by a forward primer of SEQ ID NO: 13 and a reverse primer of SEQ ID NO: 14, identifying marker locus 7; primer pair 8 represented by a forward primer of SEQ ID NO: 15 and a reverse primer of SEQ ID NO: 16, identifying marker locus 8; primer pair 9 represented by a forward primer of SEQ ID NO: 17 and a reverse primer of SEQ ID NO: 18, identifying marker locus 9; primer pair 10 represented by a forward primer of SEQ ID NO: 19 and a reverse primer of SEQ ID NO: 20, identifying marker locus 10; primer pair 11 represented by a forward primer of SEQ ID NO: 21 and a reverse primer of SEQ ID NO: 22, identifying marker locus 11; primer pair 12 represented by a forward primer of SEQ ID NO: 23 and a reverse primer of SEQ ID NO: 24, identifying marker locus 12, and primer pair 13 represented by a forward primer of SEQ ID NO: 25 and a reverse primer of SEQ ID NO: 26, identifying marker locus 13.

In one embodiment, the invention therefore relates to a cultivated *Capsicum annuum* plant comprising a genome comprising at least two QTL which contribute to *Bemisia* and thrips resistance, which QTL are located on chromosomes 3 and 5 and wherein said at least two QTL can be identified by a molecular marker that exhibit statistical correlation to the phenotypic trait, which marker can be developed from a DNA segment containing said QTL by methods known in the art, which segment is obtainable from a plant which has the genetic background of line 061M4387, particularly from a plant which has the genetic background or architecture at the QTL of line 061M4387, but especially from a plant of line 061M4387, representative seed of which is deposited at NCIMB under Accession No. NCIMB 41428, or from a progeny or an ancestor thereof comprising said QTL, wherein a first QTL is located on chromosome 3 in the donor plant and genetically linked to at least one marker locus, particularly to at least two marker loci, particularly to at least three marker loci and particularly to at least four marker loci, particularly to at least five marker loci, particularly to at least six marker loci, which marker loci are on chromosome 3 and co-segregate with the Bemisia resistance trait and can be identified by a pair of PCR oligonucleotide primers 1 to 6 as given in SEQ ID NOs: 1 to 12 and a second QTL is located on chromosome 5 in the donor plant and genetically linked to at least one marker locus, particularly to at least two marker loci, particularly to at least three marker loci and particularly to at least four marker loci, particularly to at least five marker loci, particularly to at least six marker loci, and up to seven marker loci, which marker loci are on chromosome 5 and co-segregate with the Bemisia and/or thrips resistance trait and can be identified by a pair of PCR oligonucleotide primers selected from the group of primer pairs 7 to 13 as given in SEQ ID NOs: 13 to 26.

The markers according to the present invention may be used in marker-assisted-selection and/or any other methods wherein plants having or have not the QTL are traced. The markers may be either trans, or cis markers. A trans marker indicates a polymorphism resulting from introgression of exogenous (donor) DNA into a recipient plant's genome, which polymorphism is linked in cis with the recipient genome, i.e. linked with the opposite allele. Thus, cis markers are linked with the allele of interest (favorable QTL allele from the donor), while trans markers are linked with the opposite allele (from, the recipient).

To determine the utility of the inbred line and its potential to genetically contribute, to the hybrid progeny a test-cross is made with another inbred line, and the resulting progeny phenotypically evaluated. Traits that may be recorded commonly involve traits that are related to fruit shape and fruit characteristics such as pointed or non pointed fruit, pungent or non pungent, red, yellow or orange. Plant characteristics as length of internodes, growing power and ramifications are also considered together with specific virus resistances such as TMV (Tobacco Mosaic virus) and TSWV (Tomato Spotted wilt virus).

For genotyping, QTL mapping or association mapping DNA is extracted from suitable plant material such as, for example, leaf tissue. In particular, bulks of leaves of a plurality of plants are collected. DNA samples are genotyped using a plurality of polymorphic SSR's, SNPs or any other suitable marker-type covering the entire pepper genome.

Joint-analysis of genotypic and phenotypic data can be performed using standard software such as, for example, the software QTLCartographer and PlabQTL. Plant introductions and germplasm can be screened for the alleles at the corresponding QTLs disclosed in Table 10 and Table 11, respectively, based on the nucleotide sequence(s) of the marker(s) at the marker locus/loci linked to said QTL or any other marker known to be located on chromosome 3 and chromosome 5, respectively, and the molecular weight of the allele(s) using one or more of the techniques disclosed herein or known to those skilled in the art.

The nucleic acid sequence of markers disclosed, linked markers or the QTL of the present invention may be determined by methods known to the skilled person. For example, a nucleic acid sequence comprising said QTL or a resistance-conferring part thereof may be isolated from a Bemisia/Thrips resistant donor plant by fragmenting the genome of said plant and selecting those fragments harbouring one or more markers indicative of said QTL. Subsequently, or alternatively, the marker sequences (or parts thereof) indicative of said QTL may be used as (PCR) amplification primers, in order to amplify (a) nucleic acid sequence(s) comprising said QTL form a genomic nucleic acid sample or a genome fragment obtained from said plant. The nucleotide sequence of the QTL, and/or of any additional marker comprised therein, may be obtained by standard sequencing methods.

The present invention therefore also relates to an isolated nucleic acid (preferably DNA but not limited to DNA) sequence that comprises a QTL of the present invention, or a Bemisia/Thrips resistance-conferring part thereof. Thus the markers discloses may be used for the identification and isolation of one or more markers or genes from pepper or other vegetable crops, particularly Solanaceous crops that are linked or encode Bemisia/Thrips resistance.

The nucleotide sequence of additional linked markers or the QTL of the present invention may for instance also be resolved by determining the nucleotide sequence of one or more markers associated with the QTL and designing primers for said marker sequences that may then be used to further determine the sequence outside of said marker sequence. For example the nucleotide sequence of the SSR markers disclosed herein or any other markers predicted in the QTL region and/or linked to the QTL may be obtained by sequencing the PCR amplification product of said markers, well known in the art. Or alternatively using the marker sequences in a PCR or as hybridization probes to identify linked nucleotide sequences by for example but not limited BAC screening.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently claimed subject matter.

Example 1

Breeding History Pepper Breeding Line 061M4387

Using a quantitative bioassay as, described below in Example 2 in combination with the appropriate growing conditions a wild Capsicum annuum accession was identified as a source of resistance to Bemisia tabaci and to thrips infestations. Seeds of this wild accession with accession no: CGN16975 and accession name: AC 1979 was obtained from the Instituut voor de Veredeling van Tuinbouwgewassen (now Centre for Genetic Resources), Wageningen, Netherlands. A population segregating for the Bemisia and thrips resistance was created by crossing this donor pepper plant with a susceptible recipient, pepper plant. A segregating population consisting of a total of 333 DH lines was created for the identification of one or more QTLs contributing to the *Bemisia* and thrips resistance.

The initial source of resistance wild accession CGN16975 was crossed with a Dutch inbred of Syngenta selected in Westland (The Netherlands). The F3 progeny of this cross was identified as resistant, particularly intermediately resistant, to white fly (visual observation) in Almeria (Spain).

A (BC1) cross was then generated between the F3 mentioned in the previous paragraph and a Syngenta line developed in Almeria. The progeny of this cross was identified as resistant, particularly intermediately resistant, to white fly and thrips (in Agadir-Morocco; thrips—visual observations) and used for the next cross (BC2).

The BC2 was generated with a Syngenta dihaploid line developed in Almeria (Spain). From plant families in the F2 of this cross several (=333) dihaploids were developed to characterize the heredity of the trait of resistance to white fly and thrips. Among them, line 061M4387, deposited with NCIMB under accession no. NCIMB 41428 was shown to be intermediately resistant to *Bemisia tabaci* and thrips infestations.

Example 2

Resistance Assay

2A *Bemisia* Resistance—Testing Protocol
2A.1 Plant Raise

Plants were sown and raised according to standard procedures

In particular, plants were sown in a e.g. 77 multitray (multipots of 4.2×4.2×5.9 cm) filled with well drained, friable soil with a pH between 6.5 to 7.5 and grown for approx. one month in a tunnel. The plants were fertilized with N 4.0-6.0 P 0.35-1.0, K 4.0-6.0 of EC2.

The plants were transplanted according to special design (see below) and cultivated according to standard procedures. During plant culture, plants often need to be protected against parasites other than *Bemisia*. Chemical treatment was carried out with pesticides that only have a minor impact on the population development of *Bemisia*.

2A.2 Insect Culture and Inoculation

In order to ensure a stable and uniform development of the *Bemisia* population and to obtain more stringent testing conditions, an early inoculation of the plants with *Bemisia* was carried out. For this a separate small plastic greenhouse was used in which a pepper crop was raised under standard conditions. The naturally present *Bemisia* population was used to inoculate the test material.

Two methods can be used for inoculation:
1) Use of squash as a trap plant 2-3 week old seedlings of squash were placed in the small plastic greenhouse with the *Bemisia* culture for 4-6 hours. Because *Bemisia* adults have a strong preference for squash, they will rapidly fly to the squash seedlings. The squash plants with the *Bemisia* adults were then carefully enveloped with a plastic bag and transferred to the experimental tunnel and homogeneously released over the plants. Inoculation starts ca. 10 d after transplantation and can be continued for 1-2 wk as necessary.
2) The young pepper seedlings raised in trays were placed 4-5 days before transplantation in the small plastic greenhouse with the *Bemisia* culture allowing the adult *Bemisia* to lay eggs on the young plants. Hereafter the plants can be transplanted to the larger bitunnel.

2A.3 Experimental Design

A large bi-tunnel in Agadir was used with 8 rows of ca. 2×150 plants each. In each row one side was used as spreader row and planted with a susceptible entry (existing F1 e.g. Bikingo F1 or Vergasa F1, or, susceptible parental line). The other part of the row was planted with the test entries. The test entries were fully randomized in each of at least 7 blocks with 1 or more plants/entry per block.

2A.4 Data Collection

*Bemisia* development was monitored in the spreader row weekly or biweekly by assessing 5 spreader row plants on equidistant positions (plant 1, 38, 75, 112, 150) in each row. The final assessments were made when the average infestation of the monitored spreader plants was approx. 4 (Table 1) usually at the time when the first fruits are ripening (3-4 months after transplantation).

For assessing the severity, a scale from 1-9 was used (Table 1). The abaxial side of the leaves of the plant was inspected and the average of the ca. 5 worst affected leaves was assessed according the 1-9 scale. All test plants were scored in this way.

TABLE 1

Assessments scale for WF-resistance.

| scale | description WF | ## pupae[1] |
|---|---|---|
| 9 | no pupae | 0 |
| 8 | very few pupae | 1-5 |
| 7 | some pupae irregular scattered over leaf | 5-20 |
| 6 | | 20-50 |
| 5 | moderate number of pupae more regular distributed over leaves | 50-100 |
| 4 | | 100-200 |
| 3 | many pupae, densely crowded on leaf (black mould present) | 200-400 |
| 2 | | 400-700 |
| 1 | plant completely covered with pupae and heavily moulded often stunted in growth | 700-1000 |

[1]estimation of ## pupae per leaf: empty pupal cases and mature pupae 2A.5 Data Analysis Data were analyzed by calculating the means per test entry and comparison with a susceptible entry (e.g. susceptible spreader row or else). A multiple comparison of the means (e.g. LSD) indicates if test entries differ mutually and from a susceptible control.

2A.6 Results
2A.6.1 Resistance Testing

Table 2 shows some of the results of the *Bemisia* screening in Agadir (Morocco) of the deposited line 061M438 7 (containing QTL1 (referred to herein as the QTL on chromosome 3) and QTL2 (referred to herein as the QTL on chromosome 5), see example 3), two of its ancestors and the resistance donor. The breeding history is explained in example 1. The deposited line 061M4387 proved to be significantly better under varying insect pressures, seasons and conditions compared to standard susceptible varieties or lines.

TABLE 2

Results of tests with deposited line 061M4387 and some of its ancestors.

| Entry | Resistant line | Susc. control[1] | test | remark |
|---|---|---|---|---|
| CGN16975 (donor) | very resistant* | very susc.* | spring 2002 | *scored visually in breeding trial |
| BC1F3 | very resistant* | | | |

| | Mean | n | Mean | LSD[2] | | |
|---|---|---|---|---|---|---|
| CGN16975 (donor) | 8.8 | 20 | 6.6 | 0.4 | December 2002 | insect pressure relatively low |
| BC1F4 deposited line | 8.5 | 20 | | | | |
| 061M4387 | 8.0 | 7 | 4.2 | 1.2 | August 2005 | moderate-high insect pressure |
| 061M4387 | 6.4 | 7 | 3.0 | 1.5 | November 2005 | very high insect pressure |
| 061M4387 | 6.7 | 20 | 3.8 | 0.6 | June 2006 | high insect pressure |
| 061M4387 | 8.0 | 10 | 5.2 | 1.4 | February 2007 | moderate insect pressure |

[1]In the above trials Vergasa F1, Bikingo F1 or parental lines (all susceptible) are used as both susceptible control and as spreader row.
[2]LSD intervals(P < 0.05) are based on comparison of means of many entries included in trial (not shown).

2A.6.2 QTL Identification Associated with Resistance

Table 3 shows the results of a screening of a set of 333 DH lines developed out of a BC2F2 for the purpose of identification of QTLs associated with resistance (see examples 1 and 3). Two tests were performed on the DH-lines: test 1 was planted in spring 2005 and scored in August, the second test was planted in September 2005 and scored in November. The average infestation in August was lower compared to November (Table 3). In the November trial some spots in the greenhouse had a very high insect pressure with as consequence that no reliable phenotypes could be obtained. Those, spots were therefore excluded from the analysis.

Two QTLs were identified (see example 3). The QTL (QTL1) on chromosome 3 had the largest LOD-value (up to 50), the QTL (QTL2) on chromosome 5 had a smaller LOD-value (up to 5).

Based on flanking markers 69 DH-lines were identified having no QTLs, 57 DH-lines had QTL1 only, 38 DH-lines had QTL2 only, and, 63 DH-lines possessed QTL1 and QTL2 together.

The effect of QTL1 was in both trials significant and estimated in the August trial 1.3 scale units and in November trial 1.9 scale units (Table 3). Due to the lower infestation in August many lines scored a 7-8 reaching a plafond possibly minimizing differences between lines. In the November trial the differences between lines were larger due to the higher infestation level.

The effect of QTL2 was more pronounced in the August trial (0.6 scale unit) compared to the November trial.

TABLE 3

Results of a screening of a set of 333 DH lines developed out of a BC2F2 for the purpose of identification of QTLs associated with resistance

| | no QTL | QTL1 | QTL2 | QTL1&2 |
|---|---|---|---|---|
| August | 5.9a* | 7.2c | 6.5b | 7.6d |
| November | 4.1a | 6.0b | 4.3a | 6.1b |
| Avg | 5.0 | 6.6 | 5.4 | 6.8 |

*similar letters show no statistical difference (LSD, P < 0.05) within observation period 2A.6.3 Test of Effect of QTL1 in 5 BC3 Families To estimate the effect of QTL1 in different background families, five BC3's were made with 5 different BC-parents and a derivative resistant line containing QTL1. 556 DH-lines derived from these BC3's were genotyped for QTL1 and tested in Agadir (February 2007, Table 4) under the same conditions described previously. The effect of QTL1 was estimated between 1.8-2.3 scale units for the different families (Table 4) confirming the significant effect of QTL1 (Two-way ANOVA, Mean Square QTL1=521.3, F=698.7, P<0.001, no interactions between family and QTL1 presence).

TABLE 4

Effect of QTL1 on *Bemisia* infestation in 5 BC3 families tested in Agadir February 2007.

| family | QTL1 presence | mean | n | diff. |
|---|---|---|---|---|
| 1 | no QTL | 5.2 | 51 | 1.8 |
| | QTL1 | 7.0 | 46 | |
| 2 | no QTL | 4.7 | 47 | 2.0 |
| | QTL1 | 6.8 | 38 | |
| 3 | no QTL | 5.2 | 60 | 2.1 |
| | QTL1 | 7.3 | 145 | |
| 4 | no QTL | 4.9 | 37 | 2.2 |
| | QTL1 | 7.2 | 57 | |
| 5 | no QTL | 4.9 | 42 | 2.3 |
| | QTL1 | 7.3 | 33 | |
| | total | | 556 | |

2A.6.4 Test of the Effect of QTLs 1 and 2 on *Bemisia* Damage in a Set of 60 DH Lines Derived from a Cross with Donor CGN16975 and Two Elite Pepper Lines.

The initial source of resistance wild accession CGN16975 was crossed with two elite lines (A and B). From these two F1's in total 60 dihaploid lines (34 from line A and 26 from line B) were derived. 58 of these lines were tested mostly twice (between December 2003 and December 2004) for *Bemisia* resistance.

TABLE 5

Estimated effect of QTL 1 and 2 on *Bemisia* resistance in a small DH population derived out of F1 between wild accession CGN16975 and 2 elite pepper lines.

|  | no QTL<br>n = 11 | QTL1<br>n = 17 | QTL2<br>n = 17 | QTL1&2<br>n = 13 |
|---|---|---|---|---|
| average | 4.0a* | 5.9.0b | 5.1ab | 5.9b |

Given is the average of 2 tests.
*Similar letters indicate no significant differences (ANOVA, followed by comparison of means with Fisher's Least Significance Difference method LSD, P < 0.05).
**significantly different from no QTL at P = 0.06.

The effect of QTL1 was estimated on ca. 1.9 scale units and the effect of QTL 2 was estimated on 1.1 scale units in these populations.

2B Thrips Resistance—Testing Protocol 2B.1 Plant Raise

Plants were sown in standard peat soil and transplanted after 14 d into 7×7×8×cm pots. The plants were grown in a greenhouse at 20° C./18° C. and 16 hr/8 hr day/night. Approximately 1 month after sowing, the plants were transferred to a 1×1×1 m cage covered with a nylon mesh (0.07× 0.27 mm) preventing thrips from leaving the cage. In each cage 400-500 thrips were released. This was repeated 1 week later to ensure a high insect pressure. Three-four weeks after the first inoculation, the observation was done.

2B.2 Insect Culture and Inoculation

A viable culture of thrips was maintained and used for resistance experiments. From the culture 400-500 thrips (including both adults and juveniles) were collected in a vial with a standard insect sucking device. The vial with thrips was subsequently released in the test cage. After inoculation the temperature was raised to 24° C. continuous (day/night).

2B.3 Experimental Design

In each cage one or more resistant controls (preferably CGN16975) and one or more susceptible controls (e.g. Roxy F1 and/or Snooker F1) were placed. In total 57 plants can be placed in a single cage. The plants (including the control plants) were randomized for each cage. The DH lines tested for *Bemisia* (see Example 1 above) were tested for thrips resistance in this way. Seven consecutive experiments were performed in order to test all 333 DH lines with (max.) 12 plants per line.

2B.4 Data Collection

The final assessments were made when the average infestation of the susceptible control plants was 3-4 (Table 6). Usually this is reached 3-4 weeks after inoculation.

For assessing silvering damage, a scale from 1-9 was used (Table 6). The abaxial side of the leaves of the plant was inspected and the average of the ca. 2-3 worst affected leaves was assessed according the 1-9 scale. All test plants were scored in this way.

TABLE 6

Assessment scale for silvering damage caused by *Frankliniella occidentalis*.

| scale | description Thrips damage | % silvering[1] |
|---|---|---|
| 9 | no silvering damage | 0 |
| 8 | tiny spots | <0.1 |
| 7 | some small spots especially near the mid vein or edge of the leaf | 0.1-1 |
| 6 |  | 1-2 |
| 5 | moderate number of spots more regular distributed over leaves | 3-5 |

TABLE 6-continued

Assessment scale for silvering damage caused by *Frankliniella occidentalis*.

| scale | description Thrips damage | % silvering[1] |
|---|---|---|
| 4 |  | 6-10 |
| 3 | many large silvering spots present distributed over the entire leaf | 11-20 |
| 2 |  | 21-40 |
| 1 | very heavy silvering, large part of the leaf damaged | >40 |

[1]estimation of % silvering of 2-3 most affected leaves 2B.5 Data Analysis

Data were analyzed by calculating the means per test entry and comparison with a susceptible entry (e.g. Roxy F1 and/or Snooker F1). A multiple comparison of the means (e.g. LSD) indicated if test entries differ mutually and, from a susceptible control.

2B.6 Results 2B.6.1 Resistance Testing

Table 7 shows as an example the results of CGN16975, two susceptible controls (Roxy F1 and Snooker F1) and the deposited line 061M4387 possessing QTL1 and QTL2. Averages of 3 independent tests each with ca. 12 plants/entry are given. The deposited line showed significantly less silvering compared to the two susceptible control lines Snooker F1 and Roxy F1 but more silvering compared to the donor CGN16975. This indicates that the deposited line has an elevated level of resistance compared to standard varieties.

TABLE 7

Phenotyping results of deposited line 061M4387, CGN16975 and two susceptible varieties (Roxy F1 and Snooker F1).

| entry | n | silvering* |
|---|---|---|
| Snooker F1 | 36 | 3.5a |
| Roxy F1 | 36 | 3.8a |
| 061M4387 | 31 | 5.8b |
| CGN16975 | 36 | 7.3c |

*Simlar letters indicate no significant differences (ANOVA, followed by comparison of means with Fisher's Least Significance Difference method LSD, P < 0.05).

2B.6.2 QTL Identification Associated with Resistance to Thrips

The QTL-analysis (see example 3) on the 333 DH lines (see example 1) revealed a QTL on chromosome 5, with a LOD value up to 12. This QTL, was located in the same region as QTL2 identified in the *Bemisia* QTL mapping (see example 2A.6)

The QTL for *Bemisia* on chromosome 5 and the QTL for thrips are located on the same chromosomal region. It could be a single QTL with an effect both against *Bemisia* and thrips or two linked QTLs 2B.6.3 Test of Effect of QTL2 on Thrips Damage in a Set of 333 DH Lines Developed Out of a BC2F2

The effect of the thrips QTL was estimated similarly as was done for *Bemisia* (see 2A.6) based on the large 333 DH set. The QTL showed a significant effect of ca. 0.8 scale unit (Table 8).

TABLE 8

Estimated effect of QTL 2 on thrips damage (silvering)
in large BC2F2 population of 333 DH lines (possible
recombinants were excluded).

|  | no QTL<br>n = 122 | QTL2<br>n = 91 |
|---|---|---|
| Silvering | 4.5 | 5.3* |

*Significant difference (t-test, t = −8.29, P < 0.001).

2B.6.4 Test of the Effect of QTL2 on Thrips Damage in a Set of 60 DH Lines Derived from a Cross with Donor CGN16975 and Two Elite Pepper Lines.

53 DH lines of the same set of 60 DH lines derived from accession CGN16975 crossed with two elite lines (A and B, see section 2A.6.4) were subjected twice to a thrips test and checked for the presence of QTL2.

QTL2 showed a significant effect of 1.0 scale units (Table 9) which is on a comparable level as in the large 333 DH set described in 2B.6.3 (Table 8).

TABLE 9

Estimated effect of QTL 2 on thrips damage (silvering)
in a small DH population derived out of F1 between
wild accession CGN16975 and 2 elite pepper lines.

|  | no QTL<br>n = 26 | QTL2<br>n = 27 |
|---|---|---|
| Silvering | 4.3 | 5.3* |

*Significant difference (t-test, t = −3.86, P < 0.001).

Example 3

QTL Mapping 3.1 QTL Mapping for *Bemisia* Resistance

Using the quantitative bioassay described above in Example 2A in combination with appropriate growing conditions a source of resistance to *Bemisia* was identified. A population segregating for the *Bemisia* resistance was created by crossing this donor pepper plant with a susceptible recipient pepper plant. A segregating population consisting of a total of 333 DH lines was created for the identification of QTL contributing to the *Bemisia* resistance. DNA was extracted from a pool of leaves of 8 individual plants of each DH line and the parent plants of the population following standard protocols. The parents of the population were screened using several hundred SSR's in order to identify SSR's which are polymorphic between the parents. Subsequently the DH population was genotyped using the identified polymorphic SSR markers. Based on the so obtained segregation data a molecular marker map was prepared using the commonly used software Mapmaker and Joinmap. The markers represent genome regions polymorphic between the parents of the population.

QTL mapping, i.e. joint analysis of genotypic and phenotypic data was performed using the QTLCartographer software. QTLs were identified which are located on different chromosomes including a QTL on chromosome 3, which was demonstrated to be associated to *Bemisia* resistance. The QTL is characterized by means of markers positioned on the genetic map and marker alleles of markers known to be located in the QTL region. Thereby the location of a/multiple resistance conferring DNA sequences is/are established. Details of the QTL associated with resistance to *Bemisia*, i.e. flanking markers and markers located in the QTL region are represented in Table 10.

3.2 QTL Mapping for Thrips Resistance

The identical approach as described in Example 3.1 above was taken for mapping the QTL associated with resistance to thrips.

A QTL, which was demonstrated to be associated to thrips resistance, was identified on chromosome 5. The QTL is characterized by means of markers positioned on the genetic map and marker alleles of markers known to be located in the QTL region. Thereby the location of a/multiple resistance conferring DNA sequences is/are established. Details of the QTL associated with resistance to thrips, i.e. flanking markers and markers located in the QTL region are represented in Table 11.

TABLE 10

Details of the QTL associated with resistance to *Bemisia*, i.e.
flanking markers and markers located in the QTL region

| Bemisia<br>Resistance<br>QTL # | Chromo-<br>some<br># | Marker<br>Locus | Linked<br>Marker | Forward Primer | F Primer<br>Sequence ID<br>Number | Reverse Primer | R Primer<br>Sequence ID<br>Number |
|---|---|---|---|---|---|---|---|
| 1 | 3 | 1 | LM 1001 | TGCTGGGAAAGATCTCAAAAGG | SEQ. ID. NO: 1 | ATCAAGGAAGCAAACCAATGC | SEQ. ID. NO: 2 |
| 1 | 3 | 2 | LM 1002 | GCAGCGTTACCAAATAACCG | SEQ. ID. NO: 3 | TGTTTGCTATTCAATATATGCTTTGA | SEQ. ID. NO: 4 |
| 1 | 3 | 3 | LM 1003 | GGAAGCTTAGCCACACATC | SEQ. ID. NO: 5 | ACCATATTTCCGACTTTGAAC | SEQ. ID. NO: 6 |
| 1 | 3 | 4 | LM 1004 | TCCATCATCGACTGGAGAC | SEQ. ID. NO: 7 | TGTTCAATTGGCTTCTGTG | SEQ. ID. NO: 8 |
| 1 | 3 | 5 | LM 1005 | GCAAGTAGAACAAAGGGTAGG | SEQ. ID. NO: 9 | TATTTGAAGGTTGTGCGAC | SEQ. ID. NO: 10 |
| 1 | 3 | 6 | LM 1006 | TCATCACATTCACTTCATTTTC | SEQ. ID. NO: 11 | TTGATTCATTTCAGATAGTTCAAG | SEQ. ID. NO: 12 |

TABLE 11

Details of the QTL associated with resistance to thrips, i.e. flanking markers and markers located in the QTL region

| Bemisia/ Thrips Resistance QTL # | Chromo- some # | Marker Locus | Linked Marker | Forward Primer | F Primer Sequence ID Number | Reverse Primer | R Primer Sequence ID Number |
|---|---|---|---|---|---|---|---|
| 2 | 5 | 7 | LM 2001 | CTTTGGAGGTAGCGGTATG | SEQ. ID. NO: 13 | CAACAAACGAACCACAATG | SEQ. ID. NO: 14 |
| 2 | 5 | 8 | LM 2002 | CCCGTTTACAAGCAAAGAG | SEQ. ID. NO: 15 | GACCCCTGAAGAACCTTC | SEQ. ID. NO: 16 |
| 2 | 5 | 9 | LM 2003 | TCTCTTGTCAGACACGTCG | SEQ. ID. NO: 17 | CTTCTTGGAGGCATTTTTG | SEQ. ID. NO: 18 |
| 2 | 5 | 10 | LM 2004 | TGTAGGATTACAAGAACATTATCG | SEQ. ID. NO: 19 | GCGAGCTATTACACCGAAG | SEQ. ID. NO: 20 |
| 2 | 5 | 11 | LM 2005 | TAGGTGGGAATACACTGGG | SEQ. ID. NO: 21 | CCCAGATCTACCAAGGAGTC | SEQ. ID. NO: 22 |
| 2 | 5 | 12 | LM 2006 | TCGGCCTGACTAGTATTGAC | SEQ. ID. NO: 23 | CGGGTACCAGATGTAGGG | SEQ. ID. NO: 24 |
| 2 | 5? | 13 | LM 2007 | ATCGTGAGGTGAGTACGAG | SEQ. ID. NO: 25 | TACCTACATACCCCCACCC | SEQ. ID. NO: 26 |

Deposit

Applicants have made a deposit with an effective date of 10 Aug. 2006 of at least 2500 seeds of *Capsicum annuum* line 061M4387 with the NCIMB; Ltd, Ferguson Building, Craibstone Estate, Bucksburn, Aberdeen, AB21 9YA, Scotland, under accession no: NCIMB 41428.

The foregoing invention has been described in detail by way of Illustration and example for purposes of clarity and understanding. However, it will be obvious that certain changes and modifications such as single gene modifications and mutations, somaclonal variants, variant individuals selected from large populations of the plants of the instant inbred and the like may be practiced within the scope of the invention, as limited only by the scope of the appended claims. Thus, although the foregoing invention has been described in some detail in this document, it will be obvious that changes and modification may be practiced within the scope of the invention, as limited only by the scope of the appended claims.

All references cited herein are incorporated by reference in the application in their entireties.

The invention claimed is:

1. A cultivated *Capsicum annuum* plant which is intermediately resistant to thrips infestation, wherein said resistance can be assessed in a standard resistance assay,
wherein said plant comprises a first QTL contributing to said intermediate resistance to thrips infestation,
wherein said first QTL is located on chromosome 3 and said first QTL is obtained from a plant of line 061 M4387, representative seed of which is deposited under Accession No. NCIMB 41428, or from a progeny or an ancestor thereof comprising said QTL,
wherein said first QTL is genetically linked to at least one marker locus co-segregating with said intermediate resistance to thrips infestation,
wherein said at least one marker locus can be identified by a pair of PCR oligonucleotide primers selected from the group consisting of primer pair 1 represented by a forward primer of SEQ ID NO: 1 and a reverse primer of SEQ ID NO: 2, identifying marker locus 1; primer pair 2 represented by a forward primer of SEQ ID NO: 3 and a reverse primer of SEQ ID NO: 4, identifying marker locus 2; primer pair 3 represented by a forward primer of SEQ ID NO: 5 and a reverse primer of SEQ ID NO: 6, identifying marker locus 3; primer pair 4 represented by a forward primer of SEQ ID NO: 7 and a reverse primer of SEQ ID NO: 8, identifying marker locus 4; primer pair 5 represented by a forward primer of SEQ ID NO: 9 and a reverse primer of SEQ ID NO: 10, identifying marker locus 5; and primer pair 6 represented by a forward primer of SEQ ID NO: 11 and a reverse primer of SEQ ID NO: 12, identifying marker locus 6.

2. The cultivated *Capsicum annuum* plant according to claim 1,
wherein said plant additionally comprises a second QTL contributing to said intermediate resistance to thrips infestation,
wherein said second QTL is located on chromosome 5 and said second QTL is obtained from a plant of line 061 M4387, representative seed of which is deposited under Accession No. NCIMB 41428, or from a progeny or an ancestor thereof comprising said second QTL,
wherein said second QTL is genetically linked to at least one marker locus co-segregating with said intermediate resistance to thrips infestation,
wherein said at least one marker locus genetically linked to said second QTL can be identified by a pair of PCR oligonucleotide primers selected from the group consisting of primer pair 7 represented by a forward primer of SEQ ID NO: 13 and a reverse primer of SEQ ID NO: 14, identifying marker locus 7; primer pair 8 represented by a forward primer of SEQ ID NO: 15 and a reverse primer of SEQ ID NO: 16, identifying marker locus 8;

primer pair 9 represented by a forward primer of SEQ ID NO: 17 and a reverse primer of SEQ ID NO: 18, identifying marker locus 9; primer pair 10 represented by a forward primer of SEQ ID NO: 19 and a reverse primer of SEQ ID NO: 20, identifying marker locus 10; primer pair 11 represented by a forward primer of SEQ ID NO: 21 and a reverse primer of SEQ ID NO: 22, identifying marker locus 11; primer pair 12 represented by a forward primer of SEQ ID NO: 23 and a reverse primer of SEQ ID NO: 24, identifying marker locus 12, and primer pair 13 represented by a forward primer of SEQ ID NO: 25 and a reverse primer of SEQ ID NO: 26, identifying marker locus 13.

3. A cultivated *Capsicum annuum* plant, according to claim 1, wherein forward and reverse primers representing primer pairs 1-13 exhibit a nucleotide sequence which is at least 90% identical to that given in SEQ ID NO: 1-26.

4. A seed of a plant according to claim 1.

5. A part of a plant according to claim 1.

6. A fruit of a plant according to claim 1.

7. The cultivated *Capsicum annuum* plant according to claim 2 which is intermediately resistant to *Bemisia* and thrips infestation, wherein said resistances can be assessed in standard resistance assays.

* * * * *